(12) United States Patent
White et al.

(10) Patent No.: US 11,666,467 B2
(45) Date of Patent: *Jun. 6, 2023

(54) HEMOSTASIS VALVE AND DELIVERY SYSTEMS

(71) Applicant: Bolton Medical, Inc., Sunrise, FL (US)

(72) Inventors: Bryan White, Sunrise, FL (US);
Timothy Lostetter, Sunrise, FL (US);
Scott Lyle Rush, Sunrise, FL (US);
John C. Canning, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 204 days.

This patent is subject to a terminal disclaimer.

(21) Appl. No.: 16/721,016

(22) Filed: Dec. 19, 2019

(65) Prior Publication Data

US 2020/0121483 A1 Apr. 23, 2020

Related U.S. Application Data

(60) Division of application No. 15/230,601, filed on Aug. 8, 2016, now Pat. No. 10,555,826, which is a
(Continued)

(51) Int. Cl.
*A61F 2/966* (2013.01)
*A61F 2/07* (2013.01)
(Continued)

(52) U.S. Cl.
CPC ............ *A61F 2/966* (2013.01); *A61F 2/07* (2013.01); *A61F 2/89* (2013.01); *A61F 2/954* (2013.01);
(Continued)

(58) Field of Classification Search
CPC .. A61F 2/95; A61F 2/962; A61F 2/966; A61F 2/2427; A61F 2/2436; A61F 2/2466; A61F 2002/9517
See application file for complete search history.

(56) References Cited

U.S. PATENT DOCUMENTS

| 3,416,531 A | 12/1968 | Edwards |
| 3,485,234 A | 12/1969 | Stevens |

(Continued)

FOREIGN PATENT DOCUMENTS

| CN | 2451136 Y | 10/2001 |
| CN | 2518466 Y | 10/2002 |

(Continued)

OTHER PUBLICATIONS

Notice of Allowance for U.S. Appl. No. 12/459,387 dated May 3, 2016.
(Continued)

*Primary Examiner* — Todd J Scherbel
(74) *Attorney, Agent, or Firm* — Stephen J. Kenny; Vincenzo DiMonaco; Foley Hoag LLP

(57) ABSTRACT

A stent graft delivery system for delivering an aortic prosthetic device includes a handle, an internal lead screw assembly within a track of a handle body of the handle, a lead screw nut that extends about the handle body and threadable engaged with the threaded portion of the internal lead screw assembly, a support member fixed to the handle body, a sheath extending about a portion of the support member and fixed to the internal lead screw assembly, and a hemostasis valve about the supporting member and between the sheath and the lead screw assembly.

10 Claims, 84 Drawing Sheets

Related U.S. Application Data continuation of application No. 13/834,808, filed on Mar. 15, 2013, now Pat. No. 9,439,751.

(51) Int. Cl.
*A61F 2/962* (2013.01)
*A61F 2/954* (2013.01)
*A61F 2/89* (2013.01)
A61F 2/848 (2013.01)
A61F 2/24 (2006.01)

(52) U.S. Cl.
CPC .......... *A61F 2/2427* (2013.01); *A61F 2/2436* (2013.01); *A61F 2/2466* (2013.01); *A61F 2002/8483* (2013.01); *A61F 2002/8486* (2013.01)

(56) References Cited

U.S. PATENT DOCUMENTS

| | | |
|---|---|---|
| 3,502,069 A | 3/1970 | Silverman |
| 3,868,956 A | 3/1975 | Alfidi et al. |
| 4,351,333 A | 9/1982 | Lazarus et al. |
| 4,425,919 A | 1/1984 | Alston, Jr. et al. |
| 4,487,808 A | 12/1984 | Lambert |
| 4,515,593 A | 5/1985 | Norton |
| 4,516,972 A | 5/1985 | Samson |
| 4,534,363 A | 8/1985 | Gold |
| 4,572,186 A | 2/1986 | Gould et al. |
| 4,580,568 A | 4/1986 | Gianturco |
| 4,634,432 A | 1/1987 | Kocak |
| 4,655,771 A | 4/1987 | Wallsten |
| 4,665,906 A | 5/1987 | Jervis |
| 4,665,918 A | 5/1987 | Garza et al. |
| 4,705,511 A | 11/1987 | Kocak |
| 4,787,899 A | 11/1988 | Lazarus |
| 4,817,613 A | 4/1989 | Jaraczewski et al. |
| 4,990,151 A | 2/1991 | Wallsten et al. |
| 5,000,745 A | 3/1991 | Guest et al. |
| 5,019,057 A | 5/1991 | Truckai |
| 5,041,126 A | 8/1991 | Gianturco |
| 5,057,092 A | 10/1991 | Webster, Jr. |
| 5,067,957 A | 11/1991 | Jervis |
| 5,104,399 A | 4/1992 | Lazarus |
| 5,123,917 A | 6/1992 | Lee |
| 5,154,701 A * | 10/1992 | Cheer ............... A61M 39/0606 137/849 |
| 5,158,543 A | 10/1992 | Lazarus |
| 5,176,652 A * | 1/1993 | Littrell ............. A61M 39/0606 137/849 |
| 5,176,660 A | 1/1993 | Truckai |
| 5,201,757 A | 4/1993 | Heyn et al. |
| 5,254,105 A | 10/1993 | Haaga |
| 5,282,824 A | 2/1994 | Gianturco |
| 5,290,295 A | 3/1994 | Querals et al. |
| 5,292,331 A | 3/1994 | Boneau |
| 5,306,263 A | 4/1994 | Voda |
| 5,324,306 A | 6/1994 | Makower et al. |
| 5,334,164 A | 8/1994 | Guy et al. |
| 5,334,168 A | 8/1994 | Hemmer |
| 5,338,295 A | 8/1994 | Cornelius et al. |
| 5,342,384 A | 8/1994 | Sugarbaker |
| 5,358,493 A | 10/1994 | Schweich, Jr. et al. |
| 5,380,304 A | 1/1995 | Parker |
| 5,387,235 A | 2/1995 | Chuter |
| 5,397,345 A | 3/1995 | Lazarus |
| 5,405,377 A | 4/1995 | Cragg |
| 5,415,664 A | 5/1995 | Pinchuk |
| 5,429,617 A | 7/1995 | Hammersmark et al. |
| 5,433,723 A | 7/1995 | Lindenberg et al. |
| 5,456,713 A | 10/1995 | Chuter |
| 5,458,615 A | 10/1995 | Klemm et al. |
| 5,464,449 A | 11/1995 | Ryan et al. |
| 5,474,563 A | 12/1995 | Myler et al. |
| 5,480,423 A | 1/1996 | Ravenscroft et al. |
| 5,489,295 A | 2/1996 | Piplani et al. |
| 5,507,769 A | 4/1996 | Marin et al. |
| 5,507,771 A | 4/1996 | Gianturco |
| 5,522,881 A | 6/1996 | Lentz |
| 5,522,882 A | 6/1996 | Gaterud et al. |
| 5,531,715 A | 7/1996 | Engelson et al. |
| 5,533,987 A | 7/1996 | Pray et al. |
| 5,534,007 A | 7/1996 | St. Germain et al. |
| 5,540,712 A | 7/1996 | Kleshinski et al. |
| 5,545,210 A | 8/1996 | Hess et al. |
| 5,549,565 A | 8/1996 | Ryan et al. |
| 5,562,726 A | 10/1996 | Chuter |
| 5,562,728 A | 10/1996 | Lazarus et al. |
| 5,569,218 A | 10/1996 | Berg |
| 5,571,135 A | 11/1996 | Fraser et al. |
| 5,575,816 A | 11/1996 | Rudnick et al. |
| 5,575,817 A | 11/1996 | Martin |
| 5,582,614 A | 12/1996 | Feingold |
| 5,591,194 A | 1/1997 | Berthiaume |
| 5,591,195 A | 1/1997 | Taheri et al. |
| 5,597,378 A | 1/1997 | Jervis |
| 5,601,568 A | 2/1997 | Chevillon et al. |
| 5,607,442 A | 3/1997 | Fischell et al. |
| 5,609,625 A | 3/1997 | Piplani et al. |
| 5,609,627 A | 3/1997 | Goicoechea et al. |
| 5,613,974 A | 3/1997 | Andreas et al. |
| 5,618,270 A | 4/1997 | Orejola |
| 5,628,754 A | 5/1997 | Shevlin et al. |
| 5,628,783 A | 5/1997 | Quiachon et al. |
| 5,632,763 A | 5/1997 | Glastra |
| 5,639,278 A | 6/1997 | Dereume et al. |
| 5,658,263 A | 8/1997 | Dang et al. |
| 5,662,675 A | 9/1997 | Polanskyj Stockert et al. |
| 5,662,700 A | 9/1997 | Lazarus |
| 5,674,208 A | 10/1997 | Berg et al. |
| 5,676,696 A | 10/1997 | Marcade |
| 5,683,449 A | 11/1997 | Marcade |
| 5,693,084 A | 12/1997 | Chuter |
| 5,693,086 A | 12/1997 | Goicoechea et al. |
| 5,695,517 A | 12/1997 | Marin et al. |
| 5,700,269 A | 12/1997 | Pinchuk et al. |
| 5,707,376 A | 1/1998 | Kavteladze et al. |
| 5,709,703 A | 1/1998 | Lukic et al. |
| 5,713,917 A | 2/1998 | Leonhardt et al. |
| 5,716,365 A | 2/1998 | Goicoechea et al. |
| 5,716,393 A | 2/1998 | Lindenberg et al. |
| 5,720,776 A | 2/1998 | Chuter et al. |
| 5,723,003 A | 3/1998 | Winston et al. |
| 5,730,733 A | 3/1998 | Mortier et al. |
| 5,733,267 A | 3/1998 | Del Toro |
| 5,735,859 A | 4/1998 | Fischell et al. |
| 5,741,327 A | 4/1998 | Frantzen |
| 5,749,921 A | 5/1998 | Lenker et al. |
| 5,755,778 A | 5/1998 | Kleshinski |
| 5,776,142 A | 7/1998 | Gunderson |
| 5,782,811 A | 7/1998 | Samson et al. |
| 5,782,904 A | 7/1998 | White et al. |
| 5,782,909 A | 7/1998 | Quiachon et al. |
| 5,788,707 A | 8/1998 | Del Toro et al. |
| 5,792,144 A | 8/1998 | Fischell et al. |
| 5,800,515 A | 9/1998 | Nadal et al. |
| 5,800,517 A | 9/1998 | Anderson et al. |
| 5,800,520 A | 9/1998 | Fogarty et al. |
| 5,807,405 A | 9/1998 | Vanney et al. |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,851,228 A | 12/1998 | Pinheiro |
| 5,860,998 A | 1/1999 | Robinson et al. |
| 5,871,536 A | 2/1999 | Lazarus |
| 5,891,110 A | 4/1999 | Larson et al. |

(56) References Cited

U.S. PATENT DOCUMENTS

| | | |
|---|---|---|
| 5,891,114 A | 4/1999 | Chien et al. |
| 5,893,868 A | 4/1999 | Hanson et al. |
| 5,899,892 A | 5/1999 | Mortier et al. |
| 5,902,334 A | 5/1999 | Dwyer et al. |
| 5,904,713 A | 5/1999 | Leschinsky |
| 5,906,619 A | 5/1999 | Olson et al. |
| 5,910,101 A | 6/1999 | Andrews et al. |
| 5,911,715 A | 6/1999 | Berg et al. |
| 5,916,263 A | 6/1999 | Goicoechea et al. |
| 5,938,696 A | 8/1999 | Goicoechea et al. |
| 5,944,726 A | 8/1999 | Blaeser et al. |
| 5,947,939 A | 9/1999 | Mortier et al. |
| 5,951,495 A | 9/1999 | Berg et al. |
| 5,954,651 A | 9/1999 | Berg et al. |
| 5,957,949 A | 9/1999 | Leonhardt et al. |
| 5,961,511 A | 10/1999 | Mortier et al. |
| 5,968,069 A | 10/1999 | Dusbabek et al. |
| 5,984,955 A | 11/1999 | Wisselink |
| 5,993,481 A | 11/1999 | Marcade et al. |
| 6,004,310 A | 12/1999 | Bardsley et al. |
| 6,004,328 A | 12/1999 | Solar |
| 6,004,347 A | 12/1999 | McNamara et al. |
| 6,019,778 A | 2/2000 | Wilson et al. |
| 6,024,763 A | 2/2000 | Lenker et al. |
| 6,039,749 A | 3/2000 | Marin et al. |
| 6,039,758 A | 3/2000 | Quiachon et al. |
| 6,039,759 A | 3/2000 | Carpentier et al. |
| 6,045,557 A | 4/2000 | White et al. |
| 6,051,020 A | 4/2000 | Goicoechea et al. |
| 6,053,943 A | 4/2000 | Edwin et al. |
| 6,063,112 A | 5/2000 | Sgro |
| 6,071,307 A | 6/2000 | Rhee |
| 6,077,297 A | 6/2000 | Robinson et al. |
| 6,099,548 A | 8/2000 | Taheri |
| 6,099,558 A | 8/2000 | White et al. |
| 6,099,559 A | 8/2000 | Nolting |
| 6,110,191 A | 8/2000 | Dehdashtian et al. |
| 6,110,198 A | 8/2000 | Fogarty et al. |
| 6,117,167 A | 9/2000 | Goicoechea et al. |
| 6,120,480 A | 9/2000 | Zhang et al. |
| 6,123,723 A | 9/2000 | Konya et al. |
| 6,152,944 A | 11/2000 | Holman et al. |
| 6,165,163 A | 12/2000 | Chien et al. |
| 6,165,213 A | 12/2000 | Goicoechea et al. |
| 6,168,616 B1 | 1/2001 | Brown, III |
| 6,168,623 B1 | 1/2001 | Fogarty et al. |
| 6,171,334 B1 | 1/2001 | Cox |
| 6,183,481 B1 | 2/2001 | Lee et al. |
| 6,183,505 B1 | 2/2001 | Mohn, Jr. et al. |
| 6,183,506 B1 | 2/2001 | Penn et al. |
| 6,193,705 B1 | 2/2001 | Mortier et al. |
| 6,200,336 B1 | 3/2001 | Pavcnik et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,435 B1 | 4/2001 | Piplani et al. |
| 6,212,422 B1 | 4/2001 | Berg et al. |
| 6,213,976 B1 | 4/2001 | Trerotola |
| 6,214,038 B1 | 4/2001 | Piplani et al. |
| 6,221,079 B1 | 4/2001 | Magovern et al. |
| 6,221,102 B1 | 4/2001 | Baker et al. |
| 6,224,609 B1 | 5/2001 | Ressemann et al. |
| 6,228,063 B1 | 5/2001 | Aboul-Hosn |
| 6,231,601 B1 | 5/2001 | Myers et al. |
| 6,238,430 B1 | 5/2001 | Klumb et al. |
| 6,245,052 B1 | 6/2001 | Orth et al. |
| 6,248,112 B1 | 6/2001 | Gambale et al. |
| 6,248,116 B1 | 6/2001 | Chevillon et al. |
| 6,251,132 B1 | 6/2001 | Ravenscroft et al. |
| 6,254,609 B1 | 7/2001 | Vrba et al. |
| 6,267,775 B1 | 7/2001 | Clerc et al. |
| 6,270,521 B1 | 8/2001 | Fischell et al. |
| 6,273,909 B1 | 8/2001 | Kugler et al. |
| 6,280,464 B1 | 8/2001 | Hayashi |
| 6,280,466 B1 | 8/2001 | Kugler et al. |
| 6,280,467 B1 | 8/2001 | Leonhardt |
| 6,285,903 B1 | 9/2001 | Rosenthal et al. |
| 6,287,315 B1 | 9/2001 | Wijeratne et al. |
| 6,302,906 B1 | 10/2001 | Goicoechea et al. |
| 6,302,907 B1 | 10/2001 | Hijlkema |
| 6,306,141 B1 | 10/2001 | Jervis |
| 6,312,458 B1 | 11/2001 | Golds |
| 6,319,275 B1 | 11/2001 | Lashinski et al. |
| 6,319,278 B1 | 11/2001 | Quinn |
| 6,322,585 B1 | 11/2001 | Khosravi et al. |
| 6,334,869 B1 | 1/2002 | Leonhardt et al. |
| 6,338,709 B1 | 1/2002 | Geoffrion et al. |
| 6,342,066 B1 | 1/2002 | Toro et al. |
| 6,344,044 B1 | 2/2002 | Fulkerson et al. |
| 6,344,052 B1 | 2/2002 | Greenan et al. |
| 6,346,118 B1 | 2/2002 | Baker et al. |
| 6,350,277 B1 | 2/2002 | Kocur |
| 6,350,278 B1 | 2/2002 | Lenker et al. |
| 6,355,056 B1 | 3/2002 | Pinheiro |
| 6,355,060 B1 | 3/2002 | Lenker et al. |
| 6,368,345 B1 | 4/2002 | Dehdashtian et al. |
| 6,375,675 B2 | 4/2002 | Dehdashtian et al. |
| 6,375,676 B1 | 4/2002 | Cox |
| 6,379,372 B1 | 4/2002 | Dehdashtian et al. |
| 6,389,946 B1 | 5/2002 | Frid |
| 6,395,017 B1 | 5/2002 | Dwyer et al. |
| 6,395,022 B1 | 5/2002 | Piplani et al. |
| 6,402,781 B1 | 6/2002 | Langberg et al. |
| 6,416,490 B1 | 7/2002 | Ellis et al. |
| 6,416,542 B1 | 7/2002 | Marcade et al. |
| 6,419,686 B1 | 7/2002 | McLeod et al. |
| 6,425,898 B1 | 7/2002 | Wilson et al. |
| 6,443,979 B1 | 9/2002 | Stalker et al. |
| 6,443,980 B1 | 9/2002 | Wang et al. |
| 6,450,988 B1 | 9/2002 | Bradshaw |
| 6,451,053 B1 | 9/2002 | Dehdashtian et al. |
| 6,454,796 B1 | 9/2002 | Barkman et al. |
| 6,458,867 B1 | 10/2002 | Wang et al. |
| 6,464,684 B1 | 10/2002 | Galdonik |
| 6,464,719 B2 | 10/2002 | Jayaraman |
| 6,464,721 B1 | 10/2002 | Marcade et al. |
| 6,478,818 B1 | 11/2002 | Taheri |
| 6,488,700 B2 | 12/2002 | Klumb et al. |
| 6,503,274 B1 | 1/2003 | Howanec, Jr. et al. |
| 6,505,066 B2 | 1/2003 | Berg et al. |
| 6,514,282 B1 | 2/2003 | Inoue |
| 6,517,571 B1 | 2/2003 | Brauker et al. |
| 6,517,572 B2 | 2/2003 | Kugler et al. |
| 6,517,573 B1 | 2/2003 | Pollock et al. |
| 6,520,951 B1 | 2/2003 | Carrillo, Jr. et al. |
| 6,520,986 B2 | 2/2003 | Martin et al. |
| 6,524,335 B1 | 2/2003 | Hartley et al. |
| 6,524,336 B1 | 2/2003 | Papazolgou et al. |
| 6,533,753 B1 | 3/2003 | Haarstad et al. |
| 6,540,698 B1 | 4/2003 | Ishii |
| 6,540,778 B1 | 4/2003 | Quiachon et al. |
| 6,551,350 B1 | 4/2003 | Thornton et al. |
| 6,562,022 B2 | 5/2003 | Hoste et al. |
| 6,565,596 B1 | 5/2003 | White et al. |
| 6,565,597 B1 | 5/2003 | Fearnot et al. |
| 6,575,994 B1 | 6/2003 | Marin et al. |
| 6,576,007 B2 | 6/2003 | Dehdashtian et al. |
| 6,582,458 B1 | 6/2003 | White et al. |
| 6,582,460 B1 | 6/2003 | Cryer |
| 6,592,526 B1 | 7/2003 | Lenker |
| 6,613,073 B1 | 9/2003 | White et al. |
| 6,616,626 B2 | 9/2003 | Crank et al. |
| 6,620,126 B2 | 9/2003 | Unsworth et al. |
| 6,641,606 B2 | 11/2003 | Ouriel et al. |
| 6,645,242 B1 | 11/2003 | Quinn |
| 6,652,571 B1 | 11/2003 | White et al. |
| 6,652,572 B2 | 11/2003 | Kugler et al. |
| 6,660,033 B1 | 12/2003 | Marcade et al. |
| 6,676,666 B2 | 1/2004 | Vrba et al. |
| 6,682,536 B2 | 1/2004 | Vardi et al. |
| 6,682,537 B2 | 1/2004 | Ouriel et al. |
| 6,682,557 B1 | 1/2004 | Quiachon et al. |
| 6,685,736 B1 | 2/2004 | White et al. |
| 6,689,152 B2 | 2/2004 | Balceta et al. |

(56) References Cited

U.S. PATENT DOCUMENTS

| | | |
|---|---|---|
| 6,689,158 B1 | 2/2004 | White et al. |
| 6,692,458 B2 | 2/2004 | Forman et al. |
| 6,692,483 B2 | 2/2004 | Vardi et al. |
| 6,692,512 B2 | 2/2004 | Jang |
| 6,695,875 B2 | 2/2004 | Stelter et al. |
| 6,706,033 B1 | 3/2004 | Martinez et al. |
| 6,726,712 B1 | 4/2004 | Raeder-Devens et al. |
| 6,733,519 B2 | 5/2004 | Lashinski et al. |
| 6,733,523 B2 | 5/2004 | Shaolian et al. |
| 6,755,856 B2 | 6/2004 | Fierens et al. |
| 6,761,731 B2 | 7/2004 | Majercak |
| 6,790,222 B2 | 9/2004 | Kugler et al. |
| 6,802,860 B2 | 10/2004 | Cosgrove et al. |
| 6,808,529 B2 | 10/2004 | Fulkerson |
| 6,811,559 B2 | 11/2004 | Thornton |
| 6,814,748 B1 | 11/2004 | Baker et al. |
| 6,821,291 B2 | 11/2004 | Bolea et al. |
| 6,827,710 B1 | 12/2004 | Mooney et al. |
| 6,827,711 B2 | 12/2004 | Sunseri |
| 6,830,575 B2 | 12/2004 | Stenzel et al. |
| 6,843,803 B2 | 1/2005 | Ryan et al. |
| 6,849,084 B2 | 2/2005 | Rabkin et al. |
| 6,849,088 B2 | 2/2005 | Dehdashtian et al. |
| 6,858,034 B1 | 2/2005 | Hijlkema et al. |
| 6,859,986 B2 | 3/2005 | Jackson et al. |
| 6,860,901 B1 | 3/2005 | Baker et al. |
| 6,863,668 B2 | 3/2005 | Gillespie et al. |
| 6,866,660 B2 | 3/2005 | Garabedian et al. |
| 6,866,669 B2 | 3/2005 | Buzzard et al. |
| 6,871,085 B2 | 3/2005 | Sommer |
| 6,884,260 B2 | 4/2005 | Kugler et al. |
| 6,890,348 B2 | 5/2005 | Sydney et al. |
| 6,911,039 B2 | 6/2005 | Shiu et al. |
| 6,916,335 B2 | 7/2005 | Kanji |
| 6,918,925 B2 | 7/2005 | Tehrani |
| 6,932,829 B2 | 8/2005 | Majercak |
| 6,938,646 B2 | 9/2005 | Litton |
| 6,939,371 B2 | 9/2005 | Kugler et al. |
| 6,942,691 B1 | 9/2005 | Chuter |
| 6,945,989 B1 | 9/2005 | Betelia et al. |
| 6,945,990 B2 | 9/2005 | Greenan |
| 6,964,679 B1 | 11/2005 | Marcade et al. |
| 6,984,244 B2 | 1/2006 | Perez et al. |
| 6,989,024 B2 | 1/2006 | Hebert et al. |
| 6,994,722 B2 | 2/2006 | DiCarlo |
| 7,001,420 B2 | 2/2006 | Speck et al. |
| 7,011,647 B2 | 3/2006 | Purdy et al. |
| 7,014,653 B2 | 3/2006 | Ouriel et al. |
| 7,025,773 B2 | 4/2006 | Gittings et al. |
| 7,052,511 B2 | 5/2006 | Weldon et al. |
| 7,070,582 B2 | 7/2006 | Freyman et al. |
| 7,105,016 B2 | 9/2006 | Shiu et al. |
| 7,112,217 B1 | 9/2006 | Kugler et al. |
| 7,115,134 B2 | 10/2006 | Chambers |
| 7,125,419 B2 | 10/2006 | Sequin et al. |
| 7,147,657 B2 | 12/2006 | Chiang et al. |
| 7,147,660 B2 | 12/2006 | Chobotov et al. |
| 7,160,318 B2 | 1/2007 | Greenberg et al. |
| 7,163,552 B2 | 1/2007 | Diaz |
| 7,166,125 B1 | 1/2007 | Baker et al. |
| 7,169,170 B2 | 1/2007 | Widenhouse |
| 7,195,639 B2 | 3/2007 | Quiachon et al. |
| 7,225,518 B2 | 6/2007 | Eidenschink et al. |
| 7,238,197 B2 | 7/2007 | Sequin et al. |
| 7,264,632 B2 | 9/2007 | Wright et al. |
| 7,294,147 B2 | 11/2007 | Hartley |
| 7,320,703 B2 | 1/2008 | DiMatteo et al. |
| 7,326,241 B2 | 2/2008 | Jang |
| 7,351,256 B2 | 4/2008 | Hojeibane et al. |
| 7,435,253 B1 | 10/2008 | Hartley et al. |
| 7,451,765 B2 | 11/2008 | Adler |
| 7,530,995 B2 | 5/2009 | Quijano et al. |
| 7,691,090 B2 | 4/2010 | Belley et al. |
| 7,708,771 B2 | 5/2010 | Chuter et al. |
| 7,717,950 B2 | 5/2010 | Greenan |
| 7,722,663 B1 | 5/2010 | Austin |
| 7,763,063 B2 | 7/2010 | Arbefeuille et al. |
| 7,766,962 B1 | 8/2010 | Quinn |
| 7,780,716 B2 | 8/2010 | Pappas et al. |
| 7,794,489 B2 | 9/2010 | Shumer et al. |
| 7,799,065 B2 | 9/2010 | Pappas |
| 7,837,724 B2 | 11/2010 | Keeble et al. |
| 8,007,605 B2 | 8/2011 | Arbefeuille et al. |
| 8,043,354 B2 | 10/2011 | Greenberg et al. |
| 8,062,345 B2 | 11/2011 | Ouellette et al. |
| 8,062,349 B2 | 11/2011 | Moore et al. |
| 8,070,790 B2 | 12/2011 | Berra et al. |
| 8,083,792 B2 | 12/2011 | Boucher et al. |
| 8,137,321 B2 | 3/2012 | Argentine |
| 8,206,427 B1 | 6/2012 | Ryan et al. |
| 8,241,346 B2 | 8/2012 | Chobotov |
| 8,292,943 B2 | 10/2012 | Berra et al. |
| 8,308,790 B2 | 11/2012 | Arbefeuille et al. |
| 8,317,854 B1 | 11/2012 | Ryan et al. |
| 8,333,797 B2 | 12/2012 | Goodson, IV et al. |
| 8,348,988 B2 | 1/2013 | Lad et al. |
| 8,449,595 B2 | 5/2013 | Ouellette et al. |
| 8,500,792 B2 | 8/2013 | Berra |
| 8,579,963 B2 | 11/2013 | Tabor |
| 8,636,788 B2 | 1/2014 | Arbefeuille et al. |
| 8,672,992 B2 | 3/2014 | Orr |
| 8,702,787 B2 | 4/2014 | Arbefeuille |
| 8,709,060 B2 | 4/2014 | Osborne |
| 8,734,501 B2 | 5/2014 | Hartley et al. |
| 8,740,963 B2 | 6/2014 | Arbefeuille et al. |
| 8,998,970 B2 | 4/2015 | Arbefeuille et al. |
| 9,101,506 B2 | 8/2015 | Arbefeuille et al. |
| 9,173,755 B2 | 11/2015 | Berra et al. |
| 9,198,786 B2 | 12/2015 | Moore et al. |
| 9,220,617 B2 | 12/2015 | Berra |
| 9,237,960 B2 | 1/2016 | Rasmussen et al. |
| 9,320,631 B2 | 4/2016 | Moore et al. |
| 9,333,104 B2 | 5/2016 | Ouellette et al. |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 * | 9/2016 | White .................. A61F 2/07 |
| 9,554,929 B2 | 1/2017 | Arbefeuille et al. |
| 9,561,124 B2 | 2/2017 | Arbefeuille et al. |
| 9,592,112 B2 | 3/2017 | Arbefeuille et al. |
| 9,655,712 B2 | 5/2017 | Berra et al. |
| 9,827,123 B2 | 11/2017 | Arbefeuille et al. |
| 9,877,857 B2 | 1/2018 | Arbefeuille et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 10,105,248 B2 | 10/2018 | Berra et al. |
| 10,292,850 B2 | 5/2019 | Vad et al. |
| 10,299,951 B2 | 5/2019 | Arbefeuille et al. |
| 10,307,275 B2 | 6/2019 | Berra et al. |
| 10,390,929 B2 | 8/2019 | Arbefeuille et al. |
| 10,555,826 B2 * | 2/2020 | White .................. A61F 2/07 |
| 10,646,365 B2 | 5/2020 | Berra et al. |
| 10,864,097 B2 | 12/2020 | Berra et al. |
| 10,945,827 B2 | 3/2021 | Berra et al. |
| 11,259,945 B2 | 3/2022 | Berra |
| 11,351,049 B2 | 6/2022 | Arbefeuille et al. |
| 11,382,779 B2 | 7/2022 | Berra et al. |
| 11,413,173 B2 | 8/2022 | Arbefeuille et al. |
| 2001/0000801 A1 | 5/2001 | Miller et al. |
| 2001/0001833 A1 | 5/2001 | Ravenscroft et al. |
| 2001/0034549 A1 | 10/2001 | Bartholf et al. |
| 2001/0049547 A1 | 12/2001 | Moore |
| 2002/0007193 A1 | 1/2002 | Tanner et al. |
| 2002/0013617 A1 | 1/2002 | Matsutani et al. |
| 2002/0016597 A1 | 2/2002 | Dwyer et al. |
| 2002/0016627 A1 | 2/2002 | Golds |
| 2002/0035394 A1 | 3/2002 | Fierens et al. |
| 2002/0045929 A1 | 4/2002 | Diaz |
| 2002/0052643 A1 | 5/2002 | Wholey et al. |
| 2002/0052660 A1 | 5/2002 | Greenhalgh |
| 2002/0062133 A1 | 5/2002 | Gilson et al. |
| 2002/0072755 A1 | 6/2002 | Bigus et al. |
| 2002/0082523 A1 | 6/2002 | Kinsella et al. |

(56) References Cited

U.S. PATENT DOCUMENTS

| | | |
|---|---|---|
| 2002/0082674 A1 | 6/2002 | Anson et al. |
| 2002/0091439 A1 | 7/2002 | Baker et al. |
| 2002/0095140 A1 | 7/2002 | Lootz et al. |
| 2002/0107561 A1 | 8/2002 | Pinheiro |
| 2002/0108621 A1 | 8/2002 | Berg et al. |
| 2002/0111671 A1 | 8/2002 | Stenzel |
| 2002/0138133 A1 | 9/2002 | Lenz et al. |
| 2002/0156518 A1 | 10/2002 | Tehrani |
| 2002/0156522 A1 | 10/2002 | Ivancev et al. |
| 2002/0161424 A1 | 10/2002 | Rapacki et al. |
| 2002/0165554 A1 | 11/2002 | Dworschak et al. |
| 2002/0188344 A1 | 12/2002 | Bolea |
| 2002/0198587 A1 | 12/2002 | Greenberg et al. |
| 2003/0028237 A1 | 2/2003 | Sullivan et al. |
| 2003/0074049 A1 | 4/2003 | Hoganson et al. |
| 2003/0083734 A1 | 5/2003 | Friedrich et al. |
| 2003/0088305 A1 | 5/2003 | Van Schie et al. |
| 2003/0114910 A1 | 6/2003 | Juhani Laakso et al. |
| 2003/0120263 A1 | 6/2003 | Ouriel et al. |
| 2003/0120333 A1 | 6/2003 | Ouriel et al. |
| 2003/0135259 A1 | 7/2003 | Simso |
| 2003/0135269 A1 | 7/2003 | Strom |
| 2003/0139803 A1 | 7/2003 | Sequin et al. |
| 2003/0163193 A1 | 8/2003 | Widenhouse |
| 2003/0167060 A1 | 9/2003 | Buzzard |
| 2003/0176911 A1 | 9/2003 | Iancea et al. |
| 2003/0176912 A1 | 9/2003 | Chuter et al. |
| 2003/0191516 A1 | 10/2003 | Weldon et al. |
| 2003/0195607 A1 | 10/2003 | Trout et al. |
| 2003/0195614 A1 | 10/2003 | Ryan et al. |
| 2003/0199966 A1 | 10/2003 | Shiu et al. |
| 2003/0199967 A1 | 10/2003 | Hartley et al. |
| 2003/0199973 A1 | 10/2003 | Chuter et al. |
| 2003/0212431 A1 | 11/2003 | Brady et al. |
| 2003/0220682 A1 | 11/2003 | Kujawski |
| 2003/0225445 A1 | 12/2003 | Derus et al. |
| 2003/0233140 A1 | 12/2003 | Hartley et al. |
| 2003/0236564 A1 | 12/2003 | Majercak |
| 2003/0236565 A1 | 12/2003 | DiMatteo et al. |
| 2004/0073284 A1 | 4/2004 | Bates et al. |
| 2004/0073289 A1 | 4/2004 | Hartley |
| 2004/0093063 A1 | 5/2004 | Wright et al. |
| 2004/0098084 A1 | 5/2004 | Hartley et al. |
| 2004/0106974 A1 | 6/2004 | Greenberg et al. |
| 2004/0117003 A1 | 6/2004 | Ouriel et al. |
| 2004/0148007 A1 | 7/2004 | Jackson et al. |
| 2004/0148009 A1 | 7/2004 | Buzzard et al. |
| 2004/0193141 A1 | 9/2004 | Leopold et al. |
| 2004/0193244 A1 | 9/2004 | Hartley et al. |
| 2004/0193245 A1 | 9/2004 | Deem et al. |
| 2004/0193252 A1 | 9/2004 | Perez et al. |
| 2004/0199240 A1 | 10/2004 | Dorn et al. |
| 2004/0210194 A1 | 10/2004 | Bonnette et al. |
| 2004/0230284 A1 | 11/2004 | Headley et al. |
| 2004/0230286 A1 | 11/2004 | Moore et al. |
| 2004/0230384 A1 | 11/2004 | Haynes et al. |
| 2004/0236403 A1 | 11/2004 | Leonhardt et al. |
| 2004/0236407 A1 | 11/2004 | Fierens et al. |
| 2004/0267281 A1 | 12/2004 | Harari et al. |
| 2005/0021125 A1 | 1/2005 | Stack et al. |
| 2005/0027305 A1 | 2/2005 | Shiu et al. |
| 2005/0033406 A1 | 2/2005 | Barnhart et al. |
| 2005/0038495 A1 | 2/2005 | Greenan |
| 2005/0049667 A1 | 3/2005 | Arbefeuille et al. |
| 2005/0049674 A1 | 3/2005 | Berra et al. |
| 2005/0060016 A1 | 3/2005 | Wu et al. |
| 2005/0080476 A1 | 4/2005 | Gunderson et al. |
| 2005/0080477 A1 | 4/2005 | Sydney et al. |
| 2005/0085789 A1 | 4/2005 | Khan et al. |
| 2005/0096726 A1 | 5/2005 | Sequin et al. |
| 2005/0107862 A1 | 5/2005 | Ohlenschlaeger |
| 2005/0131523 A1 | 6/2005 | Bashiri et al. |
| 2005/0149166 A1 | 7/2005 | Schaeffer et al. |
| 2005/0159803 A1 | 7/2005 | Lad et al. |
| 2005/0159804 A1 | 7/2005 | Lad et al. |
| 2005/0171597 A1 | 8/2005 | Boatman et al. |
| 2005/0171598 A1 | 8/2005 | Schaeffer |
| 2005/0177222 A1 | 8/2005 | Mead |
| 2005/0183259 A1 | 8/2005 | Eidenschink et al. |
| 2005/0192659 A1 | 9/2005 | Dahl et al. |
| 2005/0222668 A1 | 10/2005 | Schaeffer et al. |
| 2005/0228484 A1 | 10/2005 | Stephens et al. |
| 2005/0283223 A1 | 12/2005 | Greenan |
| 2005/0288764 A1 | 12/2005 | Snow et al. |
| 2005/0288766 A1 | 12/2005 | Plain et al. |
| 2006/0004433 A1 | 1/2006 | Greenberg et al. |
| 2006/0020319 A1 | 1/2006 | Kim et al. |
| 2006/0020320 A1 | 1/2006 | Shaolian et al. |
| 2006/0058864 A1 | 3/2006 | Schaeffer et al. |
| 2006/0127439 A1 | 6/2006 | Mattes et al. |
| 2006/0129169 A1 | 6/2006 | Fogarty et al. |
| 2006/0129224 A1 | 6/2006 | Arbefeuille et al. |
| 2006/0135961 A1 | 6/2006 | Rosenman et al. |
| 2006/0155358 A1 | 7/2006 | LaDuca et al. |
| 2006/0155366 A1 | 7/2006 | LaDuca et al. |
| 2006/0178726 A1 | 8/2006 | Douglas |
| 2006/0178733 A1 | 8/2006 | Pinchuk et al. |
| 2006/0188408 A1 | 8/2006 | Arbefeuille et al. |
| 2006/0195172 A1 | 8/2006 | Luo et al. |
| 2006/0200110 A1 | 9/2006 | Lentz et al. |
| 2006/0212105 A1 | 9/2006 | Dorn et al. |
| 2006/0265047 A1 | 11/2006 | Dorn |
| 2006/0276872 A1 | 12/2006 | Arbefeuille et al. |
| 2006/0282150 A1 | 12/2006 | Olson et al. |
| 2007/0021822 A1 | 1/2007 | Boatman |
| 2007/0048348 A1 | 3/2007 | Atanasoska et al. |
| 2007/0053952 A1 | 3/2007 | Chen et al. |
| 2007/0055338 A1 | 3/2007 | Dorn |
| 2007/0055340 A1 | 3/2007 | Pryor |
| 2007/0055341 A1 | 3/2007 | Edoga et al. |
| 2007/0055345 A1 | 3/2007 | Arbefeuille |
| 2007/0055347 A1 | 3/2007 | Arbefeuille |
| 2007/0083252 A1 | 4/2007 | McDonald |
| 2007/0100422 A1 | 5/2007 | Shumer et al. |
| 2007/0100425 A1 | 5/2007 | Sequin et al. |
| 2007/0123972 A1 | 5/2007 | Greenberg et al. |
| 2007/0135818 A1 | 6/2007 | Moore et al. |
| 2007/0135889 A1 | 6/2007 | Moore et al. |
| 2007/0142894 A1 | 6/2007 | Moore et al. |
| 2007/0156223 A1 | 7/2007 | Vaughan |
| 2007/0156228 A1 | 7/2007 | Majercak et al. |
| 2007/0162109 A1 | 7/2007 | Davila et al. |
| 2007/0163668 A1 | 7/2007 | Arbefeuille et al. |
| 2007/0168014 A1 | 7/2007 | Jimenez et al. |
| 2007/0173929 A1 | 7/2007 | Boucher et al. |
| 2007/0179592 A1 | 8/2007 | Schaeffer |
| 2007/0179593 A1 | 8/2007 | Fierens et al. |
| 2007/0179601 A1 | 8/2007 | Fierens et al. |
| 2007/0198078 A1 | 8/2007 | Berra et al. |
| 2007/0203566 A1 | 8/2007 | Arbefeuille et al. |
| 2007/0207186 A1 | 9/2007 | Scanlon et al. |
| 2007/0213800 A1 | 9/2007 | Fierens et al. |
| 2007/0219620 A1 | 9/2007 | Eells et al. |
| 2007/0244545 A1 | 10/2007 | Birdsall et al. |
| 2008/0021538 A1 | 1/2008 | Wright et al. |
| 2008/0027528 A1 | 1/2008 | Jagger et al. |
| 2008/0046065 A1 | 2/2008 | Hartley et al. |
| 2008/0065011 A1 | 3/2008 | Marchand et al. |
| 2008/0071343 A1 | 3/2008 | Mayberry et al. |
| 2008/0077226 A1 | 3/2008 | Ouellette et al. |
| 2008/0077227 A1 | 3/2008 | Ouellette et al. |
| 2008/0082158 A1 | 4/2008 | Tseng et al. |
| 2008/0091260 A1 | 4/2008 | Pomeranz et al. |
| 2008/0114441 A1 | 5/2008 | Rust et al. |
| 2008/0132996 A1 | 6/2008 | Drasler et al. |
| 2008/0157017 A1 | 7/2008 | Macatangay et al. |
| 2008/0172122 A1 | 7/2008 | Mayberry et al. |
| 2008/0195191 A1 | 8/2008 | Luo et al. |
| 2008/0208175 A1 | 8/2008 | Beckman et al. |
| 2008/0262590 A1 | 10/2008 | Murray |
| 2008/0264102 A1 | 10/2008 | Berra |
| 2008/0269865 A1 | 10/2008 | Snow et al. |
| 2009/0163951 A1 | 6/2009 | Simmons et al. |
| 2009/0254165 A1 | 10/2009 | Tabor et al. |

(56) References Cited

U.S. PATENT DOCUMENTS

| | | |
|---|---|---|
| 2010/0004730 A1 | 1/2010 | Benjamin et al. |
| 2010/0030255 A1* | 2/2010 | Berra ............... A61M 39/06 606/200 |
| 2010/0030318 A1 | 2/2010 | Berra |
| 2010/0049313 A1 | 2/2010 | Alon et al. |
| 2010/0234932 A1 | 9/2010 | Arbefeuille et al. |
| 2010/0274226 A1 | 10/2010 | Hansen |
| 2010/0274340 A1 | 10/2010 | Hartley et al. |
| 2011/0054405 A1 | 3/2011 | Whiting et al. |
| 2011/0071614 A1 | 3/2011 | Majercak et al. |
| 2011/0087318 A1 | 4/2011 | Daugherty et al. |
| 2011/0208288 A1 | 8/2011 | Arbefeuille et al. |
| 2011/0218607 A1 | 9/2011 | Arbefeuille et al. |
| 2011/0251664 A1 | 10/2011 | Acosta de Acevedo |
| 2011/0307049 A1 | 12/2011 | Kao |
| 2011/0313503 A1 | 12/2011 | Berra et al. |
| 2012/0022636 A1 | 1/2012 | Chobotov |
| 2012/0123517 A1 | 5/2012 | Ouellette et al. |
| 2012/0123528 A1 | 5/2012 | Knippel et al. |
| 2012/0130354 A1 | 5/2012 | Valaie |
| 2012/0143305 A1 | 6/2012 | Berra et al. |
| 2012/0245672 A1 | 9/2012 | Arbefeuille et al. |
| 2012/0271408 A1 | 10/2012 | Colgan et al. |
| 2012/0296413 A1 | 11/2012 | Arbefeuille et al. |
| 2013/0274856 A1 | 10/2013 | Arbefeuille et al. |
| 2013/0289693 A1 | 10/2013 | Maggard et al. |
| 2013/0325099 A1 | 12/2013 | Berra |
| 2013/0331924 A1 | 12/2013 | Ouellette et al. |
| 2014/0039597 A9 | 2/2014 | Arbefeuille et al. |
| 2014/0046428 A1 | 2/2014 | Cragg et al. |
| 2014/0135890 A9 | 5/2014 | Berra |
| 2014/0135892 A1 | 5/2014 | Arbefeuille et al. |
| 2014/0135896 A1 | 5/2014 | Arbefeuille et al. |
| 2014/0148890 A9 | 5/2014 | Ouellette et al. |
| 2014/0243952 A1 | 8/2014 | Parodi |
| 2014/0277340 A1 | 9/2014 | White et al. |
| 2014/0288627 A1 | 9/2014 | Ouellette et al. |
| 2014/0316510 A1 | 10/2014 | Berra |
| 2015/0173922 A1 | 6/2015 | Arbefeuille et al. |
| 2015/0202066 A1 | 7/2015 | Berra et al. |
| 2015/0202068 A1 | 7/2015 | Arbefeuille et al. |
| 2015/0272755 A1 | 10/2015 | Arbefeuille et al. |
| 2016/0045350 A1 | 2/2016 | Berra |
| 2016/0081787 A1 | 3/2016 | Parodi et al. |
| 2016/0135961 A1 | 5/2016 | Aeschlimann et al. |
| 2016/0270901 A1 | 9/2016 | Berra et al. |
| 2016/0270936 A1 | 9/2016 | Berra et al. |
| 2016/0310301 A1 | 10/2016 | Moore et al. |
| 2016/0338867 A1 | 11/2016 | White et al. |
| 2017/0000600 A1 | 1/2017 | Berra et al. |
| 2017/0100232 A1 | 4/2017 | Arbefeuille et al. |
| 2017/0100271 A1 | 4/2017 | Arbefeuille et al. |
| 2017/0135807 A1 | 5/2017 | Arbefeuille et al. |
| 2017/0151076 A9 | 6/2017 | Arbefeuille et al. |
| 2017/0165090 A1 | 6/2017 | Arbefeuille et al. |
| 2017/0165091 A1 | 6/2017 | Arbefeuille et al. |
| 2017/0281332 A1 | 10/2017 | Lostetter |
| 2017/0281382 A1 | 10/2017 | Lostetter et al. |
| 2017/0340433 A1 | 11/2017 | Berra et al. |
| 2017/0340462 A1 | 11/2017 | Lostetter |
| 2018/0014954 A1 | 1/2018 | Bradway |
| 2018/0049892 A1 | 2/2018 | Henkes et al. |
| 2018/0110638 A1 | 4/2018 | Berra et al. |
| 2018/0140448 A1 | 5/2018 | Arbefeuille et al. |
| 2018/0206972 A1 | 7/2018 | Arbefeuille et al. |
| 2019/0159914 A1 | 5/2019 | Berra et al. |
| 2019/0167412 A1 | 6/2019 | Berra et al. |
| 2020/0121483 A1 | 4/2020 | White et al. |
| 2020/0246168 A1 | 8/2020 | Berra et al. |
| 2020/0345527 A1 | 11/2020 | Berra et al. |
| 2021/0401602 A1 | 12/2021 | Vancheri |
| 2022/0257398 A1 | 8/2022 | Arbefeuille et al. |

FOREIGN PATENT DOCUMENTS

| | | |
|---|---|---|
| DE | 19753123 A1 | 8/1999 |
| DE | 102006053748 B3 | 4/2008 |
| EP | 0510851 A1 | 10/1992 |
| EP | 0873733 A1 | 10/1998 |
| EP | 0960607 A1 | 12/1999 |
| EP | 0696447 B1 | 1/2000 |
| EP | 0990426 A1 | 4/2000 |
| EP | 1177779 A2 | 2/2002 |
| EP | 1302178 A2 | 4/2003 |
| EP | 1358903 A2 | 11/2003 |
| EP | 1369098 A1 | 12/2003 |
| EP | 1440673 A1 | 7/2004 |
| EP | 1522277 A2 | 4/2005 |
| EP | 1772120 A2 | 4/2007 |
| EP | 1803423 A2 | 7/2007 |
| EP | 1923024 A2 | 5/2008 |
| EP | 1929979 A2 | 6/2008 |
| EP | 1982677 A2 | 10/2008 |
| EP | 1508313 B1 | 12/2008 |
| FR | 2714816 A1 | 7/1995 |
| FR | 2722678 A1 | 1/1996 |
| FR | 2779939 A1 | 12/1999 |
| FR | 2932979 A1 | 1/2010 |
| WO | WO-91/12838 A1 | 9/1991 |
| WO | WO-94/01149 A1 | 1/1994 |
| WO | WO-95/23008 A1 | 8/1995 |
| WO | WO-96/09013 A1 | 3/1996 |
| WO | WO-96/23455 A1 | 8/1996 |
| WO | WO-96/31174 A1 | 10/1996 |
| WO | WO-96/38101 A1 | 12/1996 |
| WO | WO-97/10778 A1 | 3/1997 |
| WO | WO-97/33532 A2 | 9/1997 |
| WO | WO-98/20811 A1 | 5/1998 |
| WO | WO-98/23242 A2 | 6/1998 |
| WO | WO-98/42276 A1 | 10/1998 |
| WO | WO-98/53761 A1 | 12/1998 |
| WO | WO-99/07308 A1 | 2/1999 |
| WO | WO-99/25273 A1 | 5/1999 |
| WO | WO-99/37242 A1 | 7/1999 |
| WO | WO-99/65420 A1 | 12/1999 |
| WO | WO-00/02615 A1 | 1/2000 |
| WO | WO-00/30562 A1 | 6/2000 |
| WO | WO-00/78248 A1 | 12/2000 |
| WO | WO-01/17602 A1 | 3/2001 |
| WO | WO-01/21102 A1 | 3/2001 |
| WO | WO-02/28316 A2 | 4/2002 |
| WO | WO-03/015662 A1 | 2/2003 |
| WO | WO-2004/000169 A1 | 12/2003 |
| WO | WO-2004/002370 A1 | 1/2004 |
| WO | WO-2004/071352 A1 | 8/2004 |
| WO | WO-2004091452 A1 | 10/2004 |
| WO | WO-2005/023149 A2 | 3/2005 |
| WO | WO-2005/034808 A1 | 4/2005 |
| WO | WO-2005/058409 A1 | 6/2005 |
| WO | WO-2005/067819 A1 | 7/2005 |
| WO | WO-2005/081936 A2 | 9/2005 |
| WO | WO-2005/112821 A2 | 12/2005 |
| WO | WO-2006/019551 A1 | 2/2006 |
| WO | WO-2006/088638 A1 | 8/2006 |
| WO | WO-2006/125382 A1 | 11/2006 |
| WO | WO-2007/008533 A1 | 1/2007 |
| WO | WO-2007/028086 A2 | 3/2007 |
| WO | WO-2007076114 A2 | 7/2007 |
| WO | WO-2007/092276 A2 | 8/2007 |
| WO | WO-2007/123956 A2 | 11/2007 |
| WO | WO-2008/031103 A2 | 3/2008 |
| WO | WO-2008/066923 A1 | 6/2008 |
| WO | WO-2008/085772 A1 | 7/2008 |
| WO | WO-2008/098252 A2 | 8/2008 |
| WO | WO-2009/023221 A1 | 2/2009 |
| WO | WO-2009/124124 A1 | 10/2009 |
| WO | WO-2010/005524 A2 | 1/2010 |
| WO | WO-2010/027485 A1 | 3/2010 |
| WO | WO-2010/042950 A2 | 4/2010 |
| WO | WO-2010/105195 A2 | 9/2010 |
| WO | WO-2011/056638 A1 | 5/2011 |
| WO | WO-2011/146649 A1 | 11/2011 |

(56) References Cited

FOREIGN PATENT DOCUMENTS

| WO | WO-2013/154749 A1 | 10/2013 |
| WO | WO-2014/149022 A1 | 9/2014 |
| WO | WO-2017/176674 A1 | 10/2017 |

OTHER PUBLICATIONS

Notice of Allowance for U.S. Appl. No. 13/834,808 dated Jul. 1, 2016.
U.S. Office Action for U.S. Appl. No. 12/459,387 dated Apr. 19, 2016.
U.S. Office Action for U.S. Appl. No. 12/459,387 dated Aug. 14, 2014.
U.S. Office Action for U.S. Appl. No. 12/459,387 dated Jan. 6, 2014.
U.S. Office Action for U.S. Appl. No. 12/459,387 dated Oct. 30, 2015.
U.S. Office Action for U.S. Appl. No. 12/459,387, dated Jul. 11, 2012.
U.S. Office Action for U.S. Appl. No. 12/459,387, dated Mar. 14, 2013.
U.S. Office Action for U.S. Appl. No. 12/459,387, dated May 8, 2012.
U.S. Office Action for U.S. Appl. No. 13/834,808 dated Sep. 18, 2015.
U.S. Office Action for U.S. Appl. No. 15/167,055 dated Jan. 11, 2017.
U.S. Office Action for U.S. Appl. No. 15/167,055 dated Jul. 12, 2017.
Criado "EVAR at 20: The Unfolding of a Revolutionary New Technique That Changed Everything," J. Endovasc. Ther., 17:789-796 (2010).
International Preliminary Report on Patentability for International Application No. PCT/US2013/032396 dated Sep. 24, 2015.
International Search Report and the Written Opinion for International Application No. PCT/US2013/032396 dated Jun. 20, 2014.
Parodi et al., "Transfemoral Intraluminal Graft Implantation for Abdominal Aortic Aneurysms," Ann. Vasc. Surg., 5:491-499 (1991).

\* cited by examiner

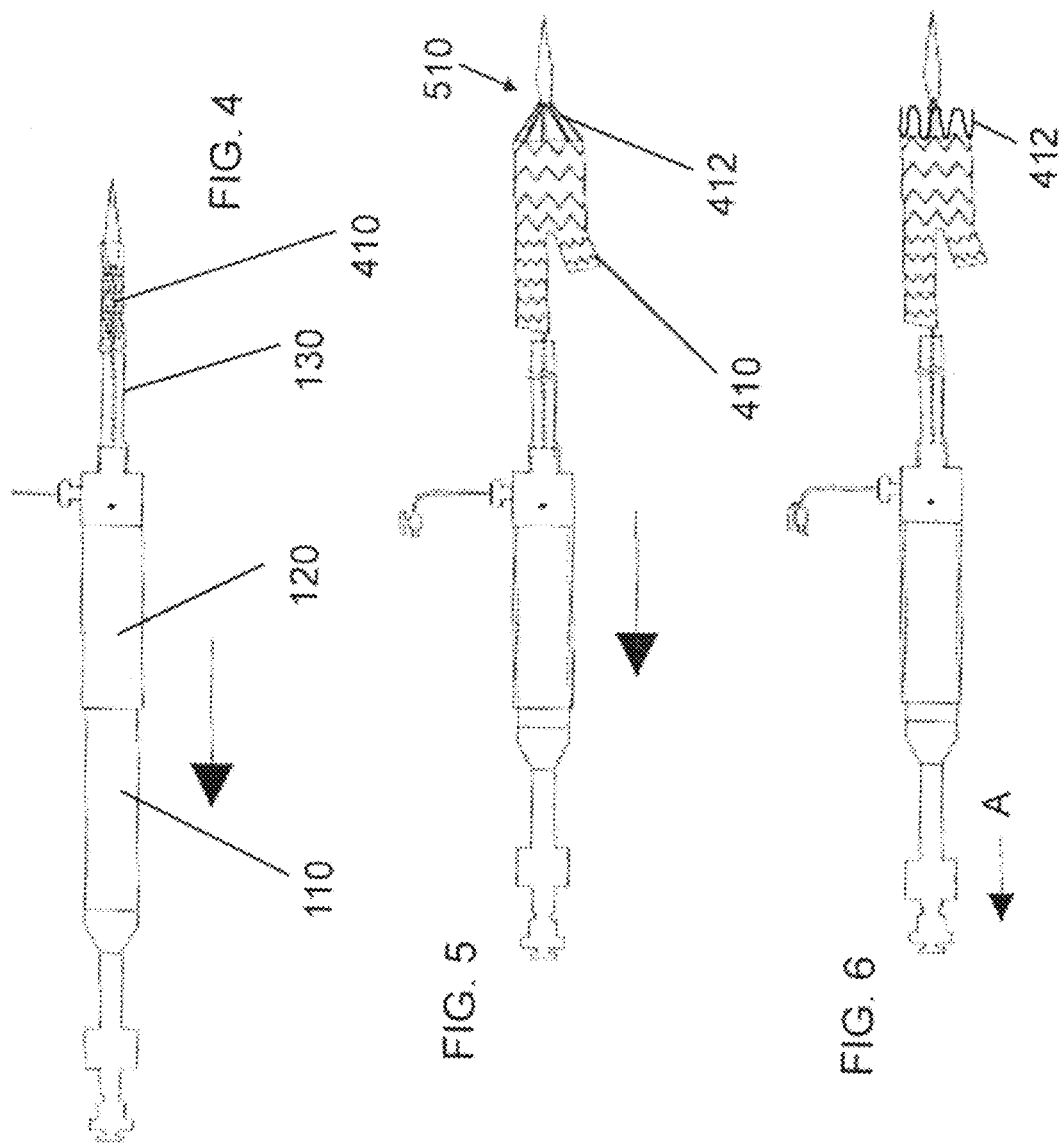

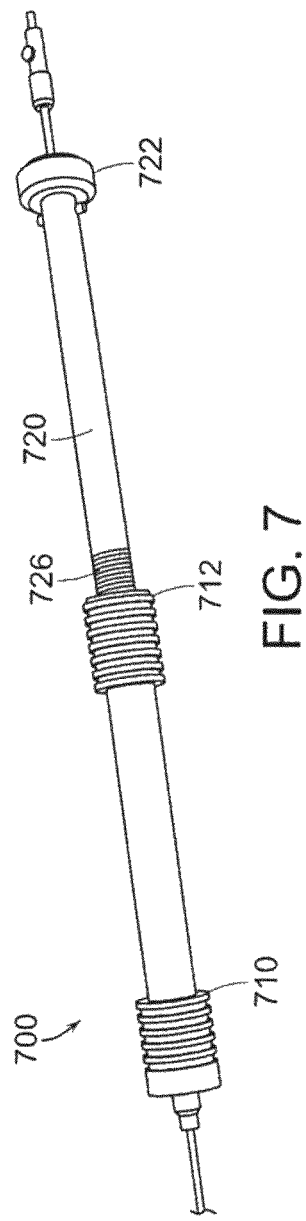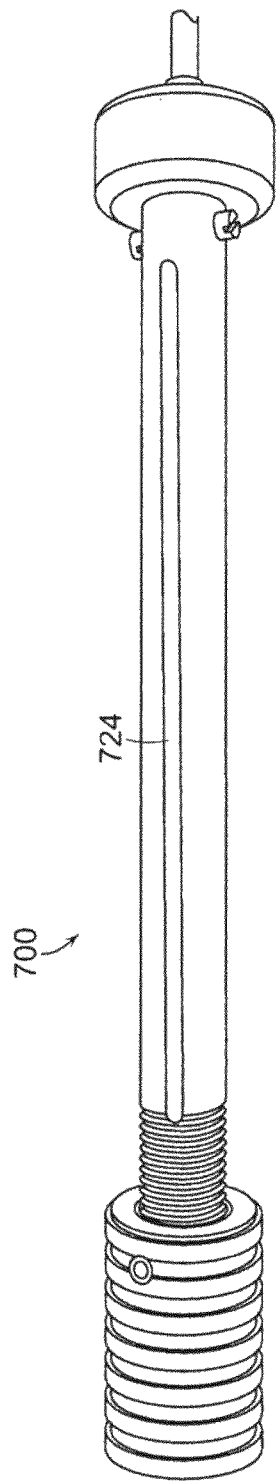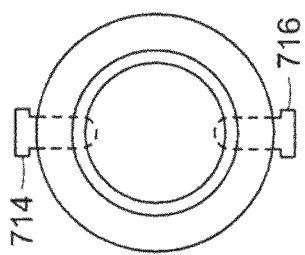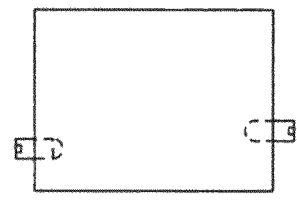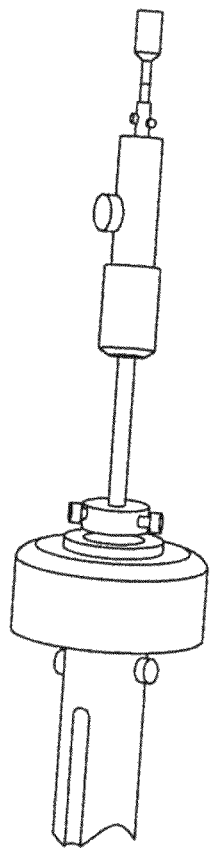
FIG. 7
FIG. 8
FIG. 11
FIG. 10
FIG. 9

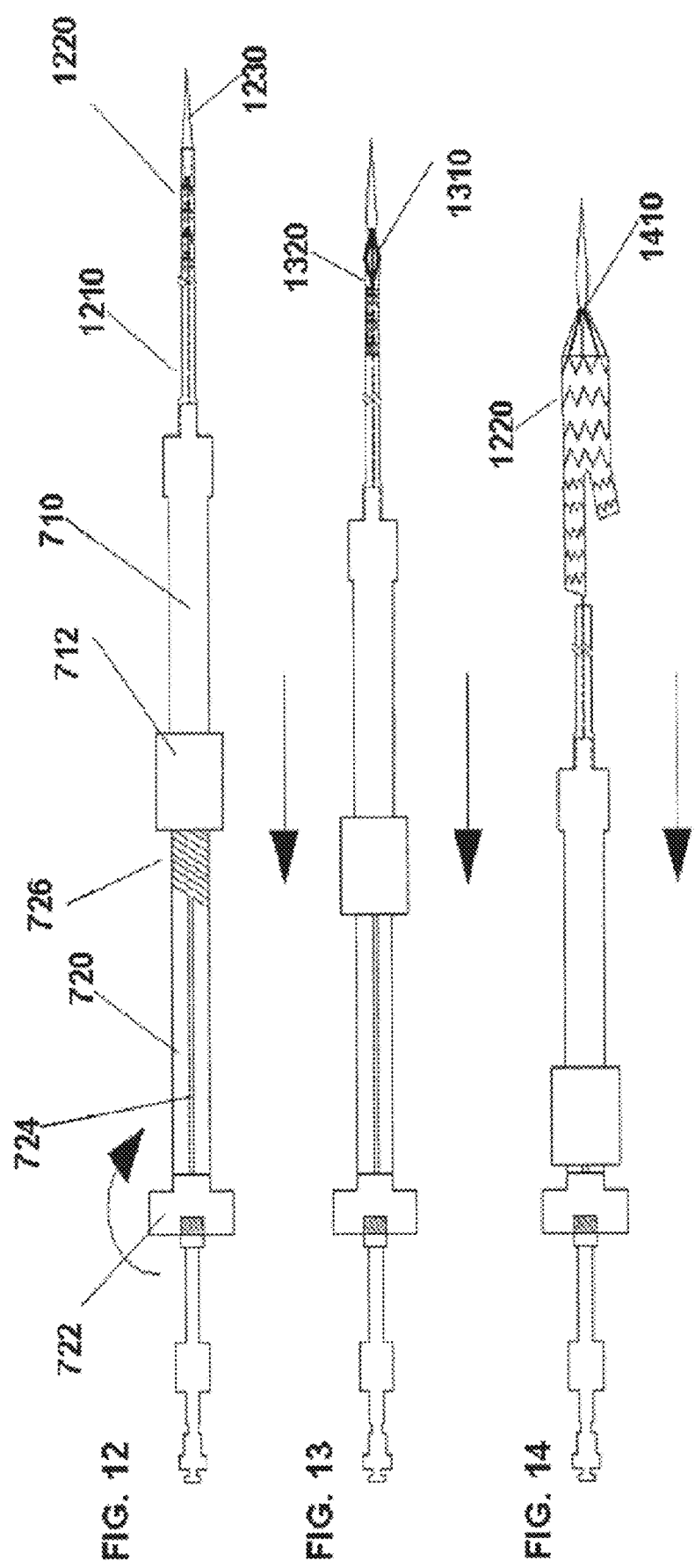

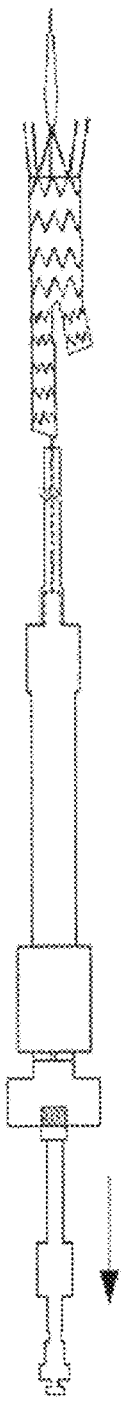
FIG. 15A
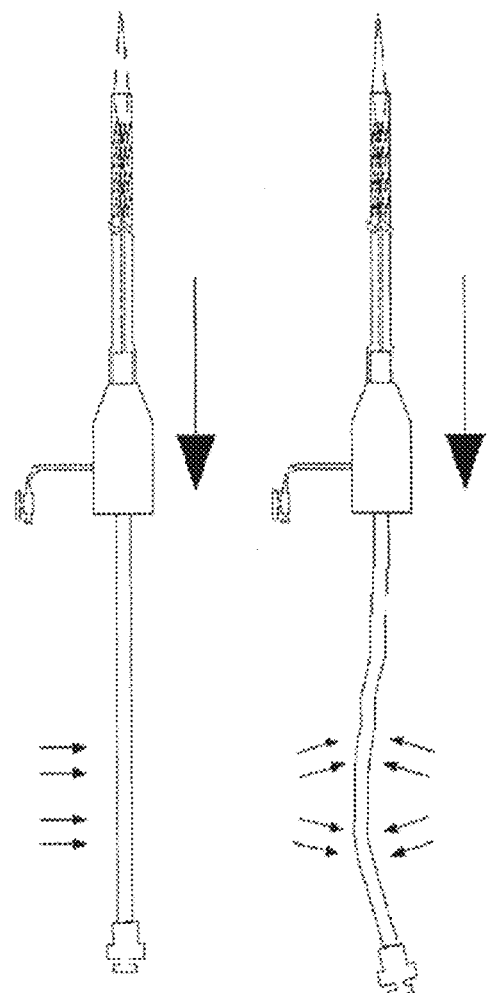
FIG. 15B
FIG. 15C
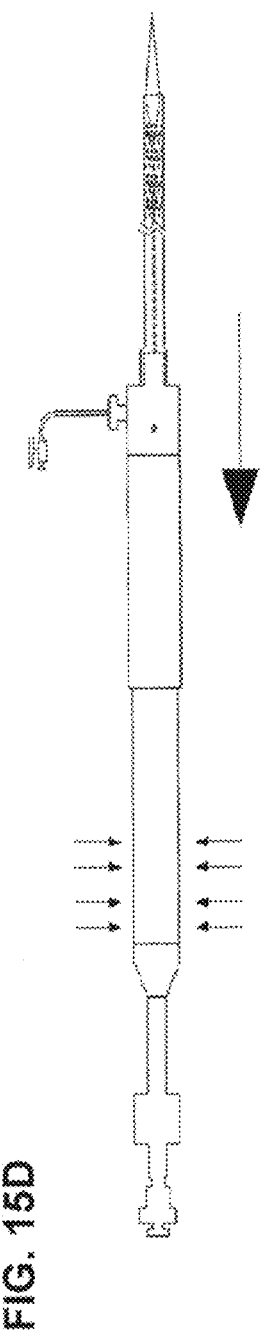
FIG. 15D

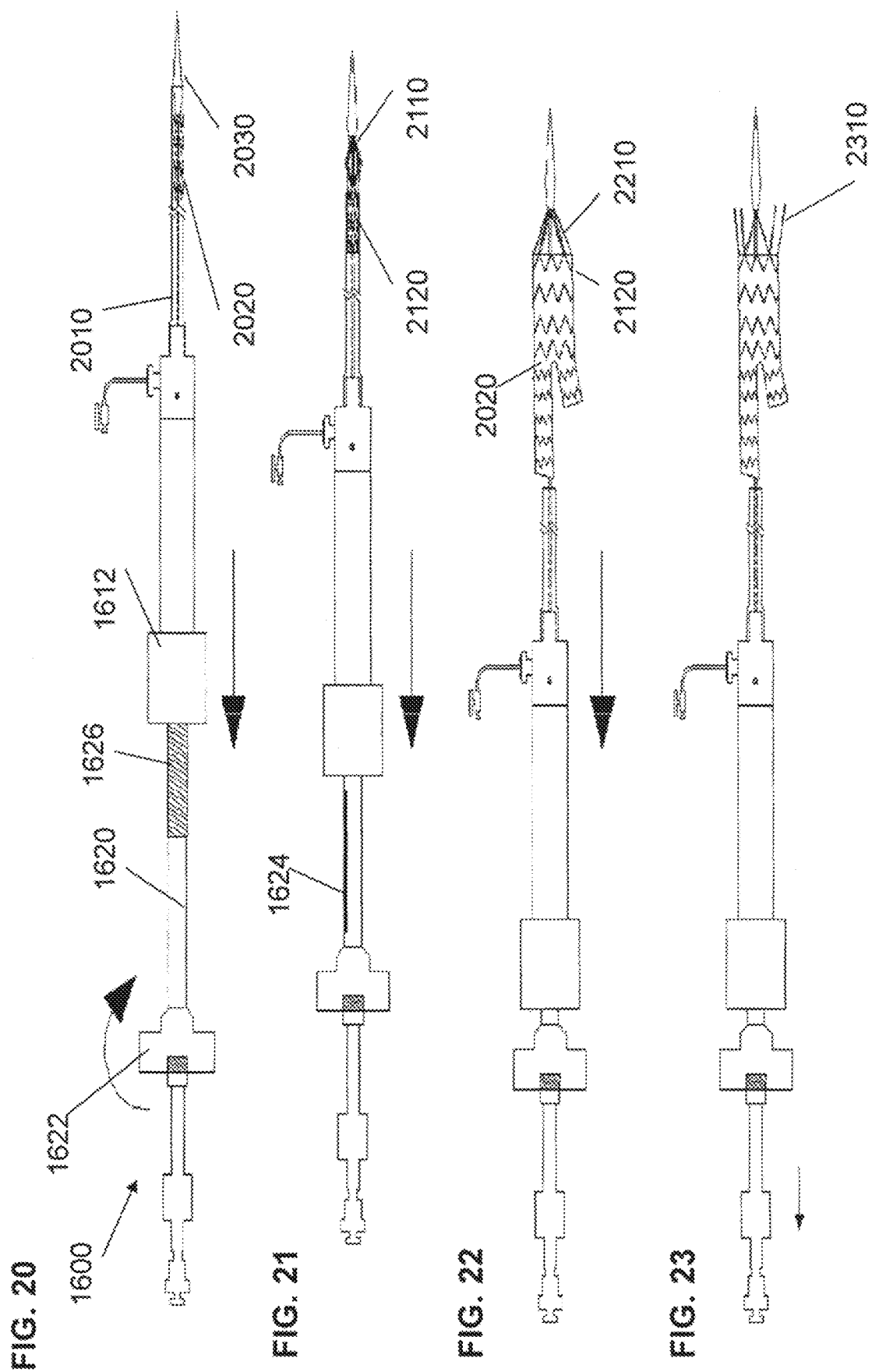

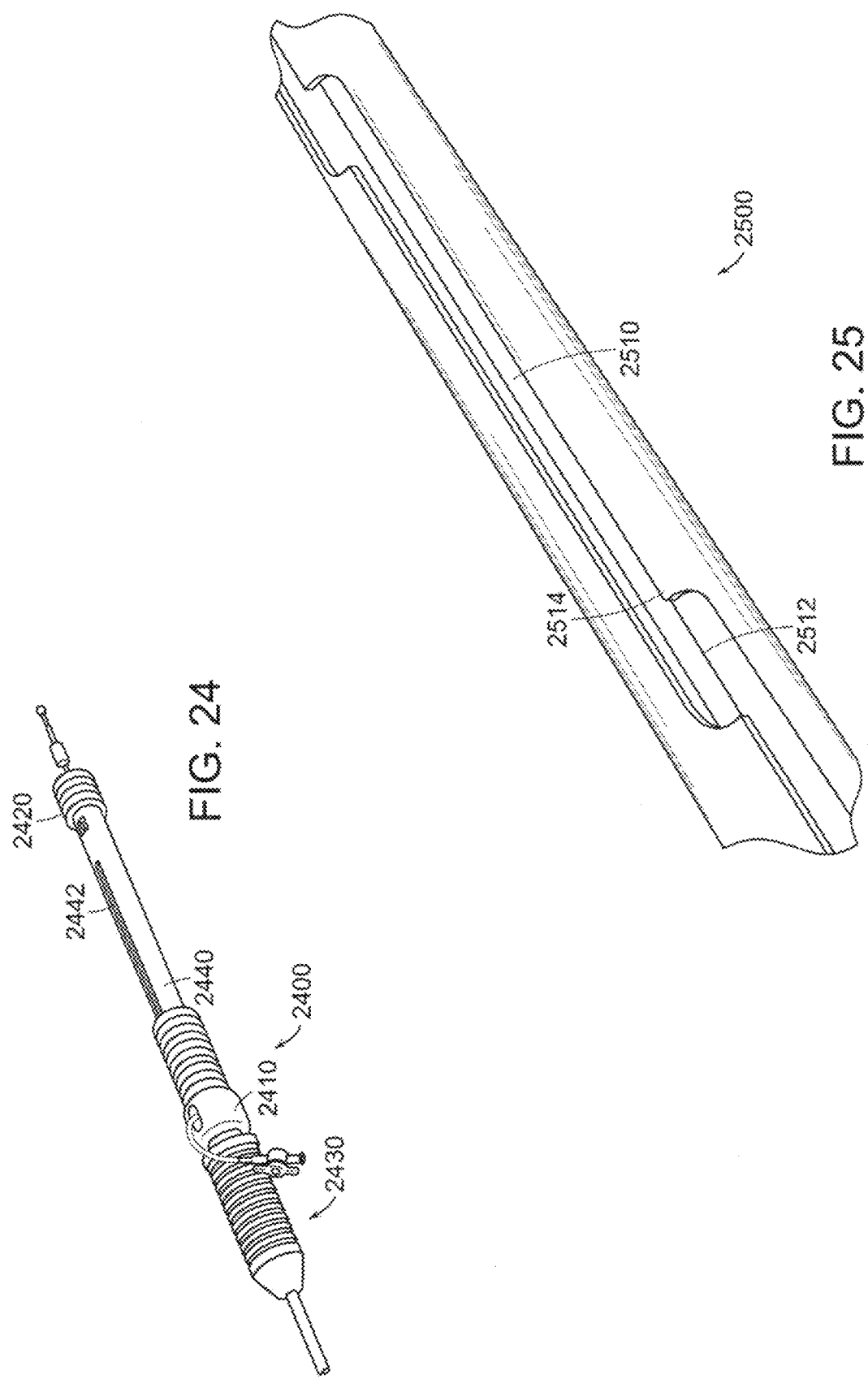

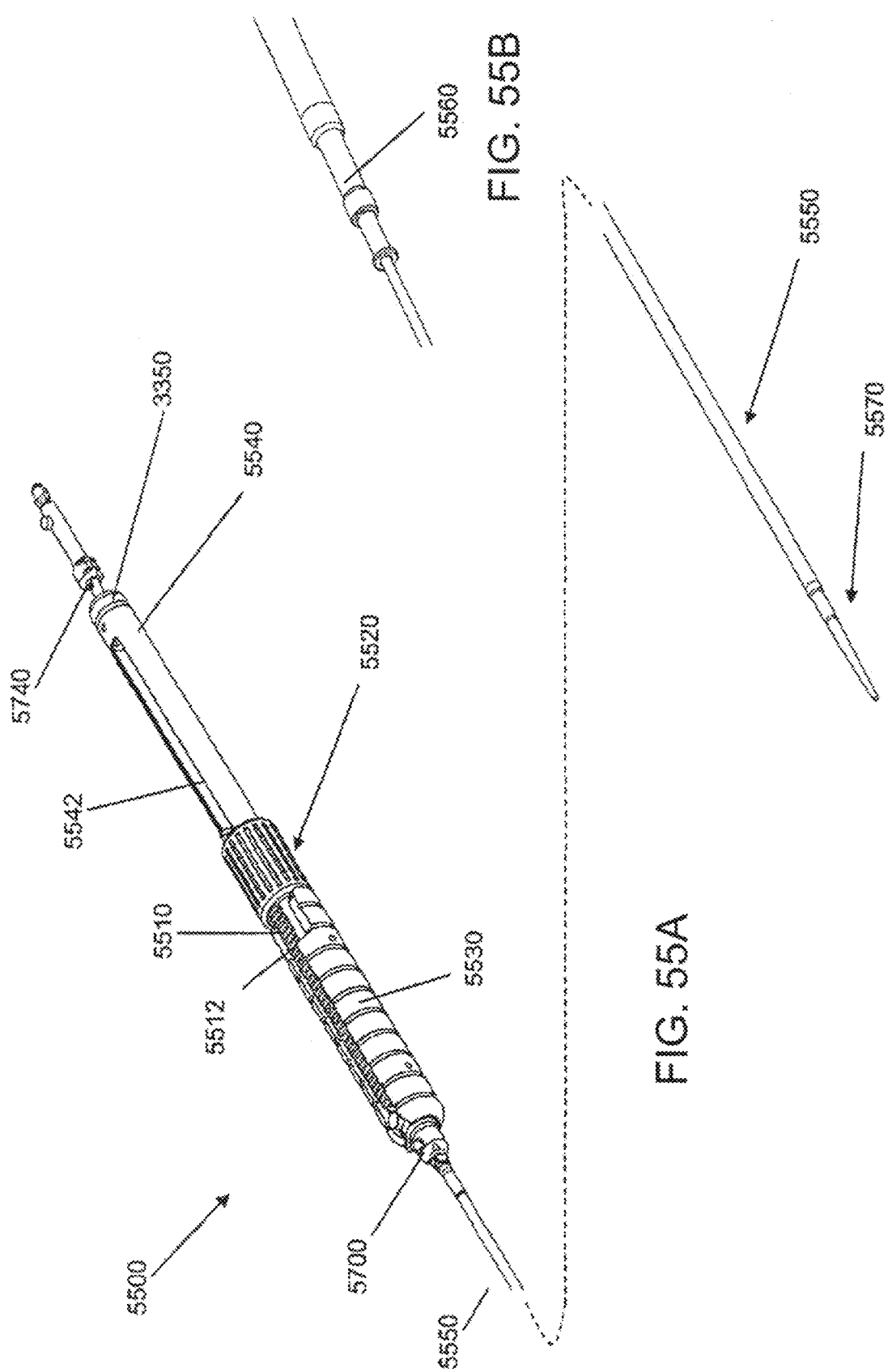

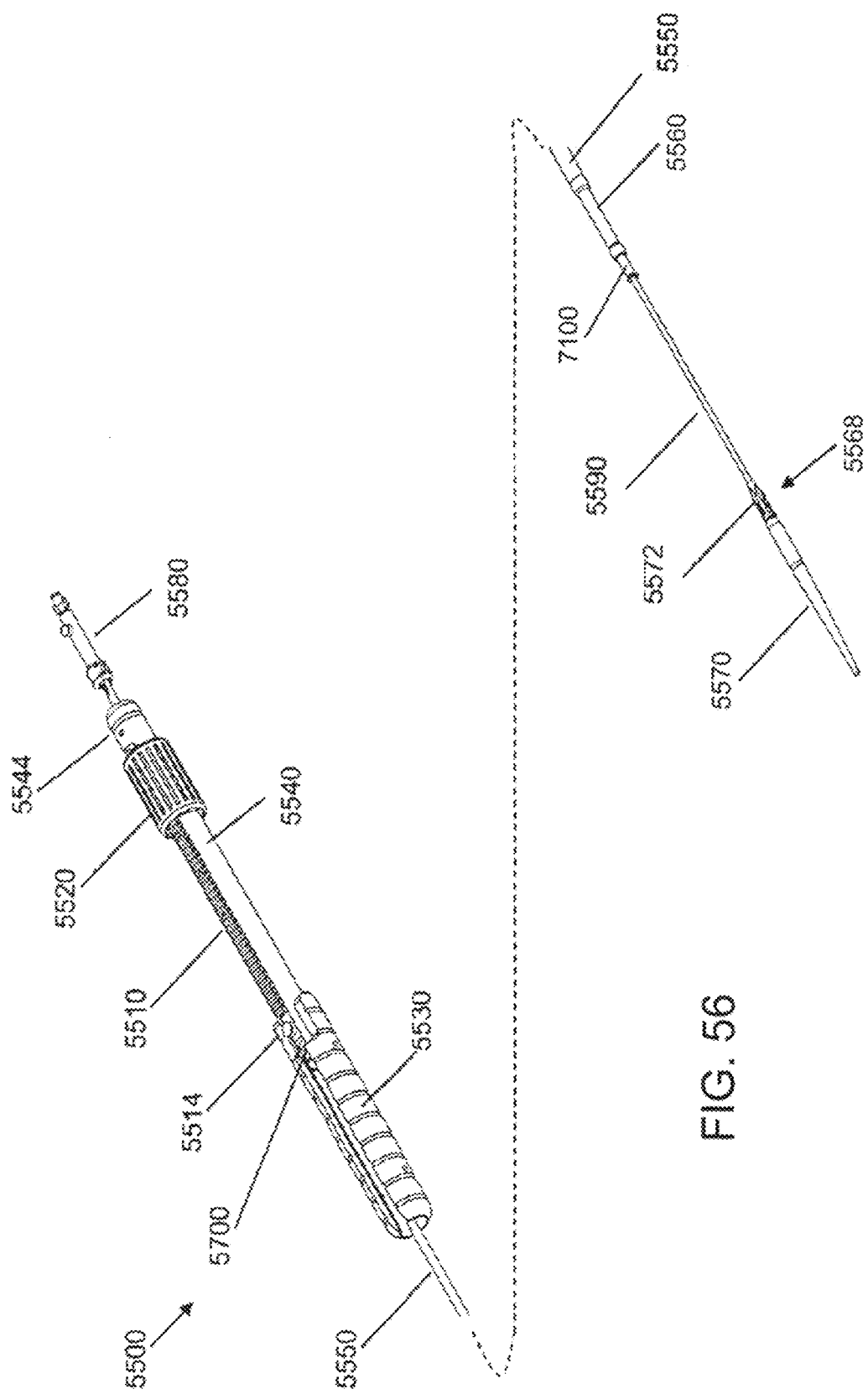

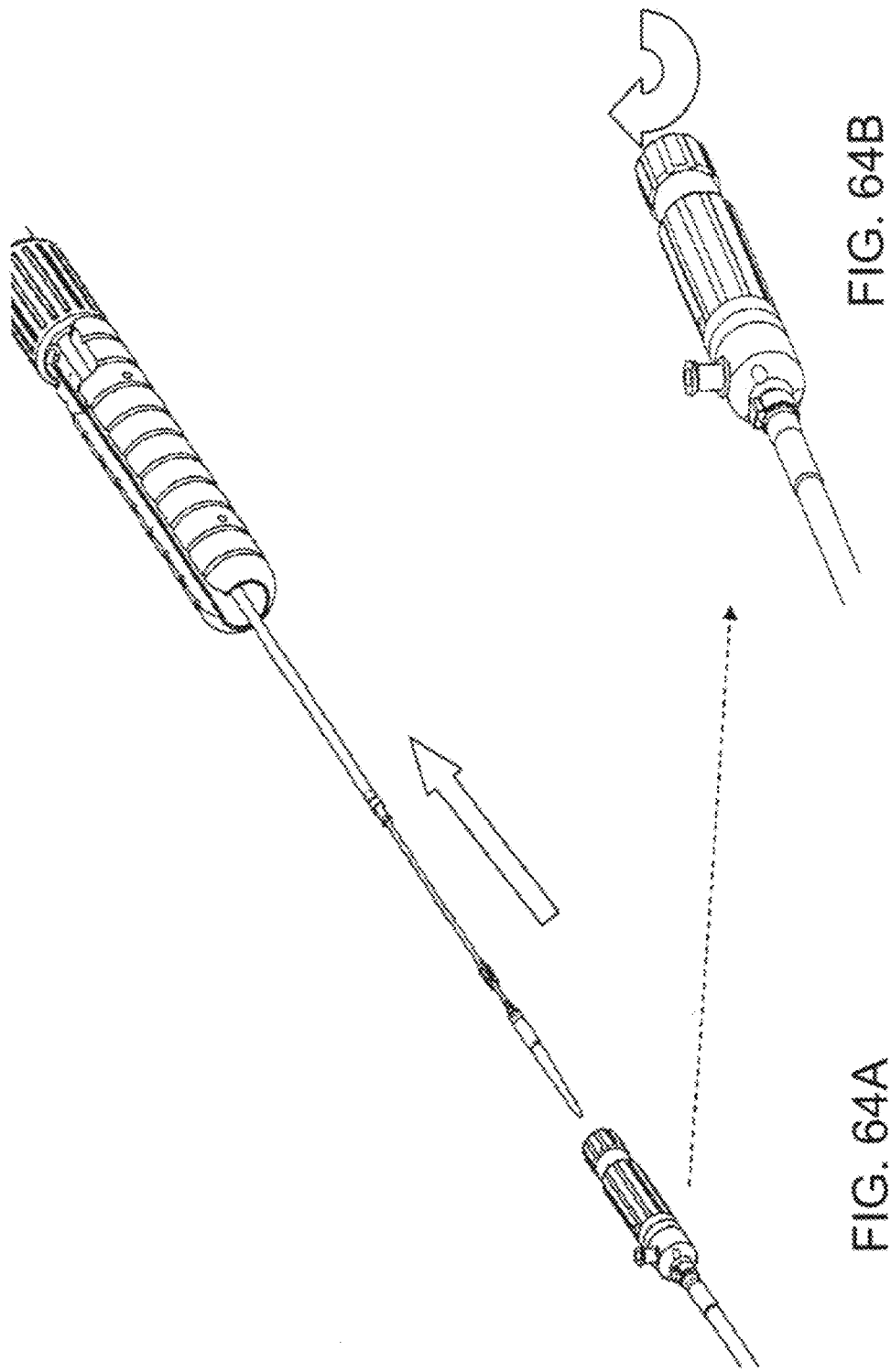

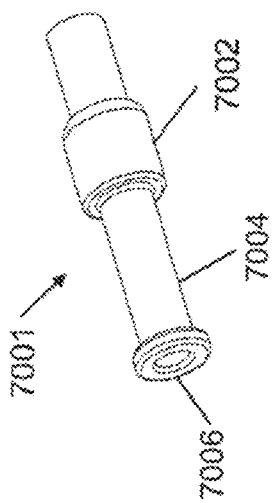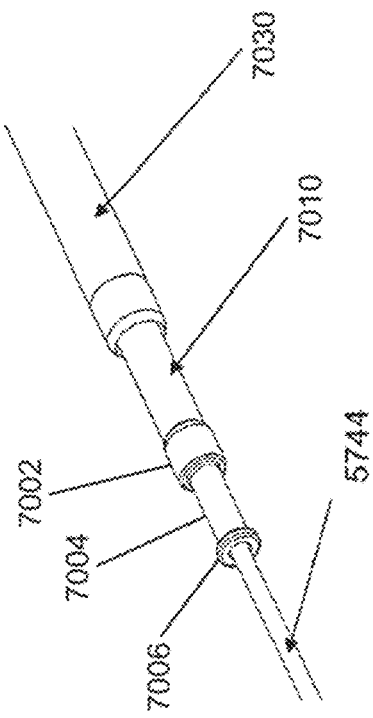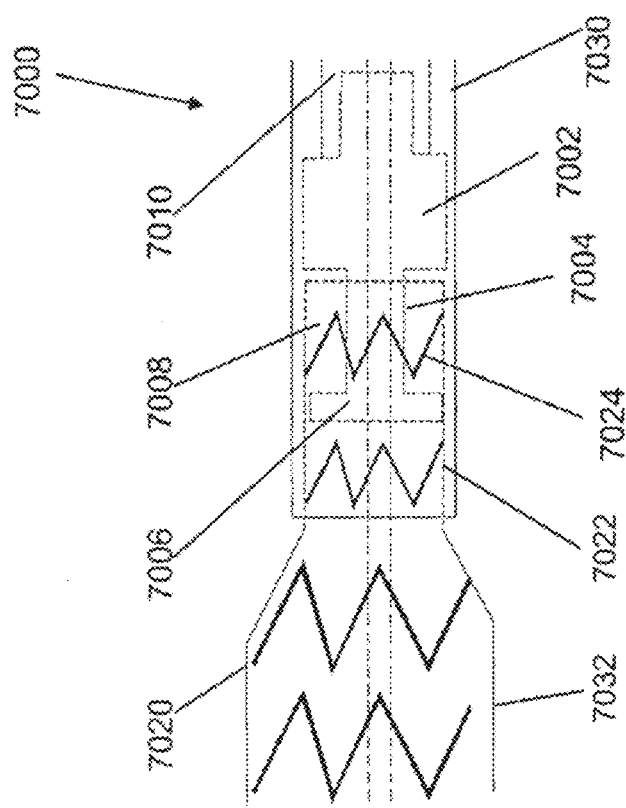

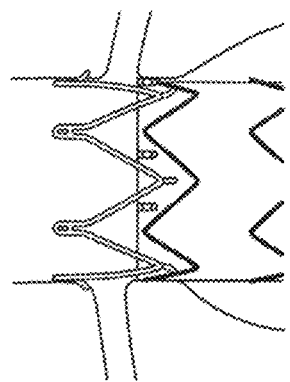
FIG. 72B
FIG. 72C
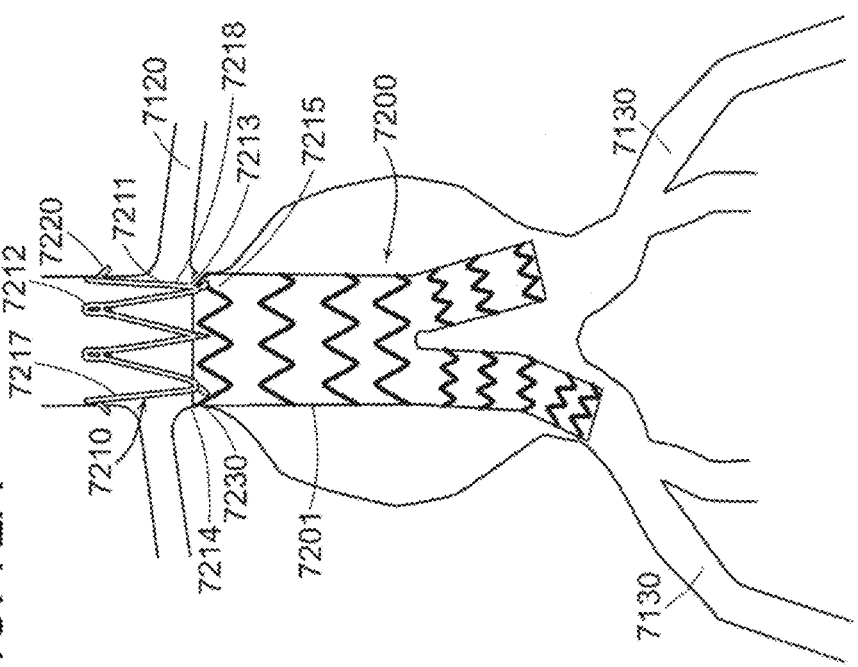
FIG. 72A

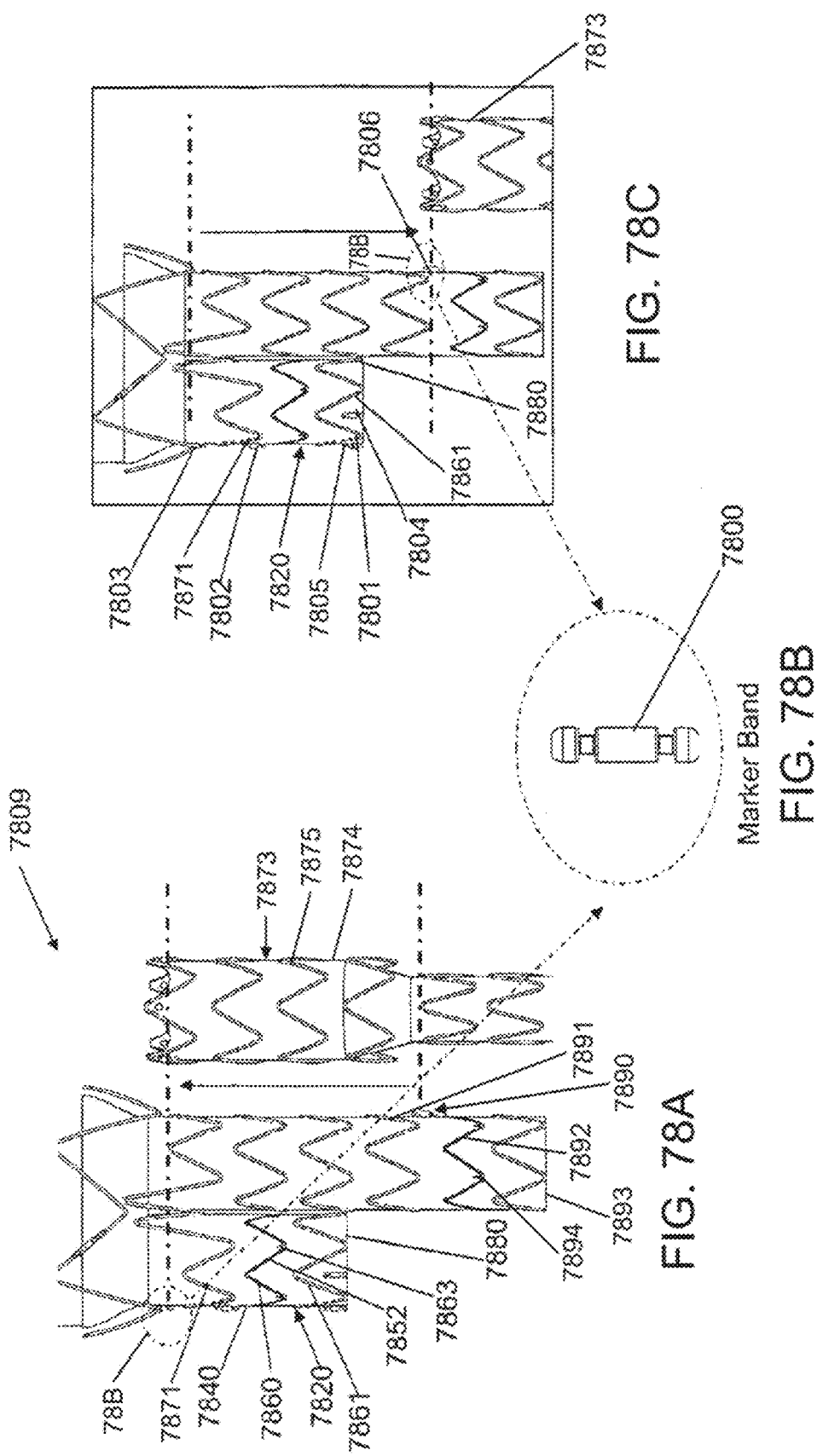

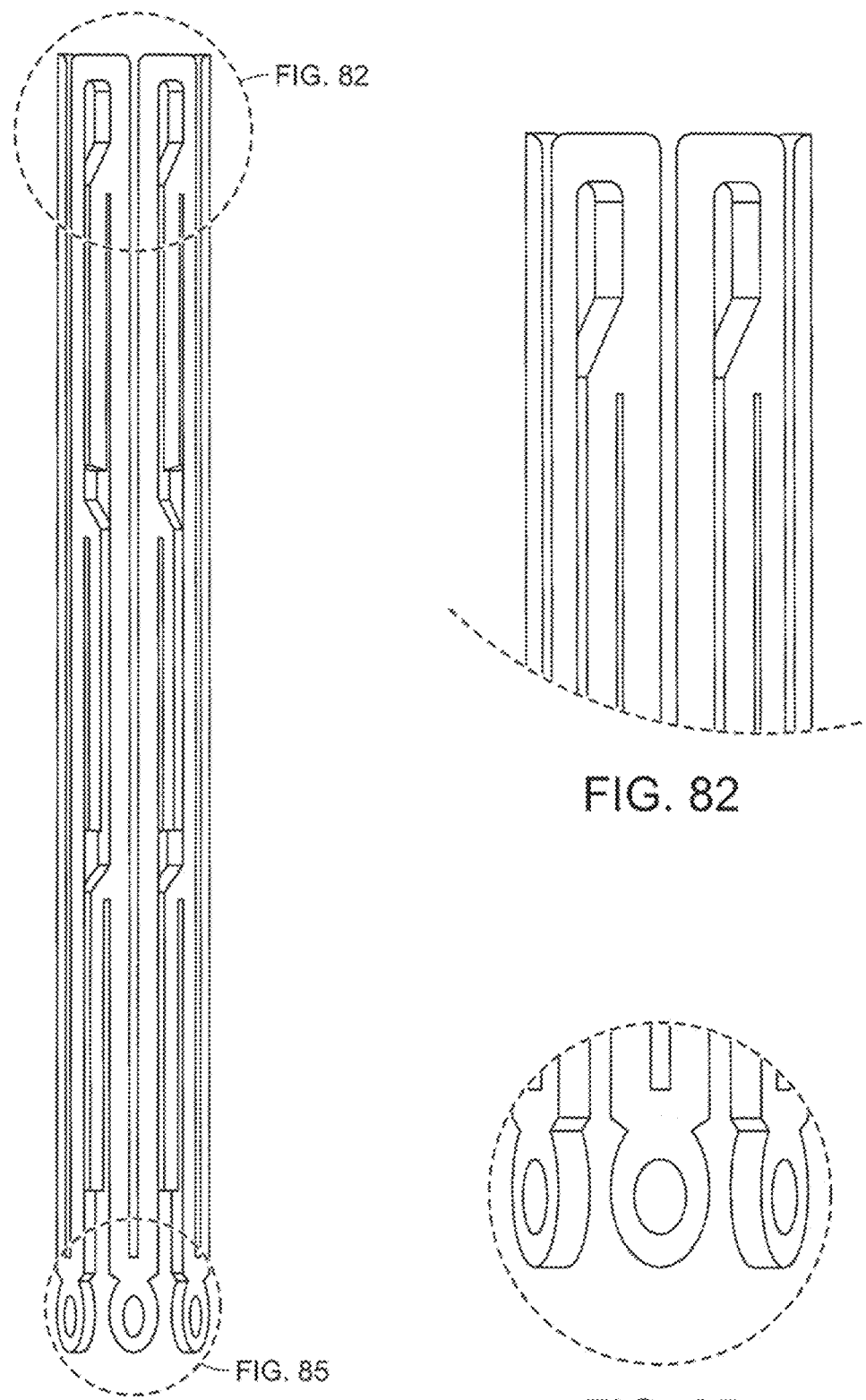

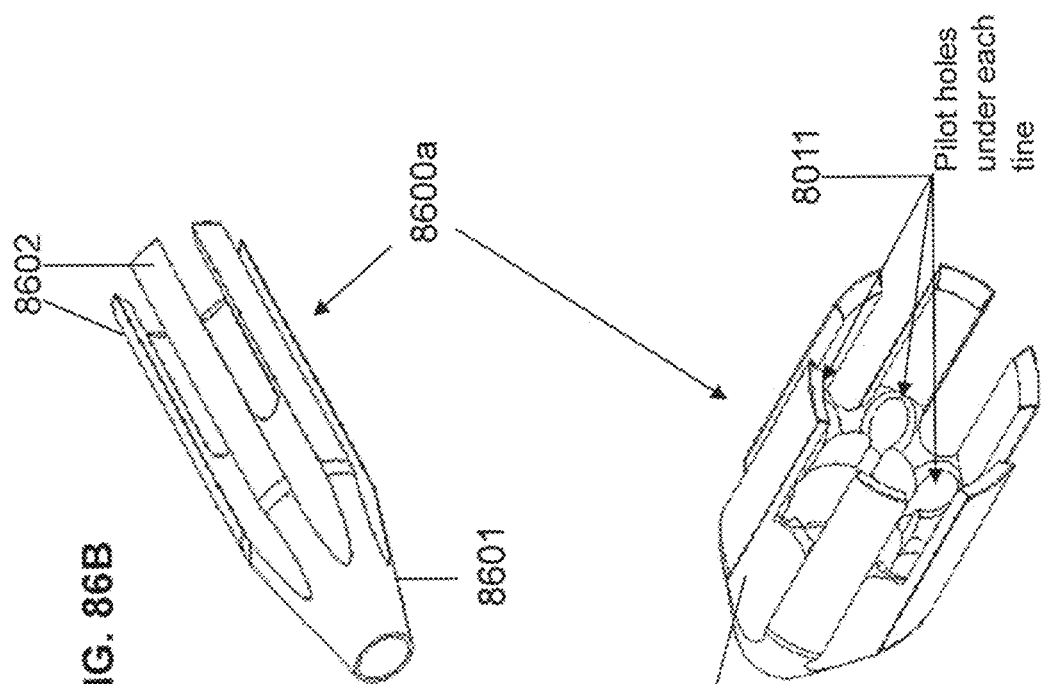
FIG. 86B
FIG. 86C
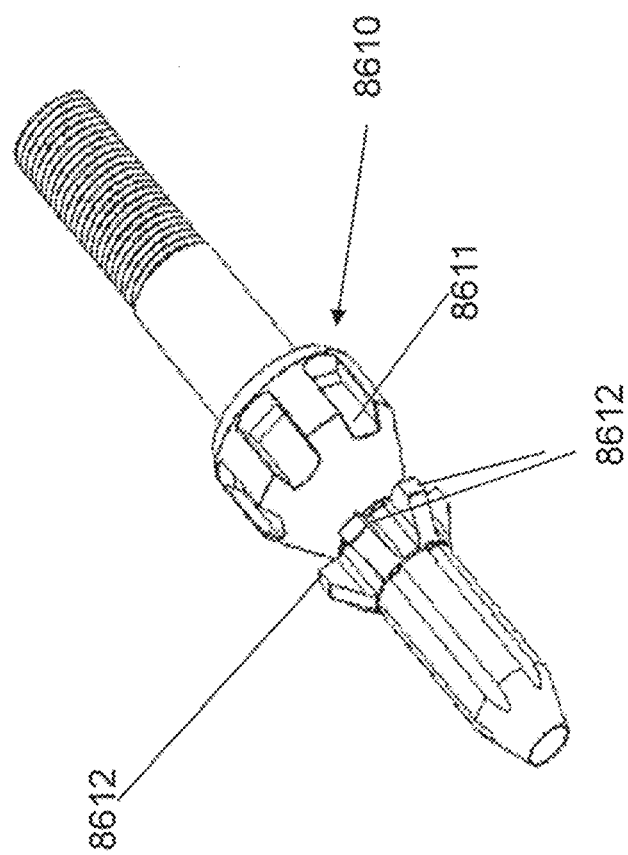
FIG. 86A

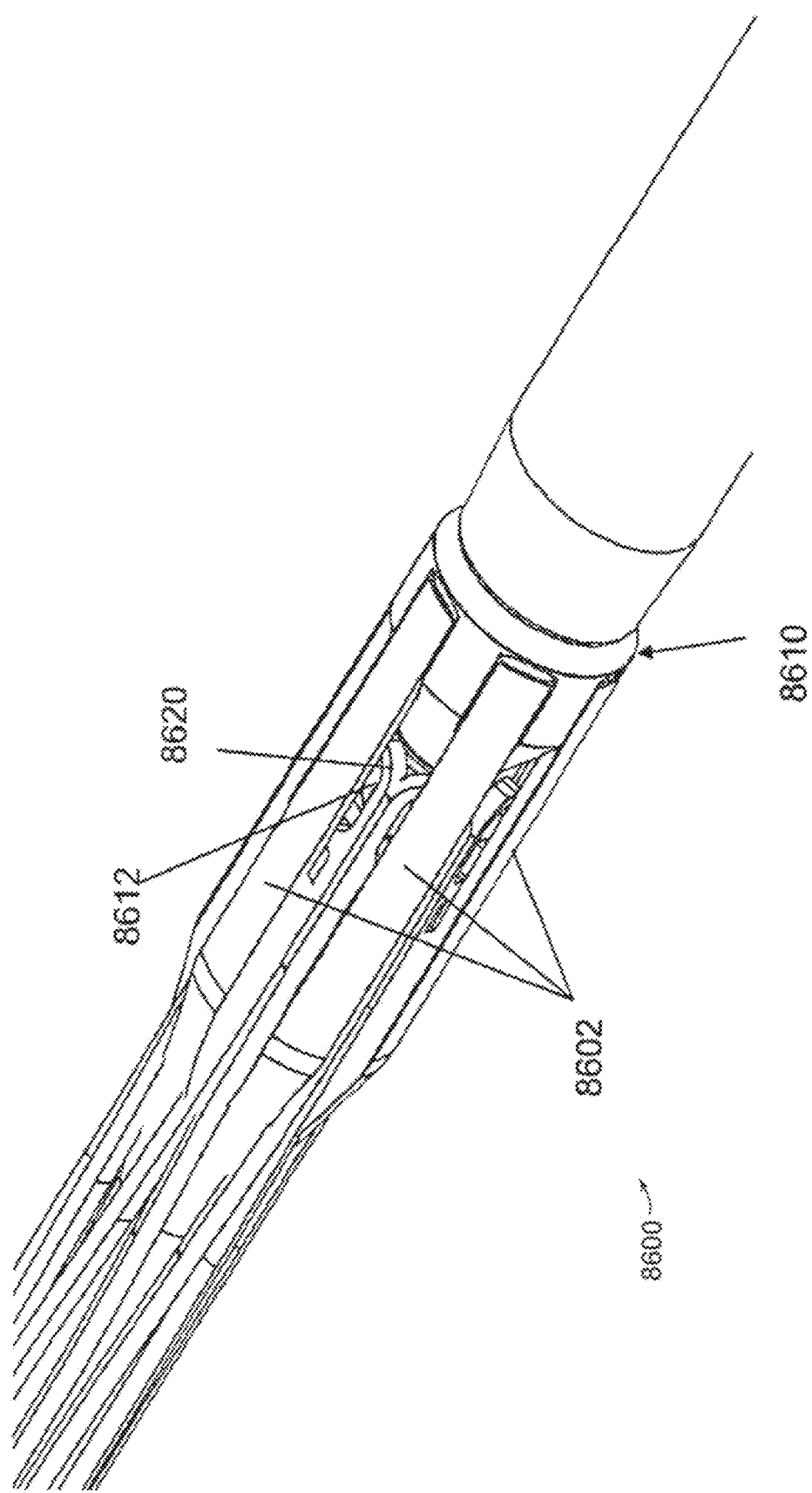

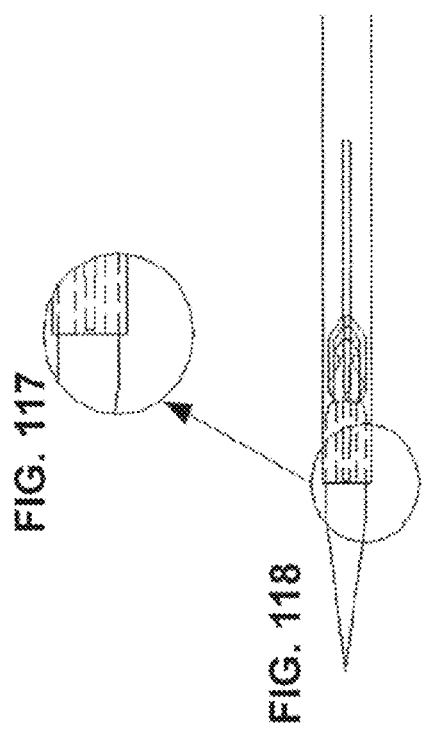
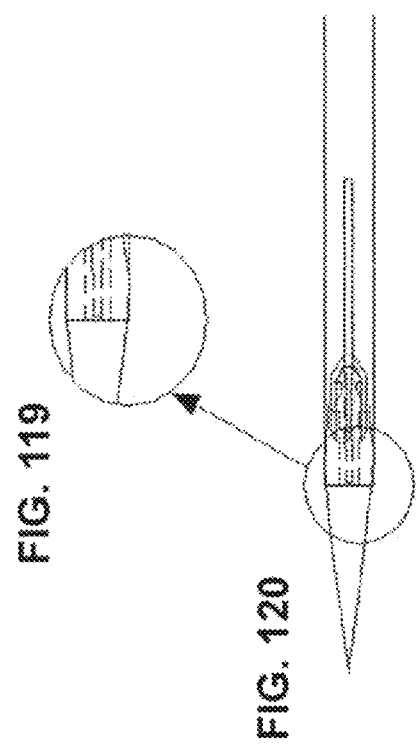
FIG. 117
FIG. 118
FIG. 119
FIG. 120

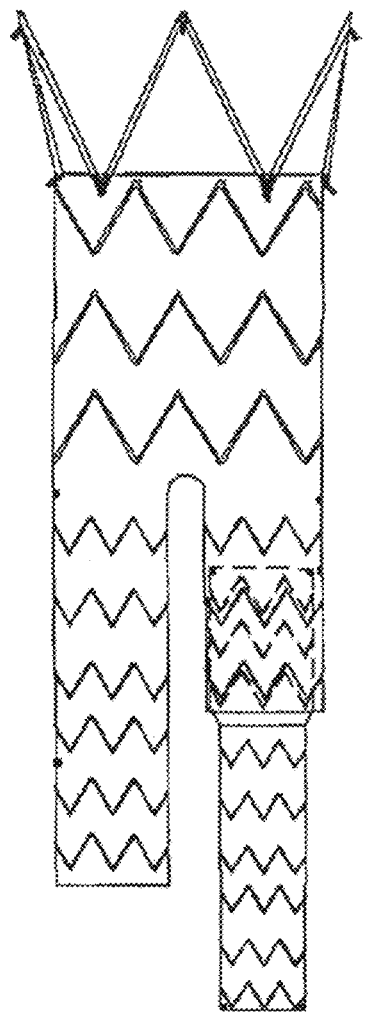 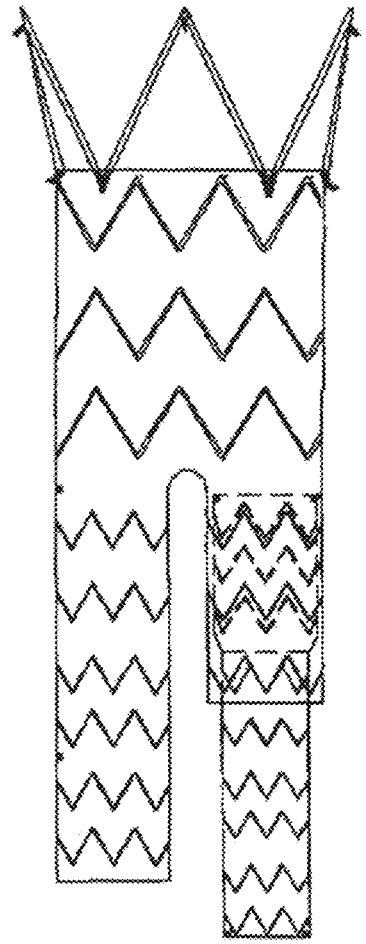
Contra- Min Overlap
Contra - Max Overlap
FIG. 127A
FIG. 127B Ipsi- Min Overlap Ipsi- Max Overlap

HEMOSTASIS VALVE AND DELIVERY SYSTEMS

RELATED APPLICATION

This application is a divisional of U.S. application Ser. No. 15/230,601, filed Aug. 8, 2016, which is a continuation of U.S. application Ser. No. 13/834,808, filed Mar. 15, 2013. The entire teachings of the above applications are incorporated herein by reference.

BACKGROUND OF THE INVENTION

Stent graft delivery systems have been designed to treat abdominal aortic aneurysms (AAA). Successful placement of components of a prosthesis is critical to bypass the aneurysm. Prostheses can be deployed as multiple units, each requiring separate deployment from a delivery system. Prevention of extracorporeal blood flow while changing delivery devices during implantation of a main prosthesis, or in the absence of blood vessel filling catheters or accessories, can be accomplished by hemostasis valves. Thus, there is a need to develop new, useful and effective delivery systems, components and methods having hemostasis valves to treat AAA.

SUMMARY OF THE INVENTION

The present invention relates to delivery systems, components of delivery systems and methods of using the delivery systems and its components to treat vascular damage, in particular AAA.

In one embodiment, the invention is a hemostasis valve that includes a longitudinal valve housing, a gasket housing, a grip assembly at the proximal end of the longitudinal valve housing, and interference element at the longitudinal valve housing. The longitudinal valve housing defines a conduit and has a proximal end and a distal end. The gasket within the housing defines an interior conduit and has a distal end, the distal end being fixed relative to the longitudinal valve housing, a proximal end moveable relative to the longitudinal valve housing, and a collapsible intermediate portion between the distal end and the proximal end. In an embodiment, the interior conduit of the gasket has an essentially constant diameter from the distal end portion to the proximal end portion of the gasket. The grip assembly at the proximal end of the longitudinal valve housing is linked to the proximal end of the gasket. The grip assembly includes: a grip portion at the first end of, and rotatable relative to, the longitudinal valve housing; a spindle portion extending from the grip portion and within the conduit of the longitudinal valve housing, the spindle being fixed to the gasket at the proximal end of the gasket; and a ratchet extending about the spindle and fixed to the spindle. The ratchet defines teeth and is at the end of the ratchet extending about the spindle. The ratchet is biased in a direction relative to the longitudinal valve housing and along the major longitudinal axis of the longitudinal valve housing. The interference element is located within the longitudinal valve housing, is in interfering relation with the teeth of the ratchet, and is biased against the teeth of the ratchet, whereby rotation of the grip portion relative to the longitudinal valve housing causes rotation of the proximal end of the gasket relative to the distal end of the gasket, thereby changing the internal diameter of the internal conduit. Rotation of the grip portion relative to the housing also causes the teeth of the ratchet to disengage and reengage the interference element with the ratchet, re-engagement of the ratchet with interference element locking the diameter of the internal conduit of the gasket in place upon termination of rotation of the grip portion relative to the longitudinal valve housing.

Another embodiment of the invention is an x-valve that includes: a valve housing; at least one sealing component within the valve housing, wherein the sealing component defines at least one slot; and a support layer at least partially embedded within the sealing component.

In still another embodiment of the invention, a stent graft delivery system of the invention includes: a handle; an internal lead screw assembly; a lead screw nut; a support member: a sheath extending about a portion of the support member; and a hemostasis valve about the supporting member. The handle includes a distal grip and a handle body extending from one end of the distal grip. The handle body defines a conduit and a track along a portion of the length of the distal grip and the handle body. The internal lead screw assembly is located within the track, is movable along a major axis of the conduit, and includes a threaded portion that extends through the track. The lead screw nut extends about the handle body and is threadably engaged with the threaded portion of the internal lead screw assembly, whereby rotation of the lead screw nut while abutting the distal grip causes movement of the internal lead screw assembly relative to the handle. The lead screw nut is simultaneously slidable along the handle body while engaged with the internal lead screw assembly, thereby providing at least two mechanisms for causing movement of the internal lead screw relative to the handle. The support member is fixed to the handle body and the sheath extending about a portion of the support member is fixed to the internal screw assembly, whereby relative movement of the handle body and the lead screw assembly causes relative movement of the support member and sheath, wherein the support member includes a hypo tube and a support tube within the hypotube, wherein the hypotube is fixed to the handle body, and wherein the internal lead screw assembly defines an opening essentially coaxial with the handle, wherein the support member extends through the internal lead screw assembly. The hemostasis valve extends about the support member and between the sheath and the internal lead screw assembly, wherein the hemostasis valve includes a gasket having a distal end and a proximal end along a major longitudinal axis of the delivery system, and defines an internal conduit between the distal end of the gasket and a proximal end of the gasket through which the support member extends, wherein actuation of the hemostasis valve narrows the internal conduit about the support member, thereby closing the hemostasis valve.

In one embodiment of the stent graft delivery system of the invention, the hemostasis valve includes an x-valve along a longitudinal axis of the delivery system, wherein the x-valve includes at least one pair of sealing layers defining intersecting slots and a support layer partitioning the sealing layers.

The hemostasis valves of the invention have the advantage of providing selective and secure complete opening and closing of blood flow while changing delivery devices to implantation components of prosthesis to treat AAA. Thus, delivery systems, components of delivery systems and methods of the invention can be used to treat AAA and, therefore, avoid complications and death consequent to life threatening vascular conditions.

BRIEF DESCRIPTION OF THE DRAWINGS

FIG. 4 depicts an embodiment of a stent delivery system of the invention.

FIG. 5 depicts an embodiment of a stent delivery system of the invention.

FIG. 6 depicts an embodiment of a stent delivery system of the invention.

FIG. 7 is an alternative embodiment of the delivery system of the invention.

FIG. 8 is an alternative embodiment of the delivery system of the invention.

FIG. 9 is an alternative embodiment of the delivery system of the invention.

FIG. 10 is an embodiment for connecting an outer sheath handle to an inner screw that can be employed in the delivery systems of the invention. Screws (716) are offset to fall in the threads.

FIG. 11 is an embodiment for connecting an outer sheath handle to an inner screw that can be employed in the delivery systems of the invention.

FIG. 12 is an embodiment of the delivery system of the invention. The handle is turned (curved arrow) to retract sheath. Handle is held stationary while turning the handle to retract the sheath.

FIG. 13 is an embodiment of the delivery system of the invention. When threads are completely disengaged, the handle will lock into the slots and the bore spring and sealing spring will be exposed.

FIG. 14 is an embodiment of the delivery system of the invention. The sheath is retracted so the main body of the bifurcated graft is exposed by sliding the handle over the threaded engagement.

FIGS. 15A, 15B, 15C and 15 D are embodiments of the delivery system of the invention. As shown in FIG. 15A, the apex clasp is released to deliver the bifurcated stent graft. The arrow depicts force.

FIG. 20 is another embodiment of the delivery system of the invention. The handle is turned (curved arrow) to retract the sheath. The handle is kept stationary while turning to retract the sheath.

FIG. 21 is another embodiment of the delivery system of the invention. Once the threads are completely disengaged the bare spring and sealing spring will be exposed and the turning of the handle will not retract the sheath back any further.

FIG. 22 is another embodiment of the delivery system of the invention. Pin and pull—retract the sheath so the main body of the graft is exposed by sliding the handle back over the lead screw handle.

FIG. 23 is another embodiment of the delivery system of the invention. The apex clasp is released.

FIG. 24 is another embodiment of the delivery system of the invention.

FIG. 25 is another embodiment of the delivery system of the invention.

FIGS. 55A and 55B are additional embodiments of the delivery system of the invention.

FIG. 56 is another embodiment of the delivery system of the invention.

FIGS. 64A and 64B are embodiments of a delivery system of the invention.

FIGS. 70A, 70B and 70C are embodiments of a leg clasp system of the invention.

FIGS. 72A, 72B and 72C are embodiments of a stent graft system of the invention. FIG. 72A is an example of placement of a stent graft system of the invention to treat an abdominal aortic aneurysm.

FIGS. 78A, 78B and 78C are embodiments of a telescoping stent grafts system of the invention.

FIG. 81 is a representation of an unexpanded stent of the invention.

FIG. 82 is a representation of an unexpanded stent of the invention.

FIG. 85 is a representation of an unexpanded stent of the invention.

FIGS. 87A and 87B are embodiments of the apex capture device of the invention.

FIG. 117 is an embodiment of a component of the delivery system of the invention.

FIG. 118 is an embodiment of a component of the delivery system of the invention.

FIG. 119 is an embodiment of a component of the delivery system of the invention.

FIG. 120 is an embodiment of a component of the delivery system of the invention.

FIG. 121 is an embodiment of a component of the delivery system of the invention.

FIG. 122 is an embodiment of a component of the delivery system of the invention.

FIG. 123 is an embodiment of a component of the delivery system of the invention.

FIG. 124 is an embodiment of a component of the delivery system of the invention.

FIG. 125 is representative of a leg clasp of the invention.

FIG. 126 is representative of a leg clasp of the invention.

FIGS. 127A, 127B, 127C and 127D are representative of a telescoping stent graft system of the invention.

FIG. 128 is an embodiment of the delivery system of the invention.

FIG. 129A is a perspective view of a representation of an embodiment of a hemostasis valve of the invention.

FIG. 129B is a perspective view of a representation of components of an embodiment of a hemostasis valve of FIG. 129A.

FIG. 129C is another perspective view of a representation of embodiments of x-valves of a hemostasis valve of FIG. 129A.

Figure 129:
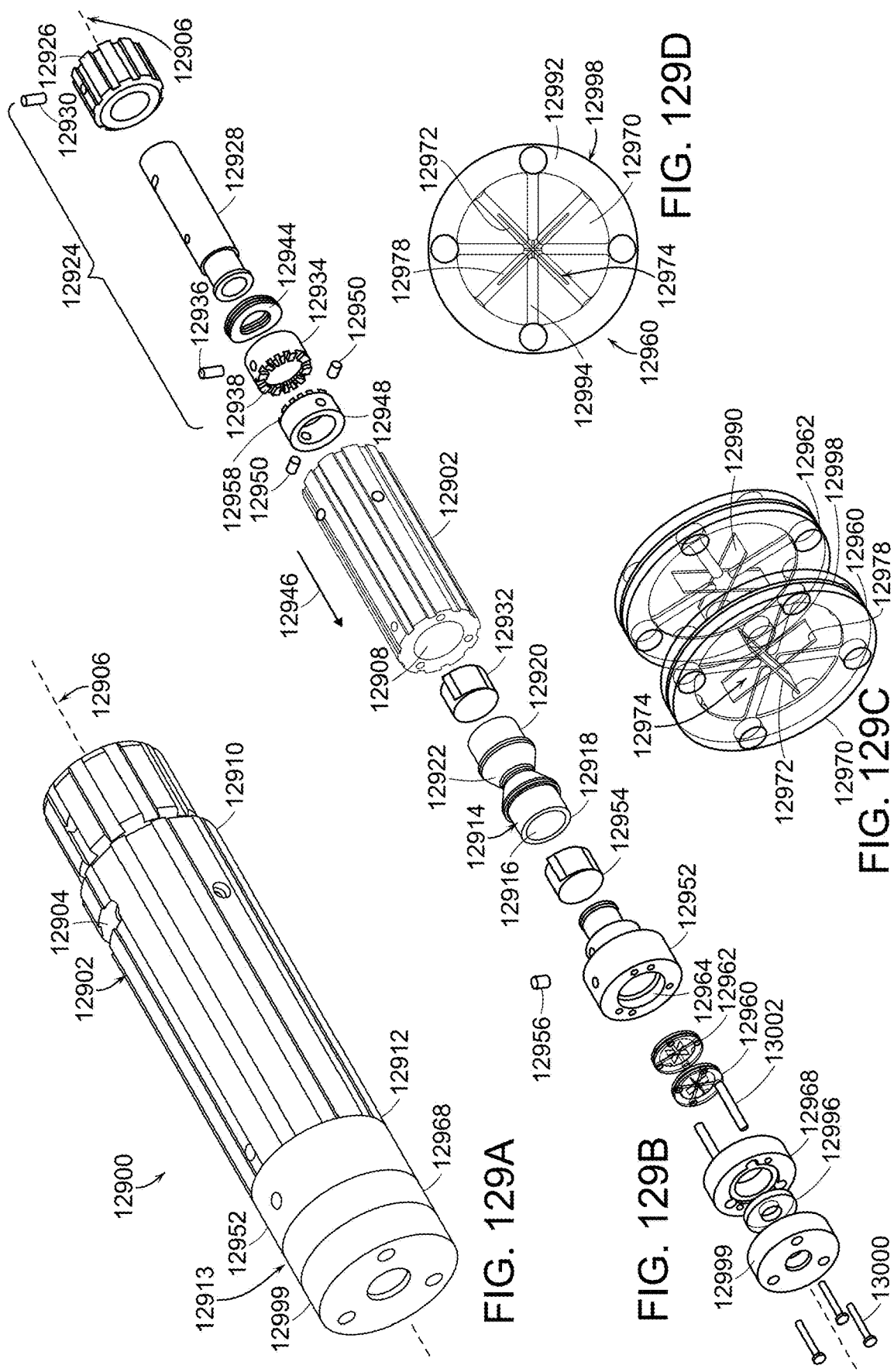

FIG. 129D is a perspective view of a representation of an embodiment of an x-valve of a hemostasis valve of FIG. 129A.

Figure 130:
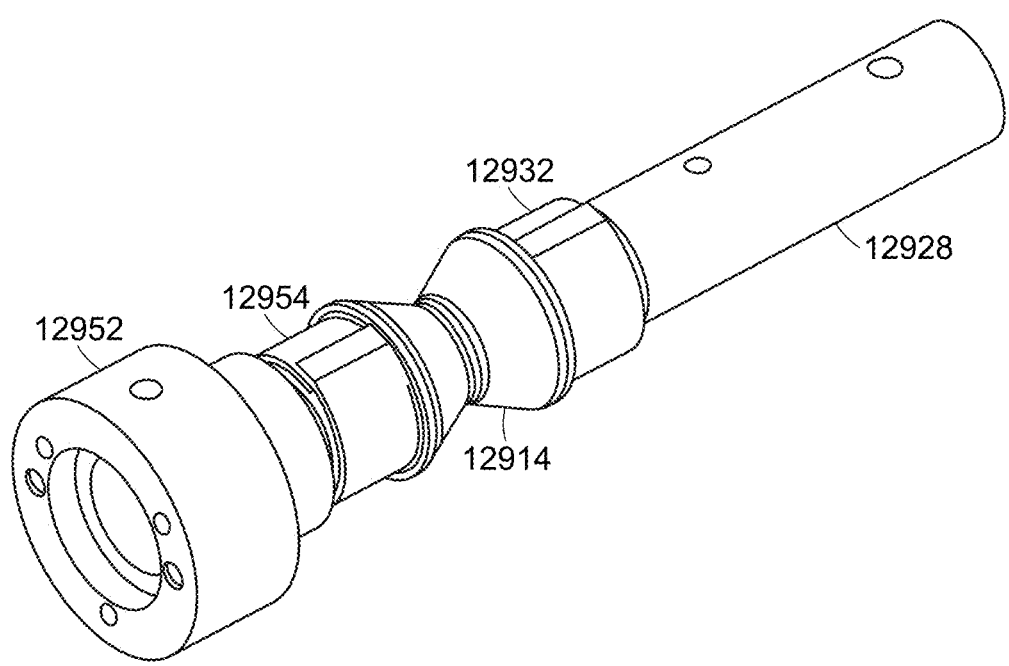

FIG. 130 is a perspective view of a representation of an embodiment of a spindle, proximal oetiker clamp, distal oetiker clamp, gasket and main boss of a hemostasis valve of FIG. 129A.

Figure 131A:
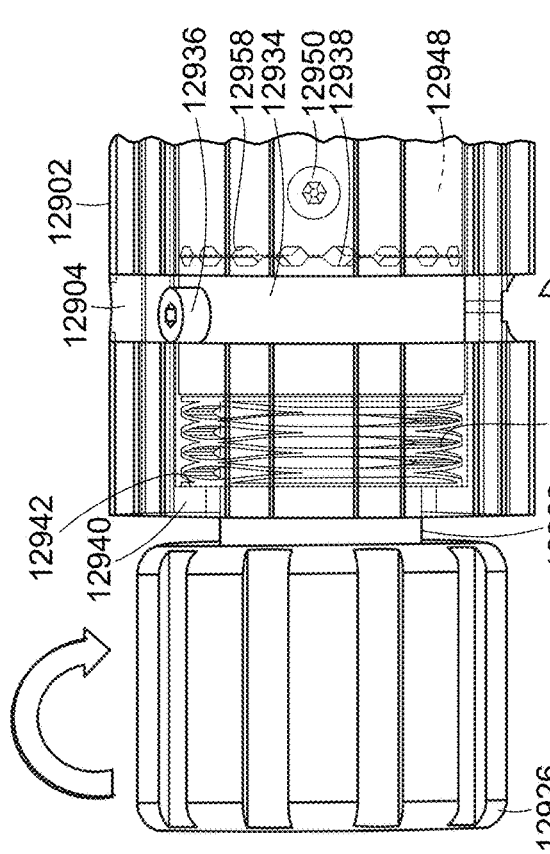

FIG. 131A is a partial cutaway of an embodiment of a hemostasis valve of FIG. 129A.

Figure 131B:
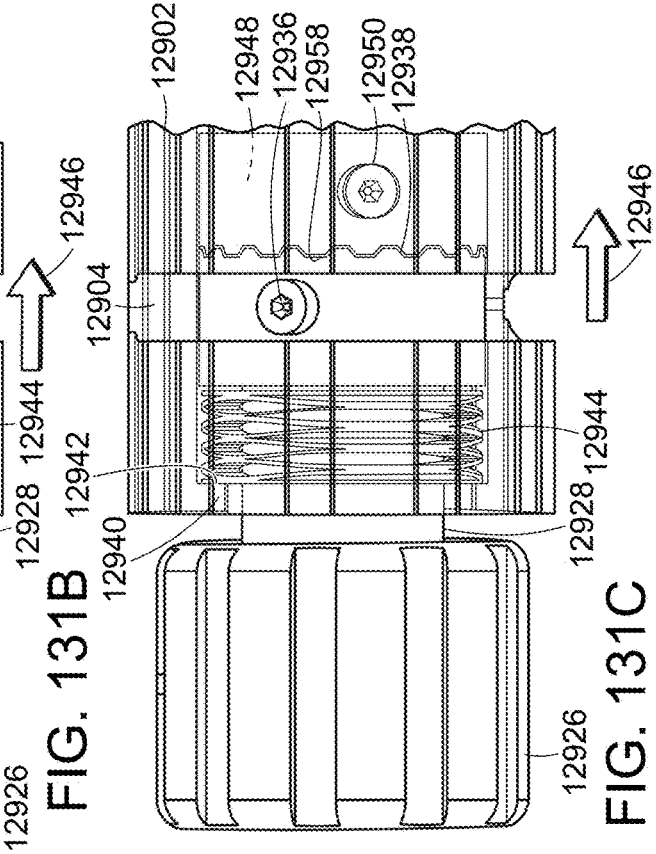

FIG. 131B is another partial cutaway of an embodiment of a hemostasis valve of FIG. 129A.

Figure 131C:
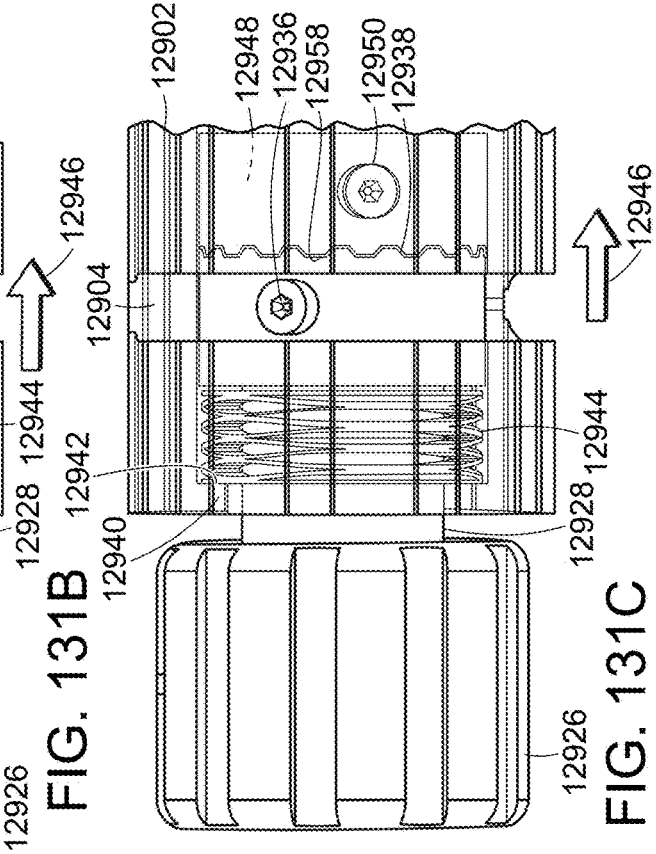

FIG. 131C is another partial cutaway of an embodiment of a hemostasis valve of FIG. 129A.

Figure 132B:
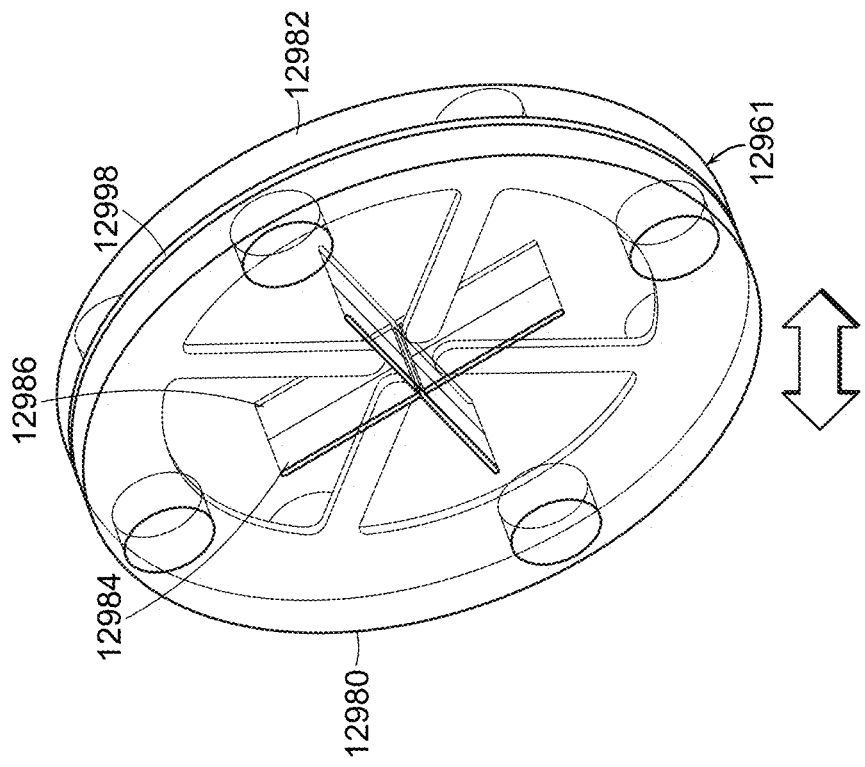
Figure 132A:
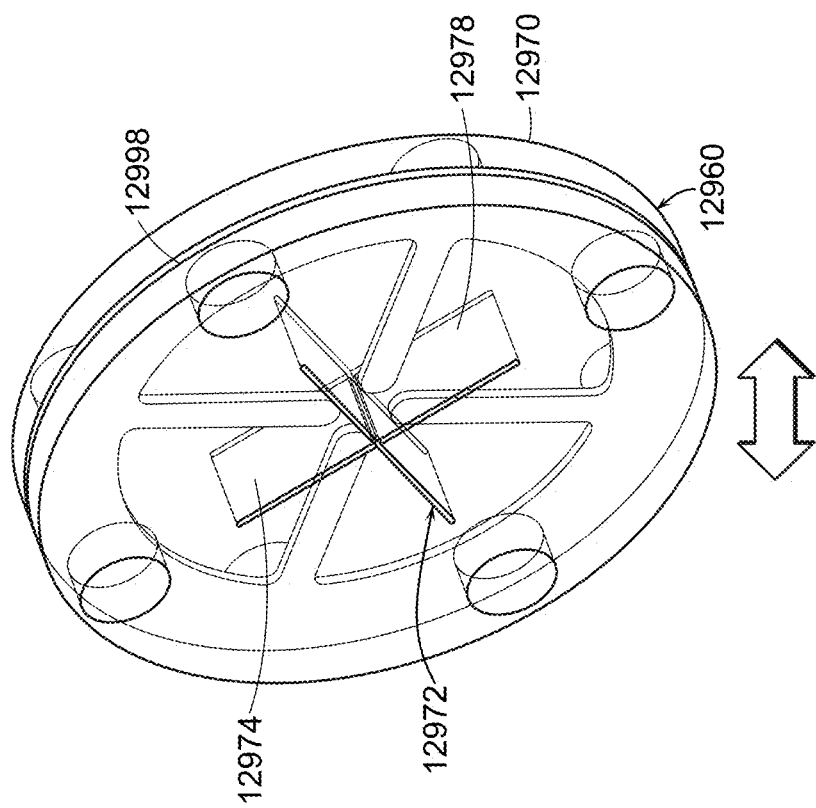

FIG. 132A is a detailed perspective view of an x-valve of FIG. 129C.

FIG. 132B is a detailed perspective view of an x-valve of FIG. 129C.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

Figure 1:
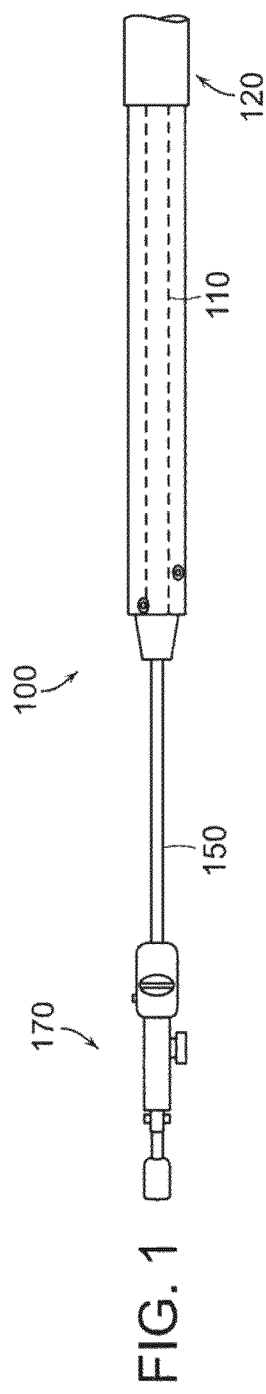
FIG. 1 represents an embodiment of a delivery system of the invention.

In an embodiment, represented by FIGS. 1 through 57, as an example, the invention is a stent graft delivery system 5500, comprising a handle that includes distal grip 5530 and handle body 5540 extending from one end of distal grip 5530, the handle defining conduit and track 5542 along a portion of the length of distal grip 5530 and handle body 5540; an internal lead screw assembly 5510 within the conduit, the internal lead screw assembly 5510 being moveable along a major axis of the conduit, and including a threaded portion 5512 that extends through the track 5542; a lead screw nut 5520 that extends about the handle body 5540 and threadably engaged with the threaded portion 5512 of the internal lead screw assembly 5510, whereby rotation of the lead screw nut 5520 while abutting the distal grip 5530 causes movement of the internal lead screw assembly 5510 relative to the handle and wherein the lead screw nut 5520 simultaneously is slidable along the handle body 5540 while engaged with the internal lead screw assembly 5510, thereby providing at least two mechanisms for causing movement of the internal lead screw assembly 5510 relative to the handle.

Figure 57A:
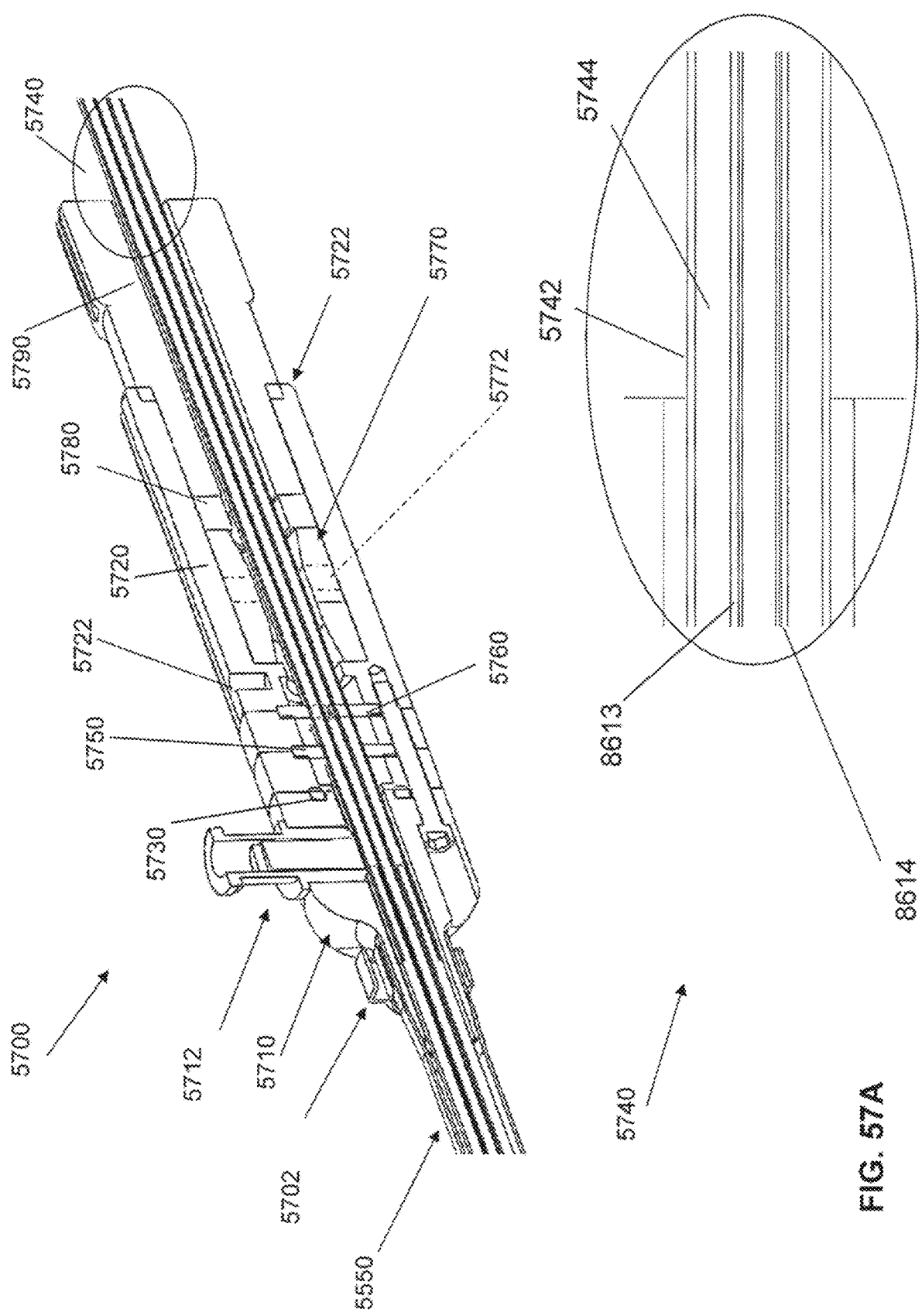
FIGS. 57A, 57B, 57C, 57D, 57E and 57F are another embodiment of the delivery system of the invention (sheath valve assembly).
Figure 57D:
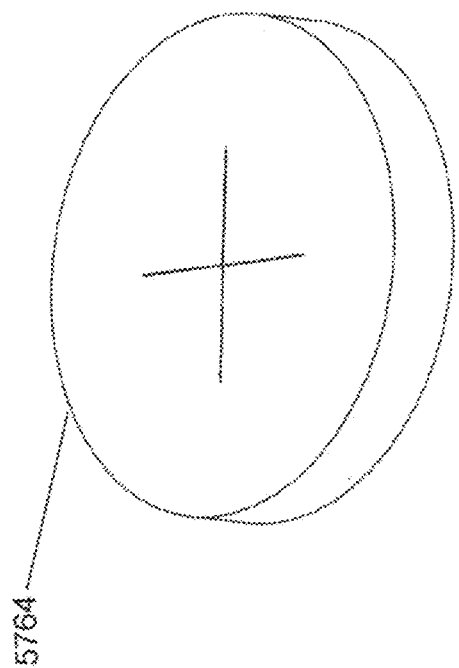
Figure 57C:
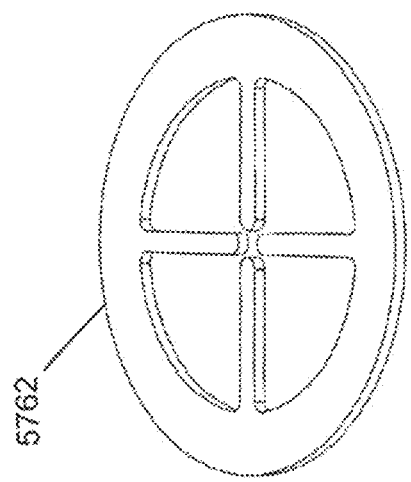

Referring to FIG. 57A, the stent graft delivery system can further include a support member 5740 fixed to the handle body, and an outer sheath 5550 extending about a portion of the support member 5740 and fixed, either directly or through slider 5700, to the internal lead screw assembly 5510, whereby relative movement of the handle body 5540 and the internal lead screw assembly 5510 causes relative movement of the support member 5740 and the outer sheath 5550.

The internal lead screw assembly 5510 of the stent graft delivery system 5500 of the invention can define an opening essentially coaxial with the handle, wherein the support member extends through the internal lead screw assembly, as shown in FIG. 55A.

Figure 86D:
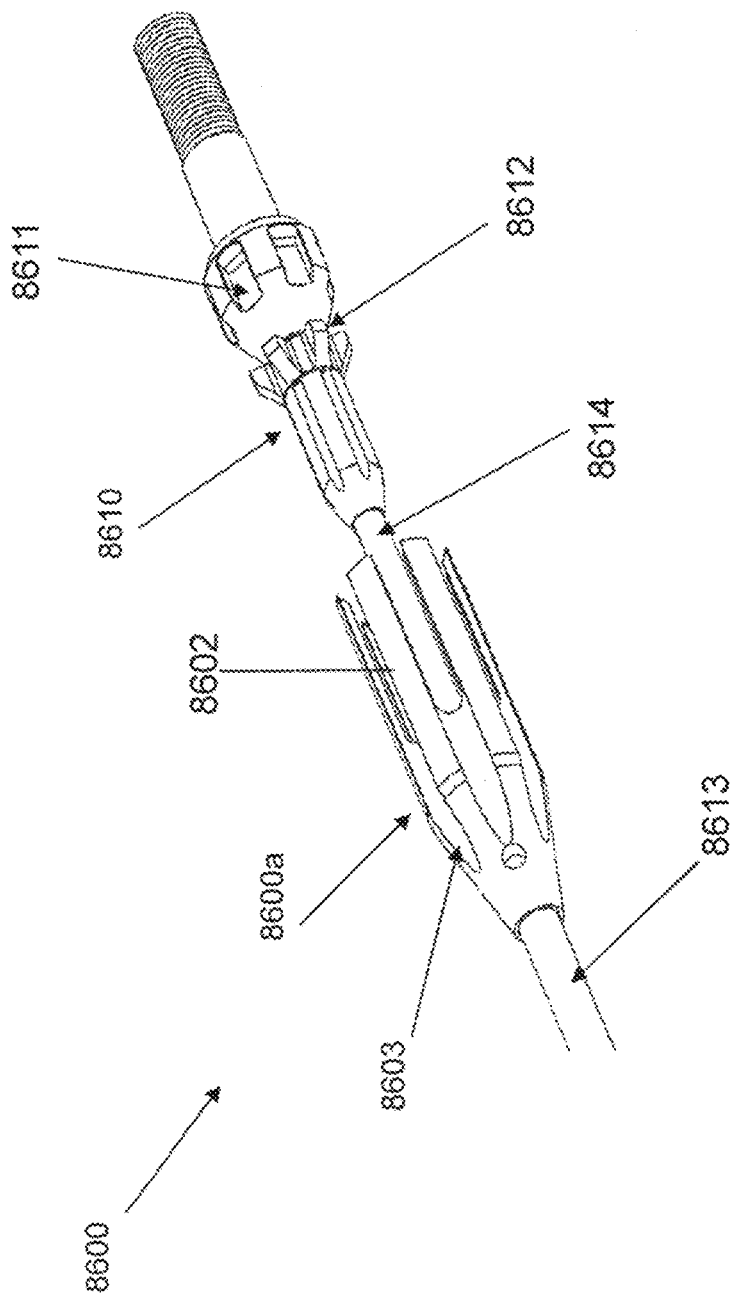
FIGS. 86A, 86B, 86C, 86 D and 86E are an embodiment of the apex capture device of the invention.
Figure 86E:
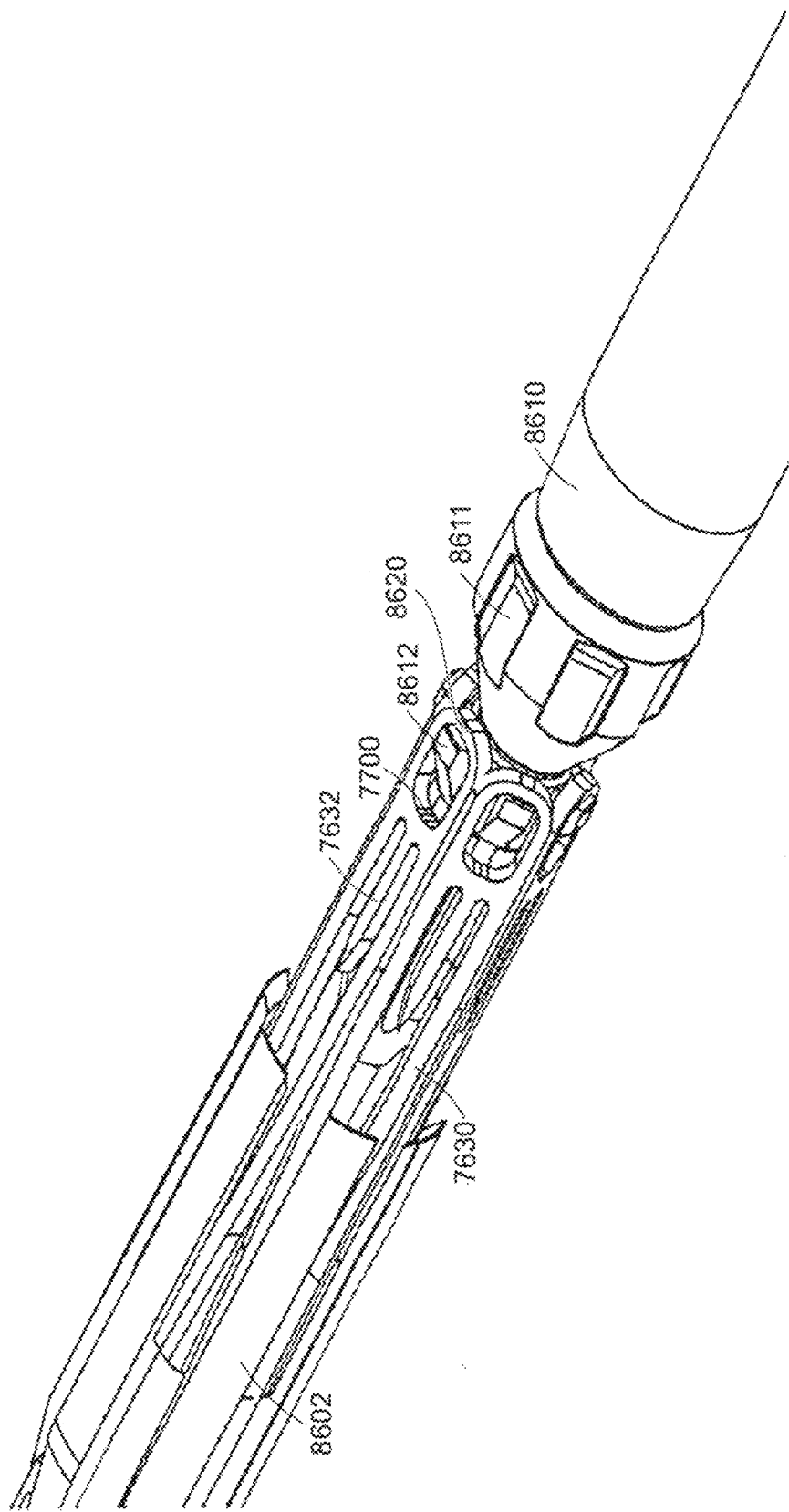
Figure 87A:
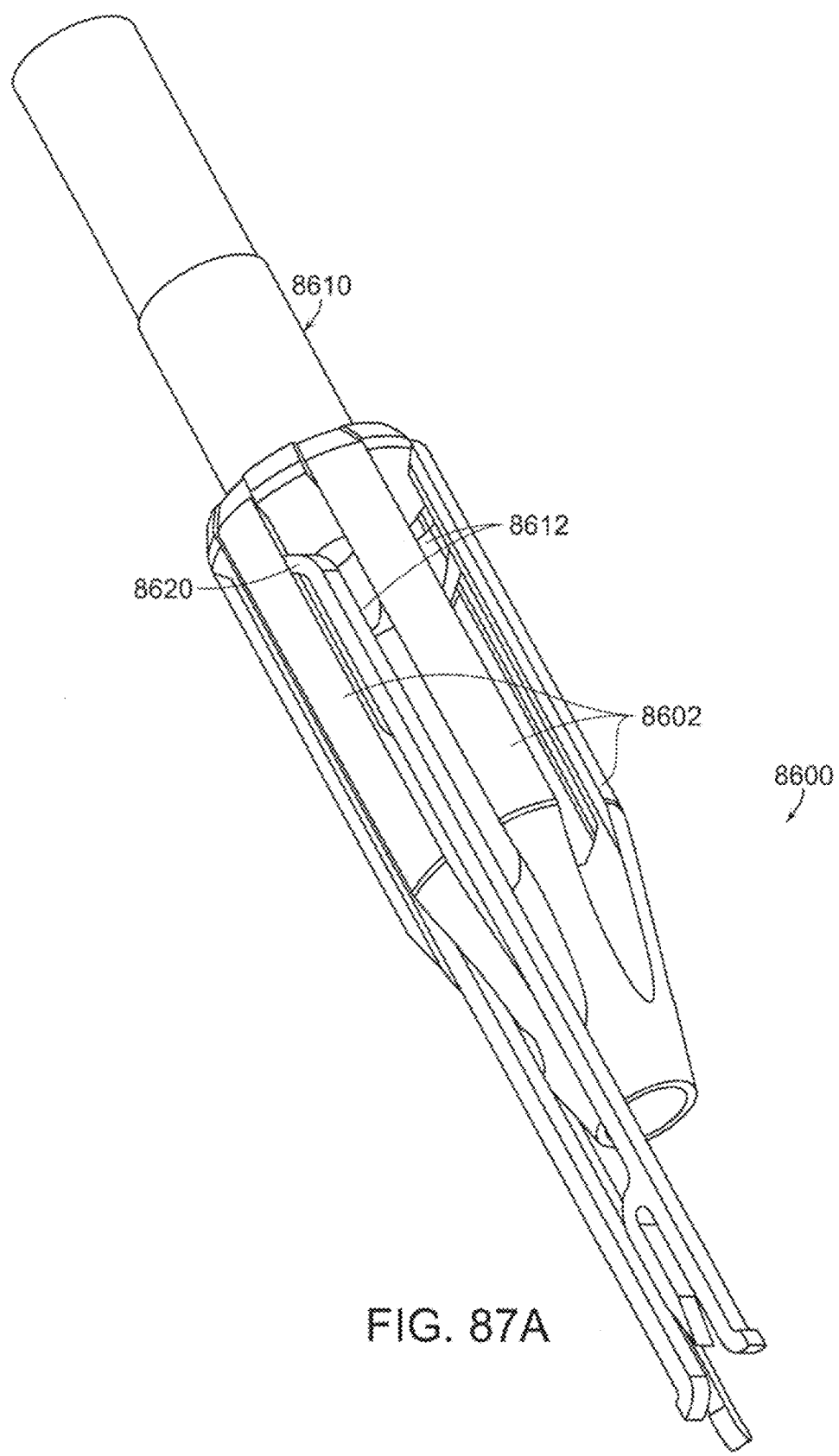

As can be seen in the inset of FIG. 57A, support member 5740 includes a hypo-tube 5742 and a support tube 5744 within the hypo-tube 5742. Hypo-tube 5742 typically is formed of stainless steel, while support tube 5744 typically is formed of nylon, such as VESTAMID®. Hypo-tube 5742 is fixed to the handle body, such as at proximal end cap 5544, as shown in FIG. 56 (also shown as end cap 3350 in FIG. 33). Also shown in the inset to FIG. 57A, but not part of support member 5740, are elongate member 8614, which is connected to distal apex capture portion 8610, and lumen 8613, which is connected to proximal apex capture portion 8600a, all of which are shown in FIG. 86D.

Figure 63:
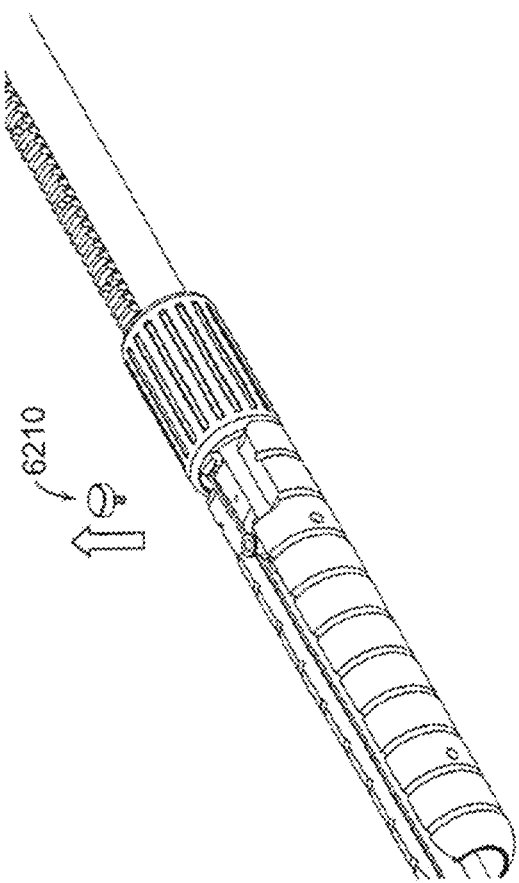
FIG. 63 is an embodiment of a delivery system of the invention.
Figure 62:
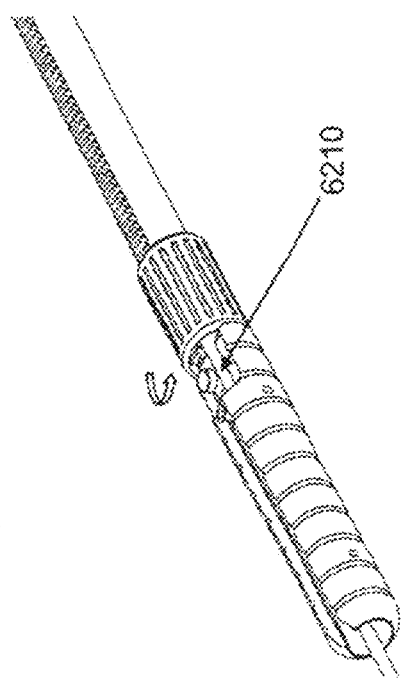
FIG. 62 is an embodiment of a delivery system of the invention.
Figure 65:
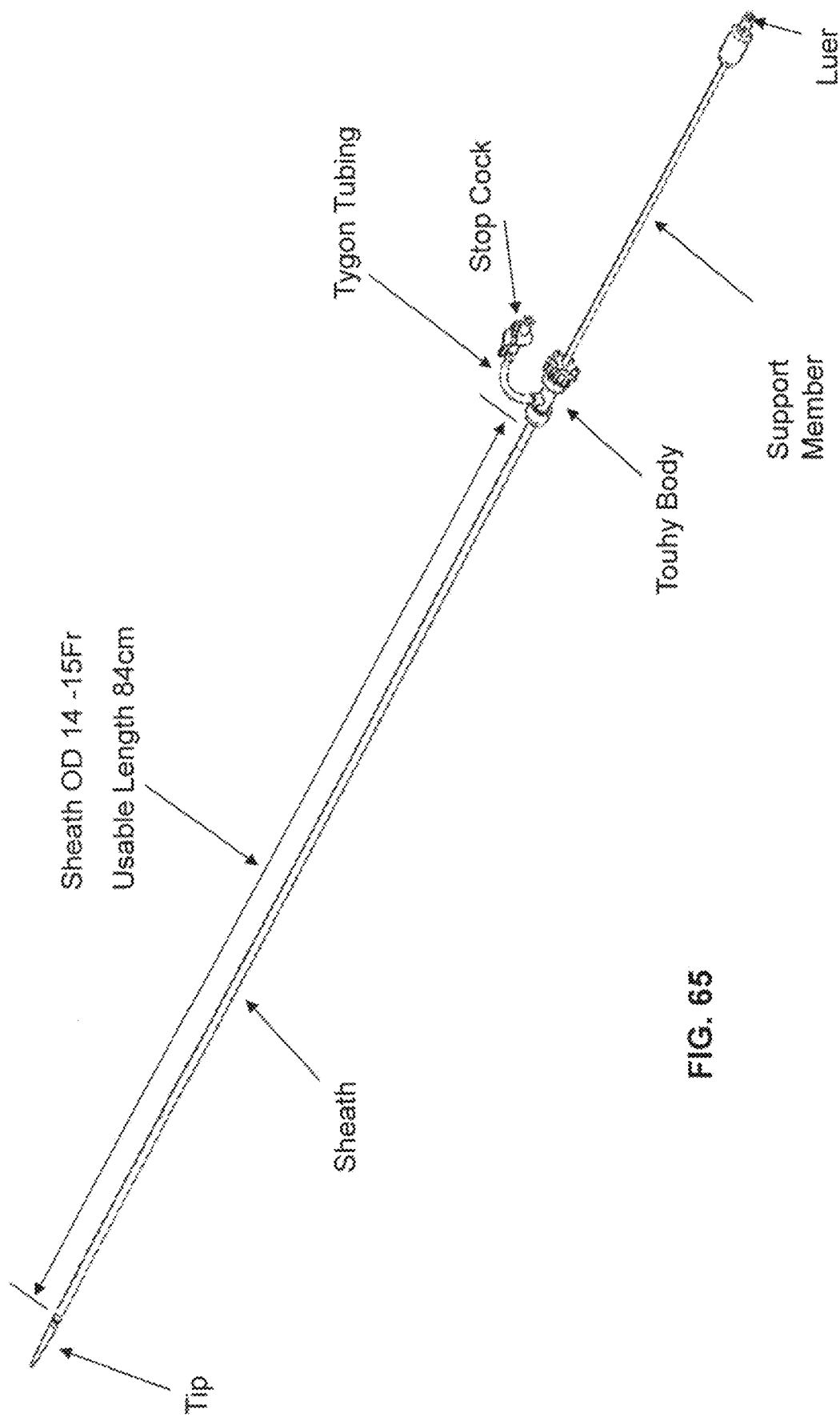
FIG. 65 is an additional embodiment of the delivery system of the invention. An exemplary length of the sheath can be 84 cm.
Figure 66:
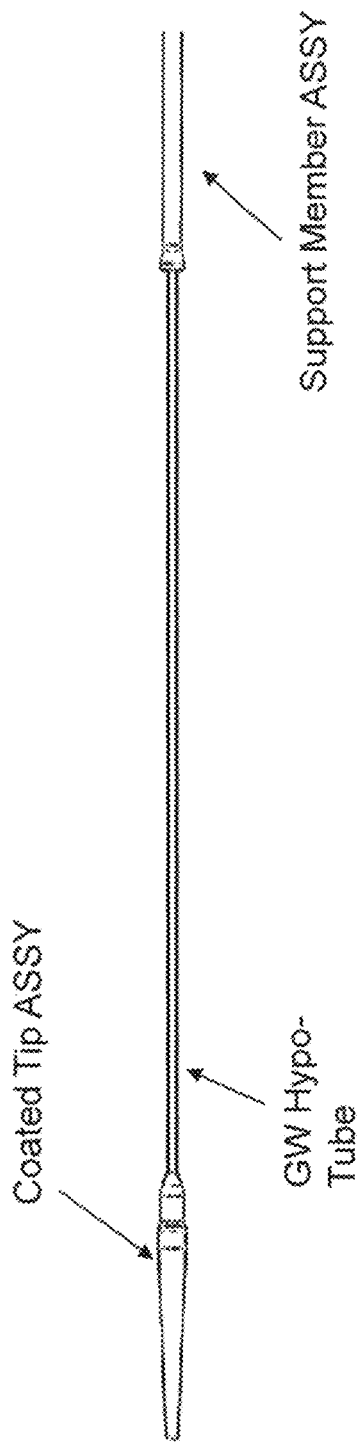
FIG. 66 is an additional embodiment of the delivery system of the invention that includes a tip assembly (ASSY), support member assembly (ASSY) and a guidewire (GW) hypo-tube.
Figure 67:
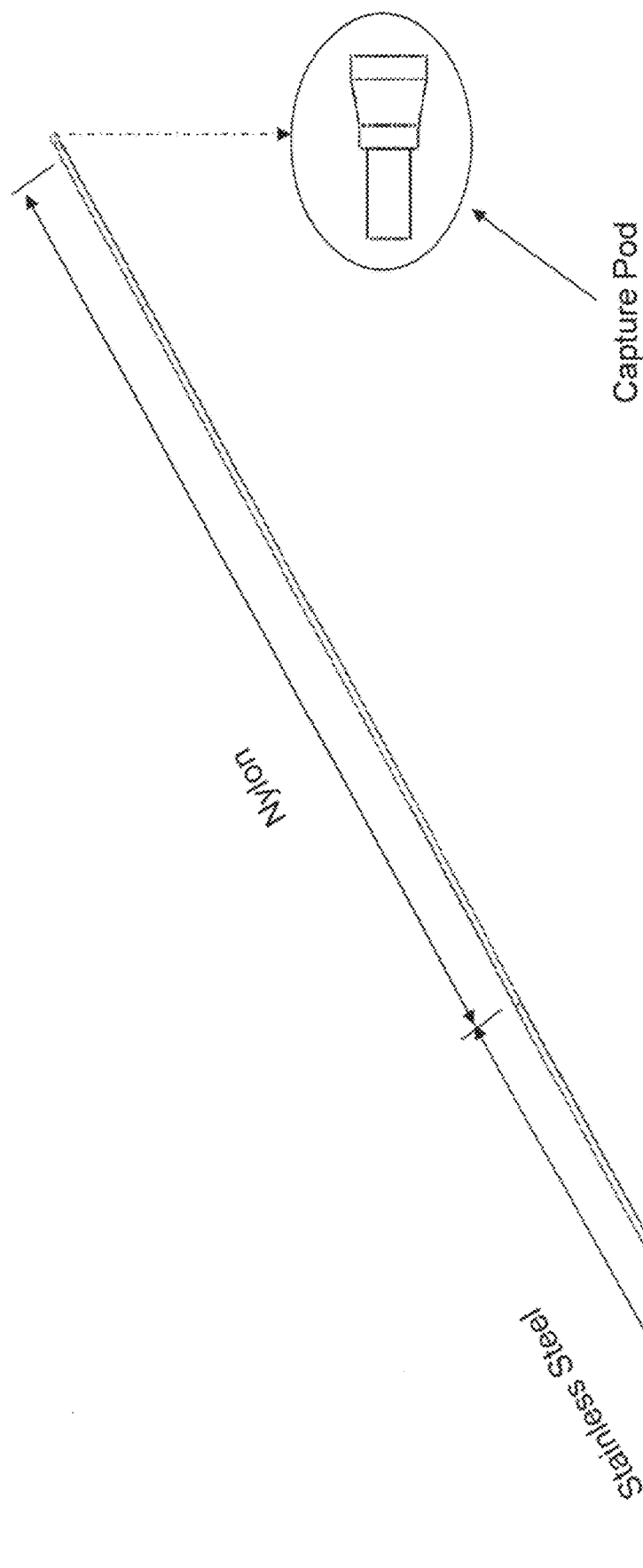
FIG. 67 is an additional embodiment of the delivery system of the invention that employs, for example, stainless steel and nylon.
Figure 68:
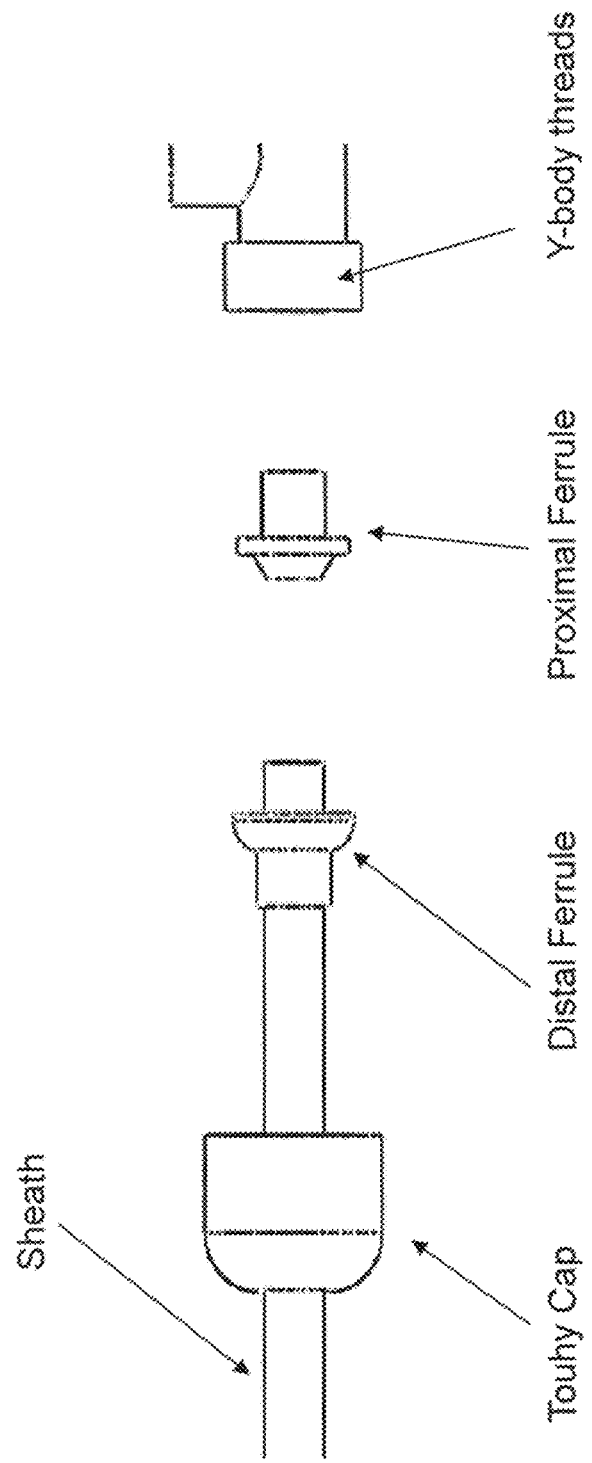
FIG. 68 is an additional embodiment of the delivery system of the invention.

The stent graft delivery system of the invention can further include a slider 5700. The slider 5700 of the stent graft delivery system comprises a slider body 5720 defining a central orifice through which the support member 5740 extends and a flush valve orifice 5712 extending substantially normal to the central orifice, the slider body 5720 being detachably fixable to the internal lead screw assembly 5510 (FIG. 55A by suitable means, such as, for example, release pin 6210, which extends through internal lead screw assembly into slider, as shown in FIGS. 62 and 63); a slider cap 5710 coupled to a distal end of the slider body 5720, the slider cap 5710 defining a central orifice that is substantially aligned with the central orifice of the slider body 5720 and through which the support member 5740 extends; a sheath valve knob 5790 threadably coupled to slider body 5720, an outer sheath 5550 extending from a distal end of the slider cap 5710, the outer sheath 5550 defining a lumen that is substantially aligned with the central opening of the slider body 5720 and through which the support member 5740 extends; a wiper valve 5750 at the central opening of the slider body proximal to the flush valve orifice 5712, the wiper valve 5750 forming a seal about the support member; an x-valve 5760 at the central opening of the slider body proximal to the wiper valve 5750, the x-valve 5760 forming a seal about a guidewire within support tube 5744 upon withdrawal of the support member from the slider body 5720; and a sheath valve 5770 at the central opening of the slider body 5720 and proximal to the x-valve 5760, the sheath valve 5770 being operable by activation of knob 5790 to seal the central opening.

In an embodiment, the x-valve 5760 includes a nitinol gasket as shown in FIGS. 57B through 57F.

"Proximal" means, when reference is made to a delivery system or a component of a delivery system, such as an apex capture device, a slider for a stent graft delivery system or a leg clasp, closest to the clinician using device. Likewise, "distal" means, when reference is made to a delivery system or a component of a delivery system, such as an apex capture device, a slider for a stent graft delivery system or a leg clasp, away from the clinician using the device.

When reference is made to a "stent" or a "stent graft system," "proximal" means that end of the stent or stent graft system that is towards the heart of the patient and "distal" means that end of the stent or stent graft system that is away from the heart of the patient.

In another embodiment, the invention is a slider 5700 for a stent graft delivery system, the slider 5700 comprising a slider body 5720 defining a central orifice through which a support member 5740 extends and a flush valve orifice 5712 extending substantially normal to the central orifice, the slider body 5720 being detachably fixable to an internal lead screw assembly 5510 (FIGS. 55 and 56); a slider cap 5710 (FIG. 57A) coupled to a distal end of the slider body, the slider cap 5710 defining a central orifice that is substantially aligned with the central orifice of the slider body 5720 and through which the support member extends; a knob 5790 threadably coupled to slider body 5720, an outer sheath 5550 extending from a distal end of the slider cap 5710, the outer sheath 5550 defining a lumen that is substantially aligned with the central opening of the slider body 5720 and through which the support member 5740 extends; a wiper valve 5750 at the central opening of the slider body 5720 proximal to the flush valve orifice 5712, the wiper valve 5750 forming a seal about the support member 5740; an x-valve 5760 at the central opening of the slider body 5720 proximal to the wiper valve 5750, the x-valve 5760 forming a seal about a guidewire within control tube 5744 upon withdrawal of the support member 5740 from the slider body 5720; and a sheath valve 5770 at the central opening of the slider body 5720 and proximal to the x-valve 5760, the sheath valve 5770 being operable by activation of the knob 5790 to seal the central opening.

FIGS. 61-64B are embodiments of a delivery system of the invention.

Figure 2:
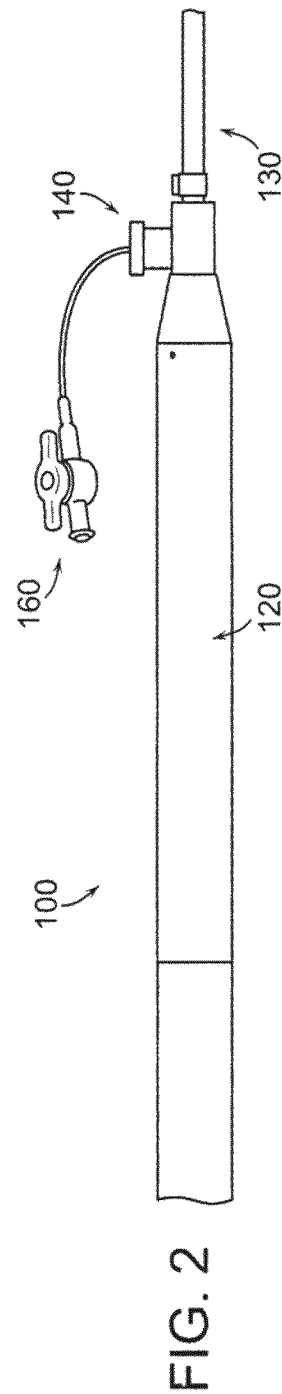
FIG. 2 represents an embodiment of a delivery system of the invention.
Figure 3:
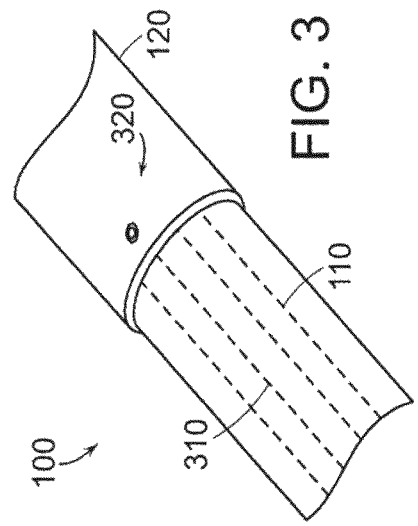
FIG. 3 represents an embodiment of a delivery system of the invention.
Figure 16:
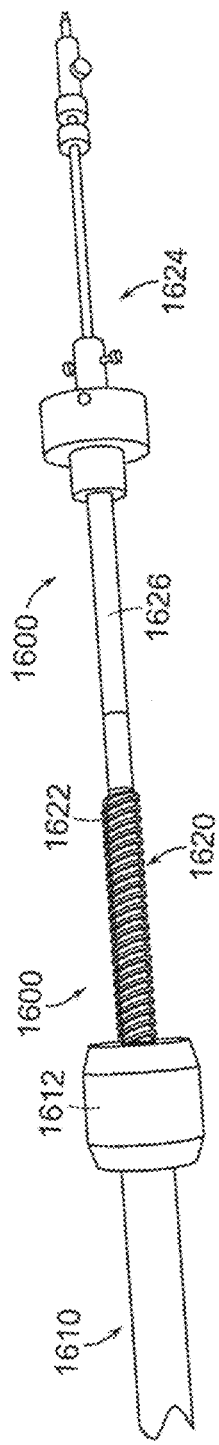
FIG. 16 is another embodiment of the delivery system of the invention.
Figure 17:
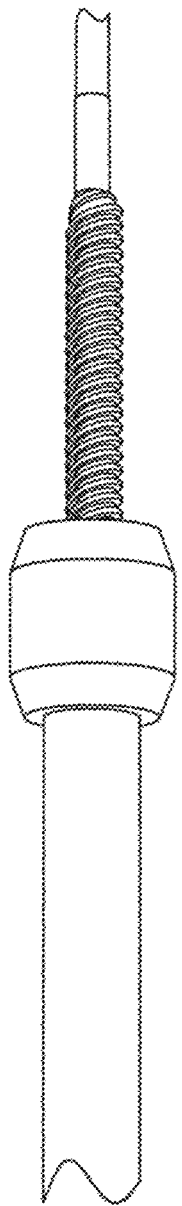
FIG. 17 is another embodiment of the delivery system of the invention.
Figure 19:
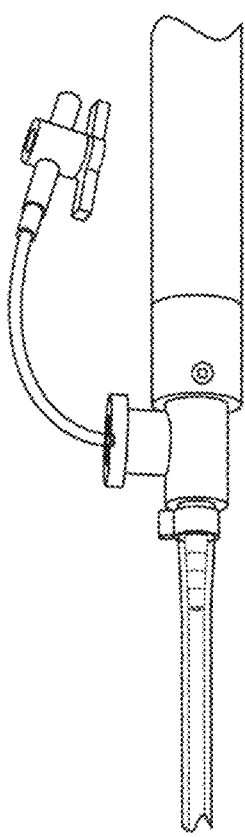
FIG. 19 is another embodiment of the delivery system of the invention.
Figure 18:
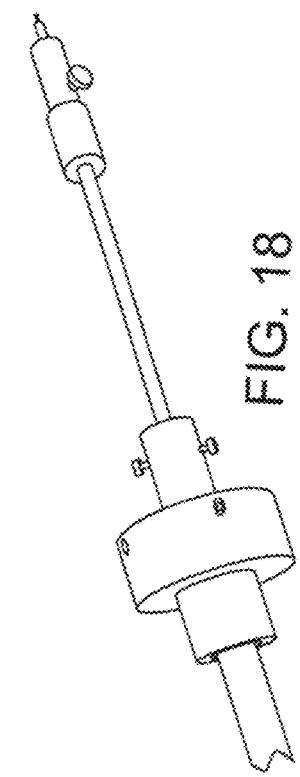
FIG. 18 is another embodiment of the delivery system of the invention.

Referring now to FIGS. 1 to 3, an exemplary embodiment of an improved pin-and-pull delivery system 100 according to the present invention is shown. The pin-and-pull delivery system 100 provides an inner lumen or secondary handle 110 that is slidably disposed within an outer sheath control lumen or outer handle 120. This configuration of the lumens 110, 120 can also be referred to as a telescopic assembly. The outer sheath control lumen 120 is longitudinally and rotationally fixed to a sheath 130 that is used to house the non-illustrated stent graft.

In an exemplary embodiment, the outer sheath control lumen 120 is an aluminum tube attached to a sheath hub 140, which is attached to the sheath 130. The inner lumen 110 is polycarbonate tube having a longitudinally cut slot 310 (e.g., see FIG. 3). The inner lumen 110 is longitudinally and rotationally fixed to a pushrod 150 (e.g., a stainless steel hypo-tube). By attaching the outer handle 120 to the sheath hub 140, the secondary handle 110 can be retracted into the outer handle 120 and will maintain rotational alignment of the handles 110, 120 by the presence of a setscrew 320 engaged in the slot 310. The groove and set-screw configuration will prevent the sheath 130 from rotating when the stent graft is deployed, which movement undesirably twists the prosthesis from a desired implantation position. This device is beneficial when used with a detachable sheath because the hemostasis 160, over the push rod 150, is in front of the handle mechanism 110, 120.

FIGS. 4 to 6 illustrate how the delivery system of FIGS. 1 to 3 can be used to implant a bifurcated stent graft. When the compressed bifurcated stent graft 410 is positioned at a target site, the delivery system is pinned with respect to the patient. The outer handle 120 is drawn proximally from the position shown in FIG. 4 to the position shown in FIG. 5. With the outer handle 120 in the fully retracted position (FIG. 5), the stent graft 410 is almost completely deployed in the patient's vessel. The only remaining control of the stent graft 410 is the releasable grasping of bare stent apices 412 by the apex capture device 510 of the delivery system.

Control of the capture device 510 occurs from the proximal-most end of the pushrod 150. One exemplary embodiment of the apex capture device 510 and its control assembly is disclosed in the family of applications beginning with U.S. Provisional Patent Application Ser. No. 60/499,652, filed Sep. 3, 2003, and U.S. patent application Ser. No. 10/784,462, filed Feb. 23, 2004, which applications and the entire family thereof is hereby incorporated by reference herein in its entirety. In such an embodiment, a non-illustrated control rod internal to the pushrod 150 is moved relative (arrow A in FIG. 6) to the pushrod 150 to separate the tines grasping one or more of the exposed bare stent apices 412 from control surfaces. This movement creates a gap therebetween to free the apices 412 from their controlled capture.

An alternative embodiment to that illustrated in FIGS. 5 and 6 is shown in FIGS. 7 to 9. This handle 700 improves the control and accuracy of deployment of the stent graft by adding mechanical advantage to the retraction of the introducer outer sheath. Mechanical advantage allows for a "smooth" retraction of the outer sheath by not allowing the build up of potential energy, stored in the compressed stent graft, to cause an unexpected jumping or jerking motion during outer sheath retraction. More specifically, the handle 700 has two interconnecting parts: a hollow outer sheath handle 710 and an inner screw handle 720. The proximal end of the outer sheath handle 710 has an interior cavity for receiving therein the distal end of the inner screw handle 720.

One exemplary embodiment for connecting the outer sheath handle 710 to the inner screw handle 720 is illustrated in FIGS. 10 and 11. A thread engagement portion 712 of the sheath handle 710 has two opposing thread engagement devices 714, 716 longitudinally offset from one another as illustrated in FIG. 10. One of the devices 714 can be, for example, a ball screw, and the other device 716 can be a set screw. The inner surface of the outer hollow sheath handle 710 is smooth in this particular embodiment. Engagement of the outer sheath handle 710 to the threads 726 of the inner screw handle 720 is made by having the devices 714, 716 ride in the threads of the inner screw handle 720. Thus, turning of the inner screw handle 720 causes the outer sheath handle 710 to retract over or extend from the distal end of the inner screw handle 720 in a controlled fashion. Turning can be assisted with a proximal turn knob 722 rotationally fixed to the inner screw handle 720.

Threads 726 extends for a longitudinal length that is greater than the amount that is necessary to overcome the greatest force required for stent graft deployment. Once that greatest point of force is overcome, the chance of handle jerk or slippage decreases and, therefore, the two handle portions 710, 720 can be moved longitudinally freely with respect to one another. To achieve the transition from longitudinal controlled and slow movement to longitudinal free movement (and speedy if desired), at the proximal end of the threads of the inner screw handle 720, screw channels 724 can be cut into the handle body to allow the threaded engagement device 716 to fall into one of the channels 724 and the threaded engagement device 714 to fall into the other channel (not illustrated) on the opposite side of the screw handle 720. A threaded engagement device 714 can be, for example, a ball screw, which would be desirable in this configuration because it can be used to center the threads against the relatively harder threaded engagement device 716, such as a set screw. Changing the force the devices 714, 716 impart against the threads can be accomplished by adjusting the tension on a ball of the ball set screw or by decreasing the depth of a set screw into the handle 710.

Functioning of the handle 700 is illustrated, for example, in the diagrams of FIGS. 12, 13, 14, 15A, 15B, 15C and 15D. Before the inner screw handle 720 is turned to retract the outer sheath handle 710, the outer sheath lumen 1210 completely covers the stent graft 1220, which is loaded therein just behind (proximal of) the nose cone 1230. The turn knob 722 is rotated to move the outer sheath handle 710 proximally and begin to deploy the stent graft 1220 from the outer sheath lumen 1210. The user holds the inner screw handle 720 longitudinally stationary while turning so that the outer sheath lumen 1210 moves proximally. This step is shown in FIG. 13. Once the threads 726 (FIG. 12) are completely disengaged from the thread engagement portion 712 of the sheath handle 710, the outer sheath handle 710 will rotationally lock into the channels 724 while still being longitudinally free to move with respect to the inner screw handle 720. At this point, the bare stent 1310 and the first sealing stent 1320 are exposed. After channel lock occurs, the proximal end of the stent graft 1220 is exposed from the outer sheath lumen 1210 as shown in FIG. 13. With the opposing threaded engagement devices 714, 716 (FIG. 11) locked into the channels 724 (FIG. 12), the outer sheath handle 710 can no longer rotate with respect to the inner screw handle 720 and, now, can be moved proximally as desired by the user. Accordingly, the outer sheath lumen 1210 can be retracted so that the entire body of the stent graft 1220 is exposed as shown in FIG. 14. At this point, the outer sheath handle 710 is positioned over the inner screw handle 720 and up to the turn knob 722 and the stent graft 1220 is only held to the delivery system 700 by the apex clasp device 1410. With release of the apex clasp device 1410, the stent graft 1220 is released from the delivery system 700 and, thereafter, the delivery system 700 can be removed from the patient without impacting the implantation of the stent graft 1220.

The delivery system 700 of FIGS. 12, 13, 14, 15A, 15B, 15C and 15D can be loaded with a 28 mm×150 mm graft into a 19.5 French OD braided introducer sheath, for example. In this configuration, the delivery system can deploy the bifurcated stent graft 1220 utilizing the mechanical advantage applied by the screw mechanism to release the first section of the graft (bare stent 1310 and first sealing stent 1320). The remainder of the stent graft can, then, be deployed by the pin-and-pull assembly of the device after the threads 726 are disengaged. This configuration eliminates any requirement to have the physician actively disengage the threads.

Benefits achieved by the telescopic configurations shown in FIGS. 1 to 15 are illustrated with regard to FIGS. 15A, 15B, 15C and 15D. The pin-and-pull systems of the prior art experienced an undesired force to the inner stabilizing member during deployment because there is a tendency to flex where gripped thereon (FIGS. 15A, 15B, 15C and 15D). This flexing caused misalignment of the sheath hub and the inner stabilizing member, which, in turn, required the physician to increase deployment forces for retracting the outer sheath, thus, correspondingly increasing the force against the inner stabilizing member (a damaging cycle).

An alternative to the two-part controlled deployment of FIGS. 7, 8, 9, 10, 11, 12, 13, 14, 15A, 15B, 15C and 15D for connecting the outer sheath handle 710 to the inner screw handle 720 is illustrated in FIGS. 16 to 23. These figures illustrate a mechanical handle 1600 that aids in the controlled, accurate deployment of a stent graft. This configuration adds mechanical advantage to the retraction of the introducer sheath, which allows for a "smooth" retraction of the outer sheath by not permitting the build up of potential energy, stored in the compressed stent graft, to cause an unexpected jumping or jerking motion during outer sheath retraction.

A distal engagement portion 1612 of the outer sheath handle 1610 has an internally threaded bore for receiving therein a threaded portion 1622 of the inner screw handle 1620. In an exemplary embodiment, the distal engagement portion 1612 is made of DELRIN®. Engagement of the outer sheath handle 1610 to the inner screw handle 720 (FIG. 7) is made by turning the outer sheath handle 1610 with respect to the inner screw handle 1620. This causes the outer sheath handle 1610 to retract over or extend from the distal end of the inner screw handle 1620 in a controlled fashion. Turning can be assisted with a proximal turn knob 1624 rotationally fixed to the inner screw handle 1620.

The threaded portion 1622 extends for a longitudinal length that is greater than the amount that is necessary to overcome greatest force required for stent graft deployment. Once that greatest point of force is overcome, the chance of handle jerk or slippage decreases and, therefore, the two handle portions 1610, 1620 can be moved longitudinally freely with respect to one another. To achieve the transition from longitudinal controlled and slow movement to longitudinal free movement (and speedy if desired), at the proximal end of the threads of the screw handle 1620, a channel 1626 (or more channels, e.g., two opposing channels) can be cut into the inner screw handle 1620. A non-illustrated set screw is located at the distal engagement portion 1612 to protrude into the interior and engage the threaded portion 1622. When the two handle portions 1610, 1620 are rotated sufficiently far to move the interiorly projecting set screw proximal of the threaded portion 1622, the set screw will ride directly into the channel 1626 (or the set screws directly into the channels 1626). A set screw is desirable in this configuration because it can be used to increase and decrease tension for rotating the two handle portions 1610, 1620 with respect to one another. Changing the force imparted against the threaded portion 1622 can be accomplished by decreasing/increasing the depth of the set screw into the distal engagement portion 1612.

Functioning of the handle 1600 is illustrated, for example, in the diagrams of FIGS. 20 to 23. Before the inner screw handle 1620 is turned to retract the outer sheath handle 1610, the outer sheath lumen 2010 completely covers the stent graft 2020, which is loaded therein just behind (proximal of) the nose cone 2030. The turn knob 1624 is rotated to move the outer sheath handle 1610 proximally and begin to deploy the stent graft 2020 from the outer sheath lumen 2010. The user holds the inner screw handle 1620 longitudinally stationary while turning so that the outer sheath lumen 2010 moves proximally. An embodiment of the step is shown in FIG. 21. Once the channels 1626 are completely disengaged from distal engagement portion 1612 of the outer sheath handle 1610, the outer sheath handle 1610 will rotationally lock into the channel(s) 1626 while still being longitudinally free to move with respect to the inner screw handle 1620. At this point, the bare stent 2110 and the first sealing stent 2120 are exposed. After channel lock occurs, the proximal end of the stent graft 2020 is exposed from the outer sheath lumen 2010 as shown in FIG. 21. With the set screw(s) locked into the channel(s) 1624, the outer sheath handle 1610 can no longer rotate with respect to the inner screw handle 1620 and, now, can be moved proximally as desired by the user. Accordingly, the outer sheath lumen 2010 can be retracted so that the entire body of the stent graft 2020 is exposed as shown in FIG. 22. At this point, the outer sheath handle 1610 is positioned over the inner screw handle 1620 and up to the turn knob 1624 and the stent graft 2020 is only held to the delivery system 1600 by the apex clasp device 2210. With release of the apex clasp device 2210, the stent graft 2020 is freed from the delivery system 1600 and, thereafter, the delivery system 1600 can be removed from the patient without impacting the implantation of the stent graft 2020.

The delivery system 1600 of FIGS. 16 to 23 can be loaded with a 28 mm×150 mm graft into a 19.5 French OD braided introducer sheath, for example. In this configuration, the delivery system 1600 can deploy the bifurcated stent graft 2020 utilizing the mechanical advantage applied by the screw mechanism to release the first section of the graft (bare stent 2110 and sealing stent 2120). The remainder of the stent graft 2020 can, then, be deployed by the pin-and-pull assembly of the device after the threads 1626 are disengaged. This configuration eliminates any requirement to have the physician actively disengage the threads.

A further alternative to the two- or multi-part controlled deployment of FIGS. 7 through 23 is illustrated in FIGS. 24 through 32. In general, these figures describe a "jogged slot" handle that aids in the controlled, accurate deployment of a stent graft. As set forth above, handles to be used on the delivery system of an AAA device need to gain better control over placement accuracy and/or to better fixate the AAA graft during graft placement. The present invention provides a "jogged slot" (which can be configured in a similar manner as an automatic transmission shifter slot (i.e., stair steps)) to improve placement accuracy. The "jogged slot" in this example utilizes stent graft delivery system features described in the family of applications beginning with U.S. Provisional Patent Application Ser. No. 60/499,652, filed Sep. 3, 2003, and U.S. patent application Ser. No. 10/784, 462, filed Feb. 23, 2004, incorporated herein and including a slotted aluminum handle body, a distal handle grip, a proximal handle grip and the proximal clasp assembly. The invention, however, is not limited to this particular embodiment. If desired, the actuation knob can be replaced with an end cap that serves to fixate the internal hypotube.

Figure 26:
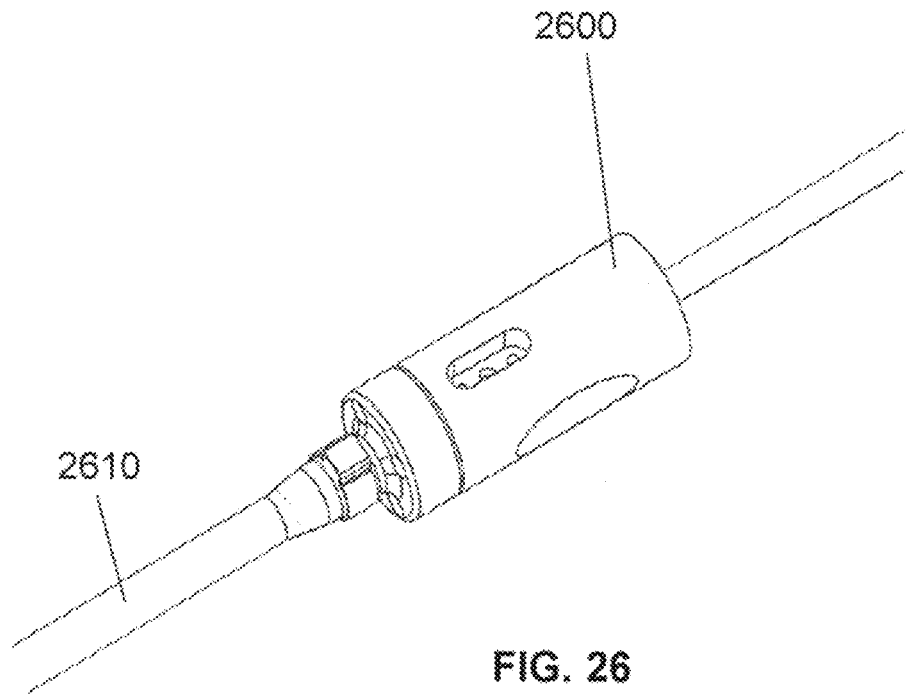
FIG. 26 is another embodiment of the delivery system of the invention.
Figure 27:
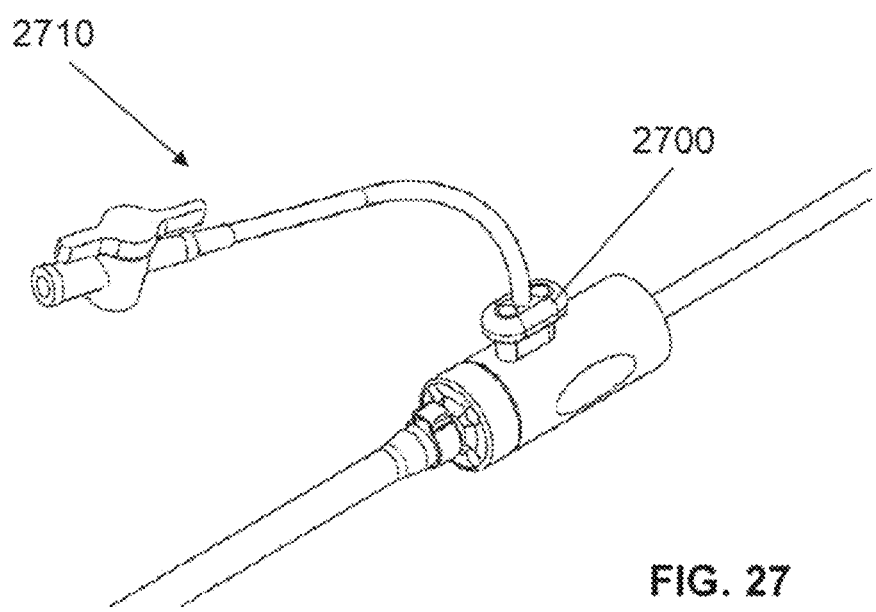
FIG. 27 is another embodiment of the delivery system of the invention.

As shown in FIGS. 24 and 25, the internal mechanism of the handle 2400 includes an internal tube 2500 with a jogged slot 2510 in which the slider assembly 2600 can slide from the distal portion of the handle 2500 (shown in FIG. 24) to the proximal portion of the handle during stent graft deployment. During deployment of the stent graft, the handle 2400 with the jogged slot 2510 only permits the handle parts to move to a particular extent that is less than the total movement required for complete deployment of the stent graft. The jog or "Z" 2512 in the slot 2510 has a circumferential or transverse portion 2514 preventing the proximal handle grip 2410 from moving all the way back to the end cap 2420 without first having to be rotated circumferentially/transversely around the jog 2512. FIGS. 26 and 27 show that the slider assembly 2600 can be, in an exemplary embodiment, a cylindrical hub with a barbed fitting at its distal end to receive the outer stent sheath 2610. At the proximal end of the slider assembly 2600 is an o-ring through which the support member hypotube passes. The slider assembly 2600 serves as both an attachment point for the outer stent sheath 2610 to the handle and as a hemostasis port for flushing of the sheath lumen. Exiting from the side of the slider assembly 2600 is a "boss" 2700 that extends outward, through the slot 2442 in the handle body 2440, and attaches to the proximal handle grip 2410. The flush port runs through this boss 2700 and attaches to the flush port tubing and valve 2710.

Figure 28:
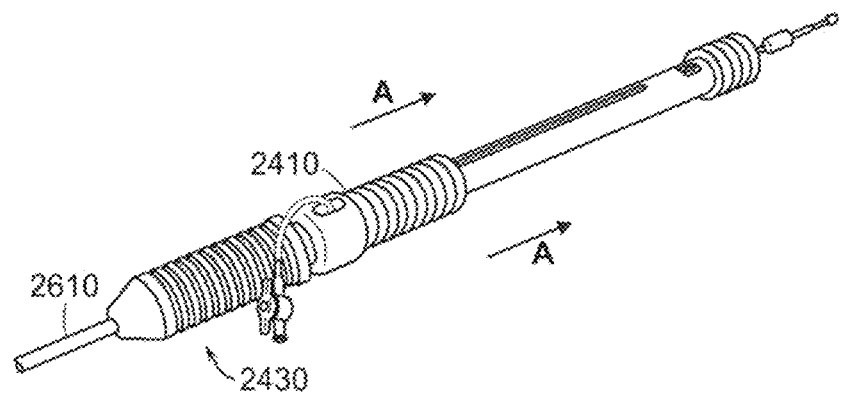
FIG. 28 is another embodiment of the delivery system of the invention.
Figure 29:
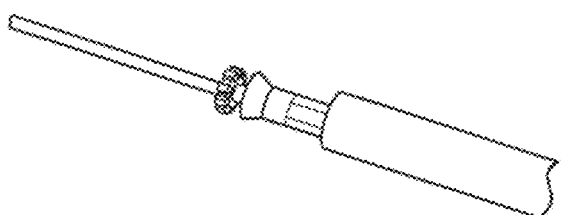
FIG. 29 is another embodiment of the delivery system of the invention. Arrow indicates a distal end of an inner support member.
Figure 30:
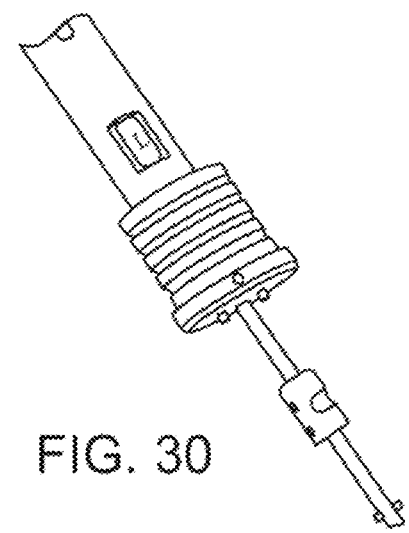
FIG. 30 is another embodiment of the delivery system of the invention. Arrow indicates proximal end of an inner support member.

FIGS. 28 to 30 illustrate the attachment of the slider assembly 2600 to the proximal handle grip 2410, which attachment allows actuation of the delivery system 2400 and deployment of the stent graft from the outer stent sheath 2610. The outer stent sheath 2610, which is attached to the slider assembly 2600, is retracted in a proximal sliding motion (indicated by arrows A in FIG. 28) over the stent graft. More specifically, in this exemplary embodiment, the distal handle 2430 is held stationary while the proximal handle grip 2410 is moved back (proximally) to deploy the stent graft. The internal support member that is located coaxially within the outer stent sheath 2610 (see FIGS. 29 and 30) serves as a platform or anchor to prevent the stent graft from retracting along with the outer stent sheath 2610.

Significantly, the internal tube 2500 of the handle 2400 provides advantages to permit controlled deployment (unsheathing) of the stent graft. The internal tube 2500 in this exemplary embodiment is made from polycarbonate material and is sized so that it can move freely within the slotted aluminum handle body 2440. The slider assembly 2600 is sized so that it can move freely within the internal tube 2500. The internal tube 2500 has a straight tube running the full length of the handle 2400. Machined through the wall of the internal tube 2500 is the slot 2510 which is "jogged" in the manner of an automobile transmission shifter. As such, the jogged slot 2510 provides a so-called stop 2514 (or stops) that control deployment of the stent graft at different points during the stent graft deployment sequence. The jog(s) 2512 that is/are cut into the internal tube 2500 only allows the slider assembly 2600 to move within that particular jog segment of the internal tube 2500. Further retraction of the outer stent sheath 2610 requires the user to actively turn the knob 2420 to a next setting, thus allowing further proximal movement of the slider assembly 2600. The boss 2700 of the slider assembly extends through the jogged slot 2510 of the internal tube 2500 and through the slot 2442 of the handle body 2440. The boss 2700 is, then, connected to the proximal handle 2410. The internal tube 2500 is attached at the distal end of the handle 2400 to the distal handle 2430. Rotation of the distal handle 2430 allows rotation of the internal tube 2500 within the handle body 2440.

Figure 31:
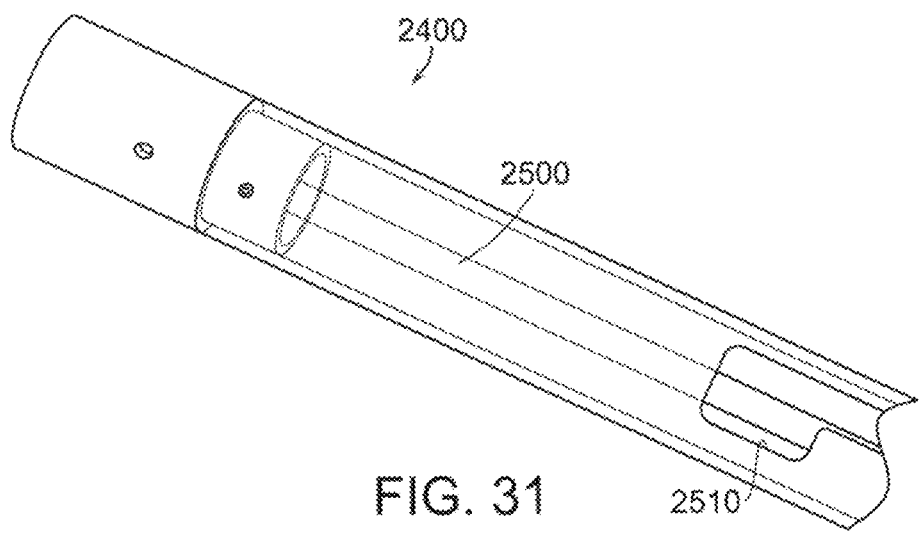
FIG. 31 is another embodiment of the delivery system of the invention. Arrow indicates component to attach internal tube to distal handle grip.
Figure 32:
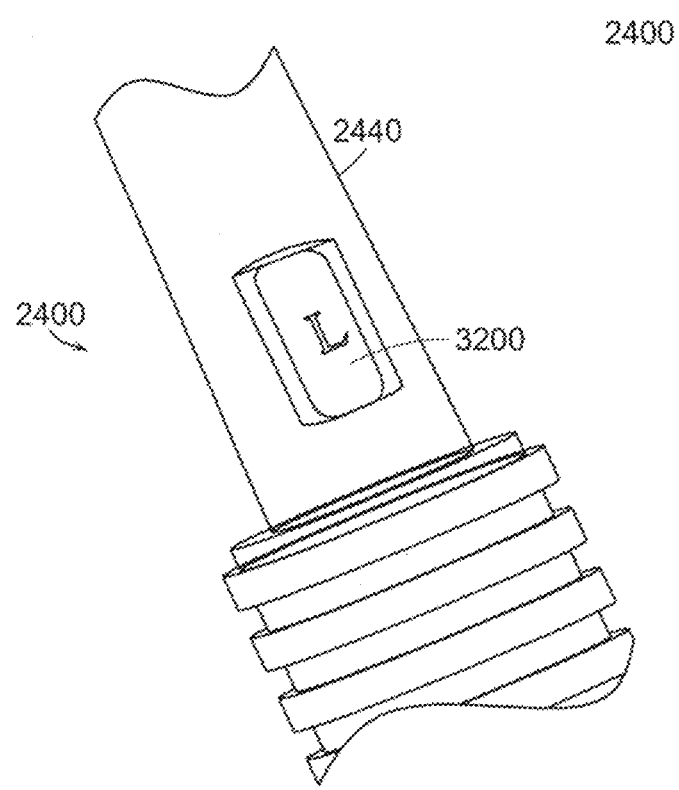
FIG. 32 is another embodiment of the delivery system of the invention. Arrow indicates stop position indicator in locked position.

FIGS. 31 and 32 show one exemplary embodiment for indicating a position of the internal tube 2500 in the various stop positions. The indicator can be realized through either a viewing window 3200 with numbers/letters or by color coded dots. From the package in which the system is delivered, the handle 2400 can be in a locked position (indicated, for example, with an "L") of the jogged slot 2510. In this orientation, the clinician could remove the handle 2400 from the package and perform flushing procedures without a concern of prematurely deploying the stent graft during handling. The clinician keeps the handle 2400 in the locked position/state during insertion of the device into the patient's artery and while tracking to the site of stent graft deployment. The stop mechanism prevents any possibility of inadvertent proximal movement of the outer sheath 2610, which could partially deploy the stent graft.

Once the clinician identifies the deployment site and is ready to deploy the stent graft, he/she turns the distal handle 2430 until, for example, stop position 1 is obtained. With the device in stop position 1, the slot 2510 of the internal tube 2500 and the slot 2442 of the handle body 2440 will be aligned, thus allowing the proximal handle 2410 to be slid proximally to allow partial stent graft deployment. Positioning of the next exemplary jog or stop on the internal tube 2500 is set so that the supra-renal struts and at least two stent graft springs (i.e., stents) are deployed from the outer sheath 2610. With the stent graft partially deployed, but with the suprarenal struts (i.e., of the bare stent) still captured in the distal clasp mechanism, the stent graft can still be maneuvered proximally or distally within the aorta to establish sealing site positioning.

At this point, the clinician can fix the handle 2400 relative to the patient to maintain the stent graft position relative to the aorta. Then, the clinician can move the distal handle 2430 to stop position 2 and continue to move the proximal handle 2410 in a proximal direction until, for example, the contralateral leg of a bifurcated stent graft is released from the outer sheath 2610. The stop on the handle 2400 at the end of stop position 2 can, in an exemplary embodiment, prevent the ipsilateral leg from deploying from the outer sheath 2610. Then, the clinician can rotate the handle 2400 to orient the stent graft's contralateral leg to align with the patient's arterial anatomy. Once the stent graft is oriented properly, the clinician can actuate the distal clasp assembly and release the suprarenal struts. The captured ipsilateral leg, along with the anchored supra-renal strut and proximal seal serve as fixation during crossing of the guidewire into the contralateral leg and subsequent placement of the contralateral leg graft placement. Once contralateral leg graft placement is achieved, the handle 2400 is moved to stop position 3 and the proximal handle 2410 is pushed proximally to fully release the stent graft. The particular placement/configuration of the stop positions is determined based upon various factors, including the size of the prosthesis and the features of the vessel in which the prosthesis is to be placed.

Yet another alternative to the multi-step controlled deployment of FIGS. 7 to 32 is illustrated in FIGS. 33 to 51. These figures describe, in general, an internal lead screw handle that aids in the controlled, accurate deployment of a stent graft. As indicated above, it is desirable to gain better control over placement accuracy of an AAA graft during stent graft placement with an AAA delivery system. The internal lead screw embodiment described herein increases placement accuracy by allowing the operator to have more control over the initial deployment of the stent graft.

Figure 33:
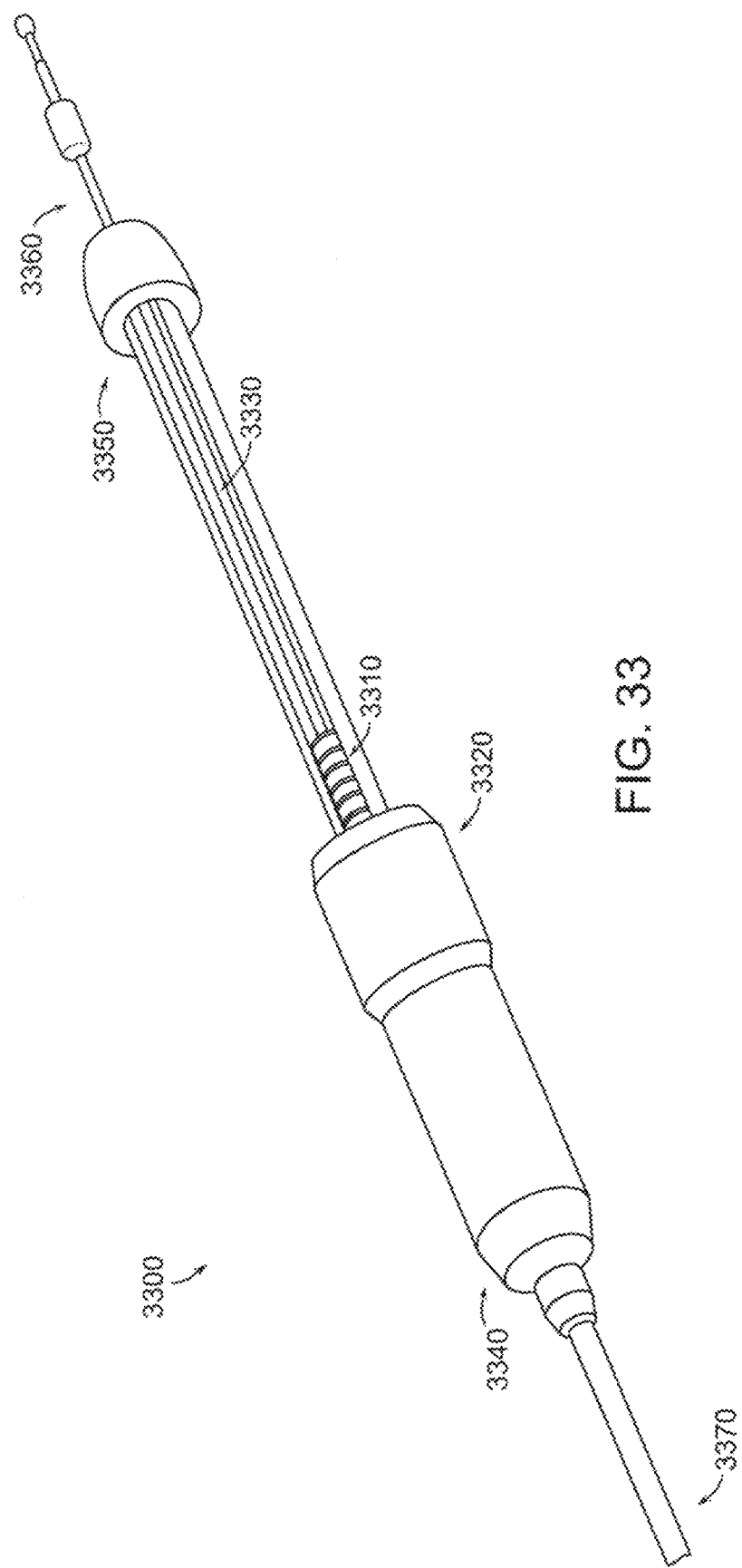
FIG. 33 is a further embodiment of the delivery system of the invention.
Figure 34:
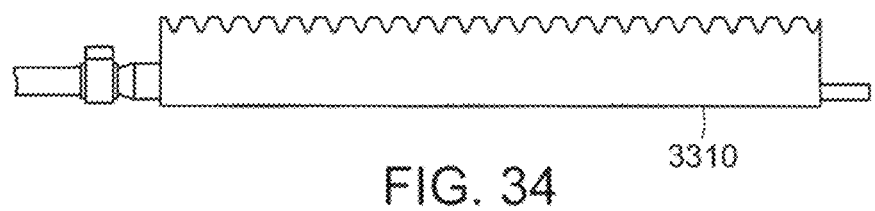
FIG. 34 is a further embodiment of the delivery system of the invention. Arrow indicates a side view of a lead screw.
Figure 51:
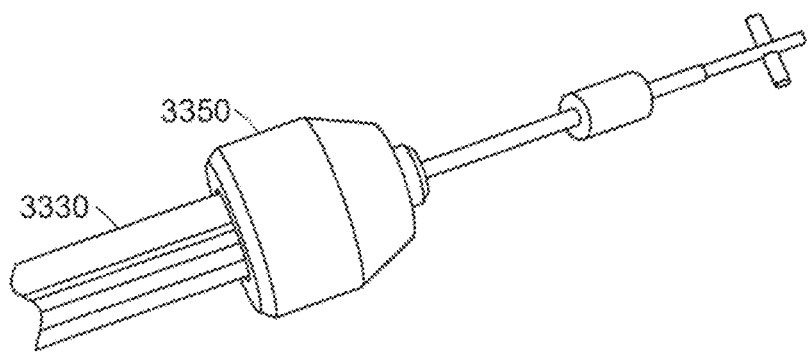
FIG. 51 is a further embodiment of the delivery system of the invention.

An exemplary embodiment of a delivery system 3300 with an internal lead screw that deploys a stent graft from a sheath is shown beginning with FIG. 33 and ending with FIG. 51. The delivery system 3300 has an internal lead screw 3310 (see FIGS. 34, 35, 37), a lead screw nut 3320 (see FIGS. 35 and 37), a lead screw rail 3330 (see FIGS. 36 and 37), a distal grip handle 3340, a flush port and a proximal end cap 3350. This configuration utilizes a support member 3360 with a hypotube at its proximal end and a distal clasp assembly similar to the stent graft delivery system described in the patent family previously incorporated herein by reference. The lead screw nut 3320 can be actuated in different ways to deploy the stent graft from the outer sheath 3370. One exemplary actuation rotates the lead screw nut slowly to pull back on the outer sheath 3370 using the threads of the internal lead screw 3310. Another exemplary actuation simply pulls back on the lead screw nut 3320 to deploy the stent graft. By housing the internal lead screw 3310 (which is formed, in this example, from cutting material on outer portions of a round threaded screw to a rectangular cross-section with threads on only one side, i.e., a partial lead screw) within the lead screw rail 3330, the system can bypass the need to always use the first exemplary actuation process.

The support member 3360 is coaxially contained within the delivery system 3300. The support member 3360 is attached at its proximal end to the proximal end cap 3350 of the handle 3300. The support member 3360 travels coaxially through the internal lead screw 3310, the flush port, and the outer sheath 3370. At the distal end of the support member 3360 is a capture pod that holds the proximal (caudal) end of the stent graft. A guidewire lumen and the distal clasp assembly tubing (FIG. 39) travel coaxially within the support member 3360 along the full length of the delivery system 3300. Contained within the distal end of the outer sheath 3370 can be the crimped stent graft and the distal clasp assembly. The distal clasp assembly terminates at the distal end with a flexible tip 4100, shown in FIG. 41.

Figure 35:
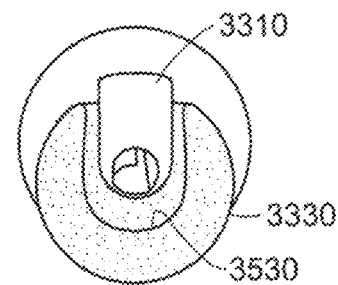
FIG. 35 is a further embodiment of the delivery system of the invention. Arrow indicates an end view of a lead screw.
Figure 36:
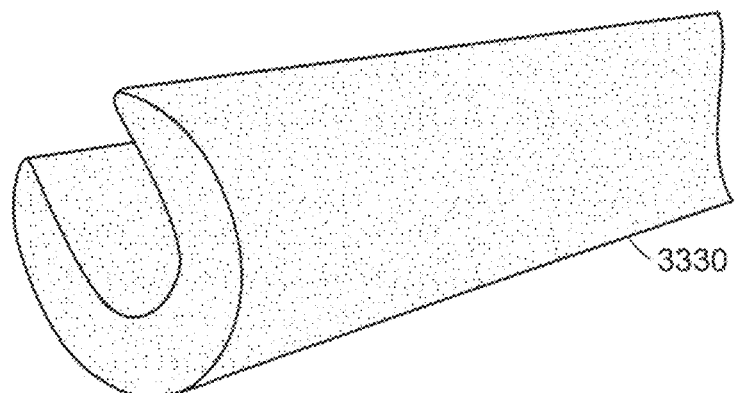
FIG. 36 is a further embodiment of the delivery system of the invention. Arrow indicates a lead screw rail.
Figure 37:
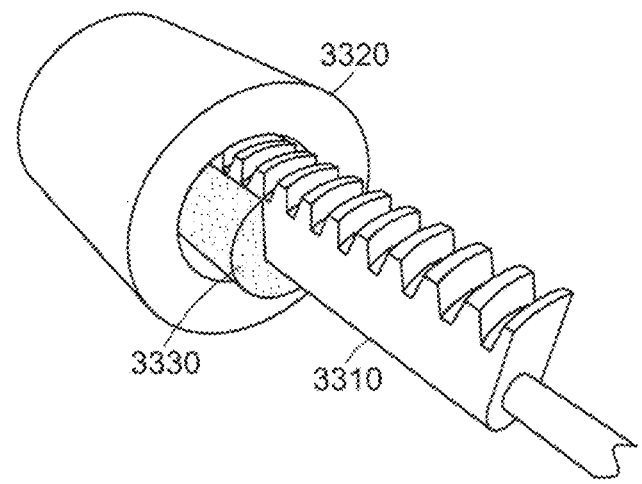
FIG. 37 is a further embodiment of the delivery system of the invention.

The lead screw 3310 (FIG. 33) used in this exemplary embodiment can be made from a 1-inch diameter lead screw with a 0.400 inch linear lead per rotation of the lead screw nut. The internal lead screw 3310 is approximately 14 cm in length and is machined so that most of the threads are cut away from the circumference. Machining of the internal lead screw 3310 is performed to allow the internal lead screw 3310 to fit in the lead screw rail 3330 and to allow the lead screw rail 3330 to fit between the internal lead screw 3310 and the lead screw nut 3320. The lead screw rail 3330 acts to center the lead screw nut 3320 on the partial internal lead screw 3310. The diameter of the lead screw rail 3330 is approximately equivalent to the minor diameter of the lead screw nut 3320. By locating the lead screw rail 3330 in this configuration, the internal lead screw 3310 can slide within the groove 3530 of the lead screw rail 3330 (FIG. 35).

Figure 38:
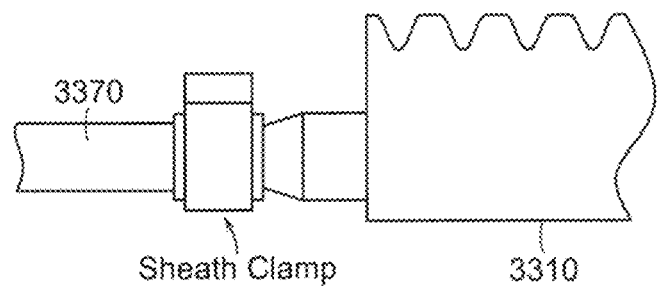
FIG. 38 is a further embodiment of the delivery system of the invention.
Figure 39:
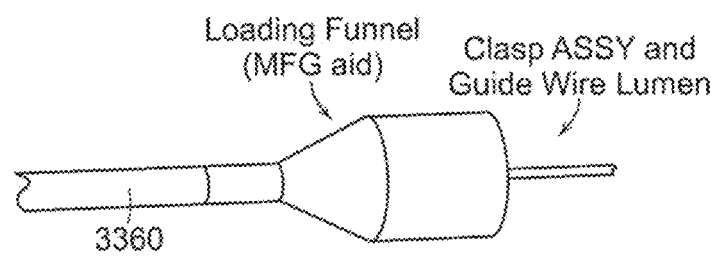
FIG. 39 is a further embodiment of the delivery system of the invention.
Figure 40:
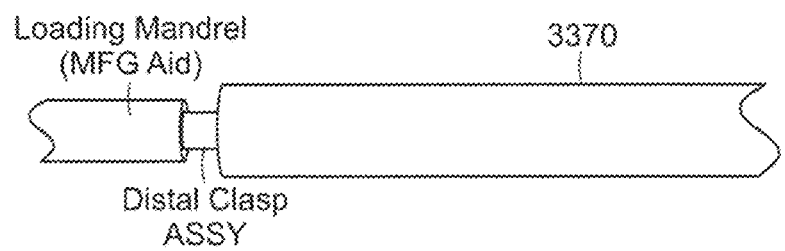
FIG. 40 is a further embodiment of the delivery system of the invention that includes a distal clasp assembly (ASSY) and a loading mandrel (manufacture (MFG) aid).
Figure 41:
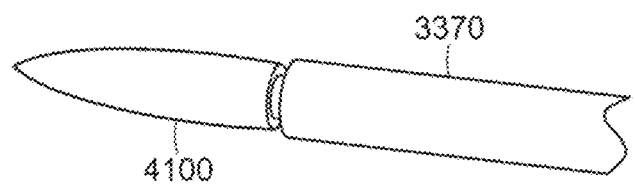
FIG. 41 is a further embodiment of the delivery system of the invention.

Attached to the distal end of the internal lead screw 3310 is a flush port (FIG. 38). An O-ring is contained in the proximal end of the flush port, which seals around the support member hypotube. At the distal end of the flush port is a nipple that attaches to the outer sheath 3370.

Figure 42:
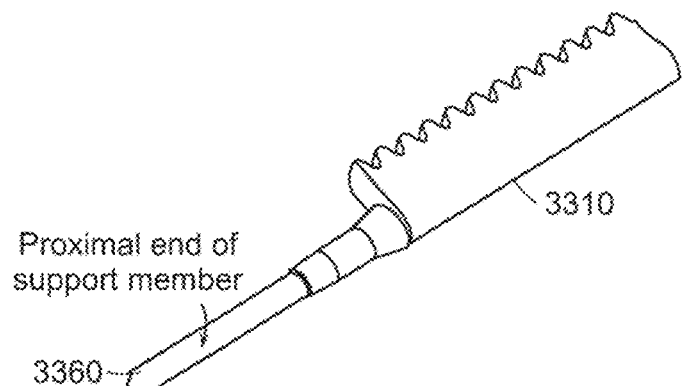
FIG. 42 is a further embodiment of the delivery system of the invention.
Figure 43:
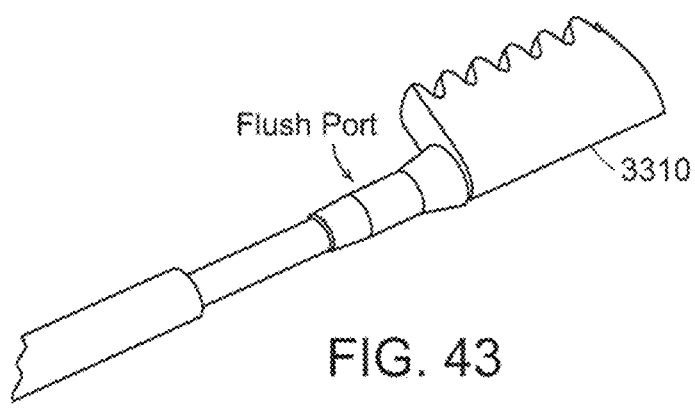
FIG. 43 is a further embodiment of the delivery system of the invention.
Figure 44:
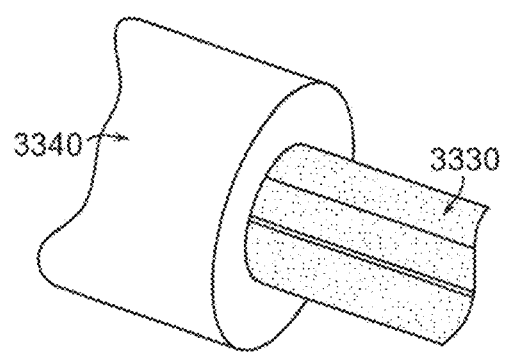
FIG. 44 is a further embodiment of the delivery system of the invention.
Figure 45:
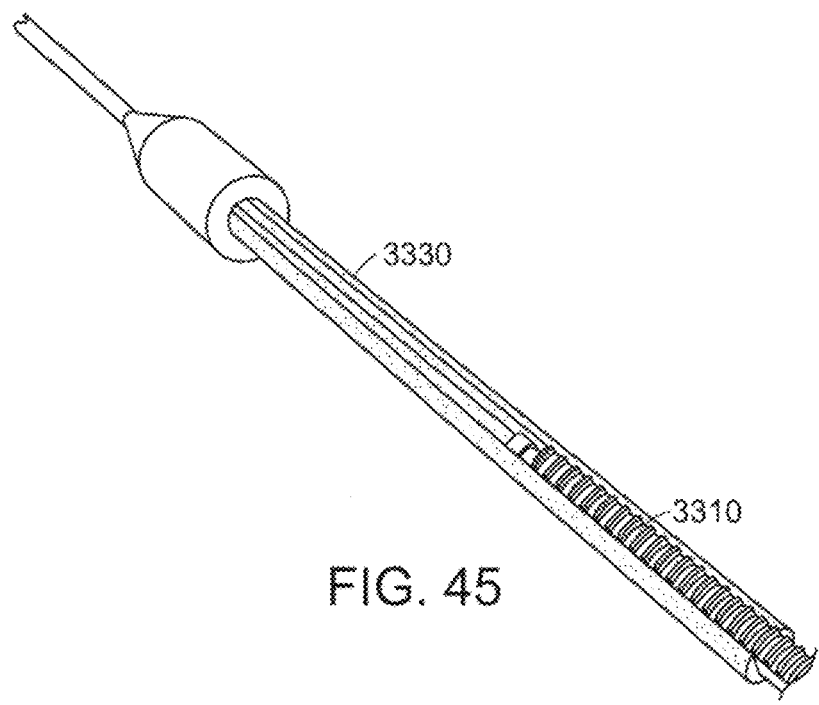
FIG. 45 is a further embodiment of the delivery system of the invention.
Figure 46:
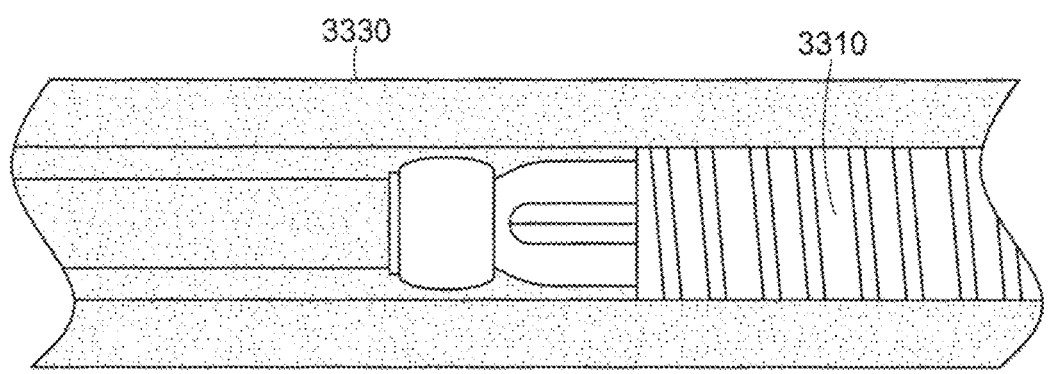
FIG. 46 is a further embodiment of the delivery system of the invention.
Figure 47:
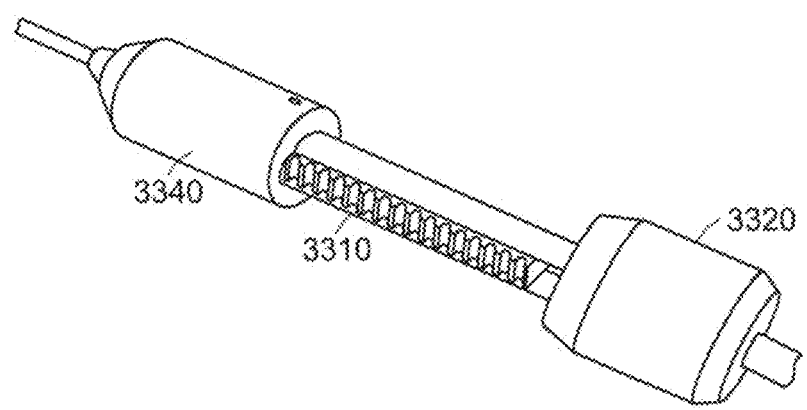
FIG. 47 is a further embodiment of the delivery system of the invention.
Figure 48:
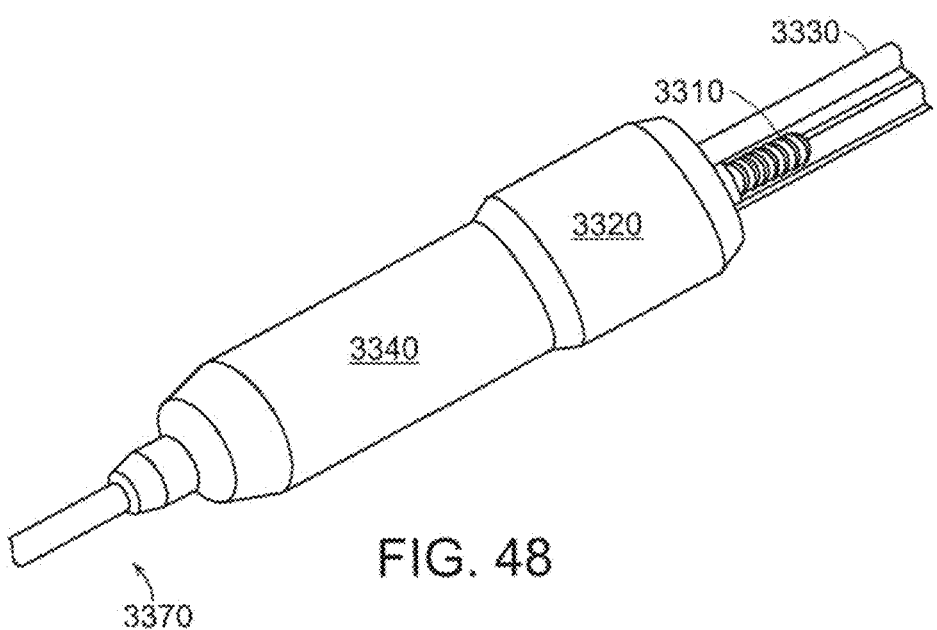
FIG. 48 is a further embodiment of the delivery system of the invention.
Figure 49:
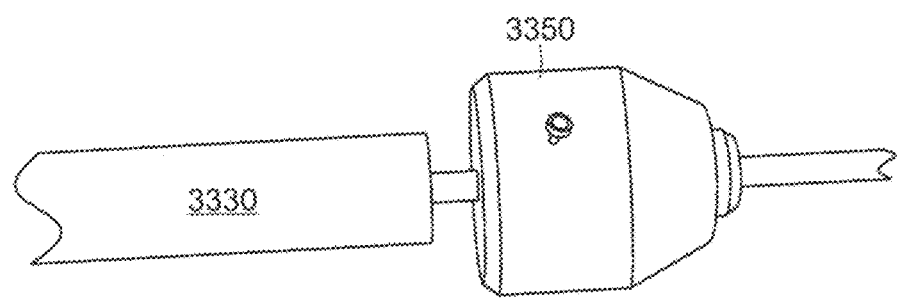
FIG. 49 is a further embodiment of the delivery system of the invention.
Figure 50:
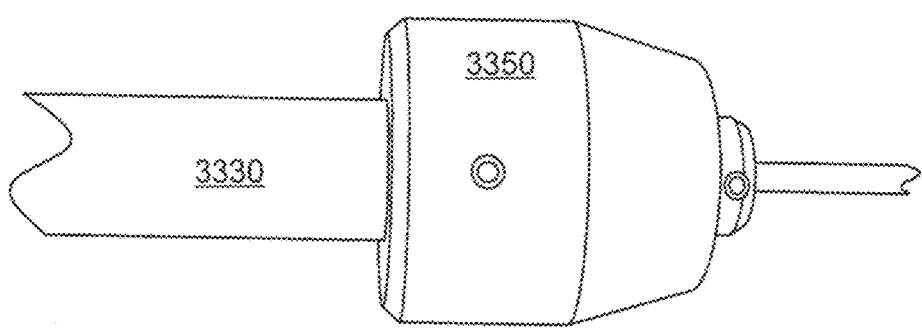
FIG. 50 is a further embodiment of the delivery system of the invention.

During assembly of the device 3300 (shown, in part, in FIGS. 39 to 41), the stent graft is first loaded into the outer sheath 3370 along with the distal clasp assembly and the guidewire lumen. Then, the distal tip 4100 is threaded onto the distal clasp assembly. As shown in FIGS. 42 and 43, the pre-assembled support member 3360 is then loaded into the outer sheath 3370. Then, the support member 3360 is guided through the flush port and the internal lead screw 3310. The outer sheath 3370 is, then, attached to the flush port and is clamped (see FIG. 38). As shown in FIG. 44, the handle body is assembled by first attaching the distal handle grip 3340 to the lead screw rail 3330. Then, as shown in FIGS. 45 to 46, the sub-assembly of the outer sheath 3370/flush port/internal lead screw 3310 is threaded through the opening in the front of the distal handle grip 3340 and the internal lead screw 3310 is set in the groove 3430 of the lead screw rail 3330. FIGS. 47 to 48 show that the lead screw nut 3320 is passed over the lead screw rail 3330 and mated with the internal lead screw 3310. The outer sheath 3370 is moved forward and the lead screw nut 3320 is threaded forward until it contacts the distal handle grip 3340. As illustrated in FIGS. 49 to 51, the proximal end cap 3350 is, then, placed over the support member 3360 and attached to the lead screw rail 3330. The support member 3360 is secured to the proximal end cap 3350 and the distal clasp mechanism hardware is installed.

In use, the clinician first flushes the system 3300 by forcing saline through the flush port. The saline fills the annular space between the outer sheath 3370 and the support member 3360, permeates through the crimped stent graft, and exits between the outer sheath 3370 and the flexible tip 4100. The o-ring in the flush port seals the hypotube of the support member 3360 and prevents leakage through the delivery system 3300. Then, the clinician feeds the delivery system 3300 over an indwelling guidewire and tracks the device to the stent graft deployment site.

At this point, the clinician has the option to either slowly release the stent graft by rotating the lead screw nut 3320 or rapidly release the stent graft by pulling back on lead screw nut 3320 and, thereby, sliding the lead screw 3310 down the rail 3330. At some point in the deployment of the stent graft, the release can be stopped to actuate the distal clasp assembly and release the leading struts (bare stent) of the stent graft. Because the stent graft is usually severely constrained within the outer sheath 3370, deployment forces with AAA devices can be quite high.

The internal lead screw of the invention has the advantage of incorporating a screw system to convert the linear force to a torque force. The torque force that the clinician must exert on the lead screw nut to deploy the stent graft is ergonomically less difficult than the linear pull force. In addition to the mechanical advantage obtained with the lead screw nut, the screw type mechanism allows for greater control in the release of the stent graft. In a linear pin-and-pull system, the largest force to deploy the stent graft is at the initial release of friction between the stent graft and the sheath. As soon as that initial friction is overcome, the deployment force quickly declines. From an ergonomic point of view, it is very difficult for a clinician to maintain control and speed of the deployment at the moment when the frictional forces are overcome. It is very common for the stent graft to be un-sheathed more than was desired due to this loss of control. A screw type mechanism according to the present exemplary embodiment allows the clinician to have more control over this initial release of the stent graft, which is a critical factor for stent placement accuracy.

Figure 52:
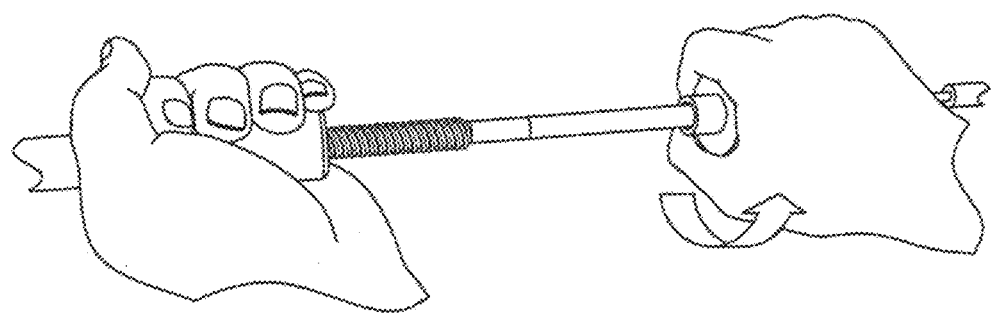
FIG. 52 is a lead screw embodiment of the invention.
Figure 53:
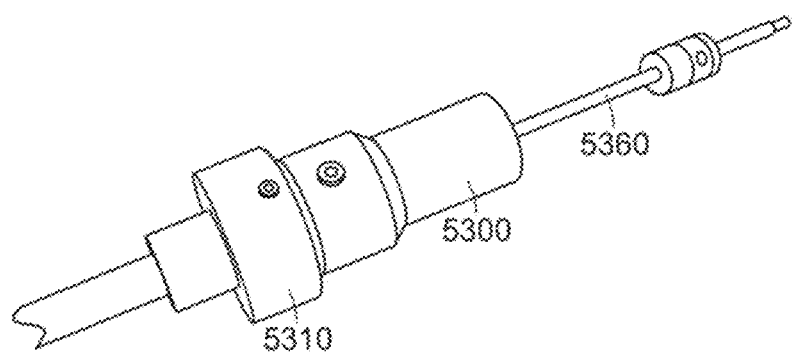
FIG. 53 is a lead screw embodiment of the invention.
Figure 54:
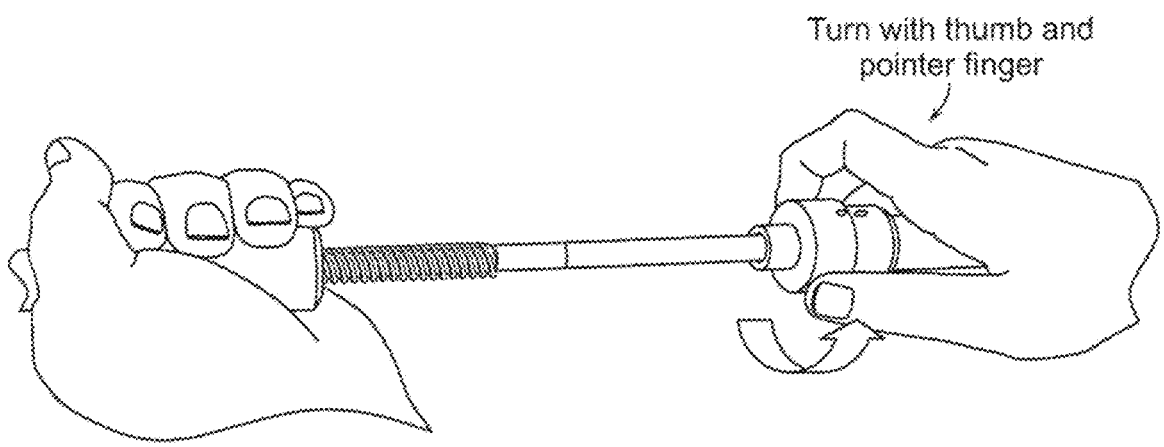
FIG. 54 is a lead screw embodiment of the invention.

FIGS. 52 to 54 illustrate an improvement to the lead screw embodiment of the previous figures. In the above embodiment, the user was required to grip and turn the handle knob with one hand while holding the sheath handle grip with the other hand. See FIG. 52. Actuation of this handle required the user to concentrate on two motions at once for deployment of the stent graft. Also, there was a possibility of turning the hypotube/inner member out of alignment with the sheath hub, which misalignment could decrease stent graft placement accuracy. Therefore, a second handle 5300 was added behind (proximal) the turn knob 5310 (FIGS. 53 and 54). The handle 5300 is attached to the bearing engagement that is affixed to the inner member 5360 (hypotube). The user grips the second handle 5300 and turns the lead screw knob with the thumb and pointer finger. Now, the user's hand is pinned in one location as the knob is turned and the sheath handle is retracted back over the lead screw.

FIGS. 55A through 57 illustrate another exemplary embodiment of the delivery systems of the present invention. This example of the delivery system 5500 includes features of the pin-and-pull telescopic systems 100, 700, 1600, 2400 and the system 3300. The delivery system 5500 has an internal lead screw 5510, a lead screw nut 5520, a hollow distal grip handle (also referred to herein as "distal grip") 5530, and a hollow interior body 5540 (also referred to herein as "handle body"). The internal lead screw (also referred to herein as "internal lead screw assembly") 5510 rides within a track 5542 of the hollow interior body 5540. The lead screw nut 5520 has a non-illustrated interior thread having a pitch corresponding to upper thread portions (also referred to herein as "threaded portion") 5512 to cause longitudinal movement of the internal lead screw 5510 when rotated about the hollow interior body 5540. Thus, the lead screw nut 5520 is rotatably freely mounted about the hollow interior body 5540. The lead screw nut 5520 is also longitudinally freely mounted about the hollow interior body (also referred to herein as "handle body") 5540. In this configuration, the clinician has the ability to rotate the lead screw nut 5520 to any desired retraction of the internal lead screw 5510. At any time before, during, or after such rotation, the clinician can move the lead screw nut 5520 longitudinally proximal, taking the internal lead screw 5510 along with it at the same speed of proximal movement of the lead screw nut 5520. The internal lead screw 5510 is longitudinally fixed to the outer sheath 5550, which is longitudinally free from the hollow distal grip handle 5530 and the hollow interior body 5540. In this manner, rotation of the lead screw nut 5520 moves the outer sheath 5550 relatively slowly (dependent upon the pitch of the threads of threaded portion 5512), and longitudinal movement of the lead screw nut 5520 moves the outer sheath 5550 relatively fast.

The difference between FIGS. 55A and 56 illustrates the relative positions of the internal lead screw 5510, the hollow distal grip handle 5530, the hollow interior body 5540, and the outer sheath 5550 after the lead screw nut 5520 has been moved proximally to (about) its proximal-most position. In FIG. 55A, the outer sheath 5550 surrounds the push rod 5560 and completely covers the cavity within the outer sheath 5550 in which the non-illustrated stent graft is stored (compressed) prior to implantation. The outer sheath 5550 extends all the way to touch the nose cone 5570 and form a seal therewith to reliably secure the stent graft therein. In FIG. 56, in comparison, the outer sheath 5550 can be seen completely retracted from the nose cone 5570 to clear the indented boss 7000 at the distal end of the push rod 5560. The apex capture assembly 5568 for removably securing the bare stent (e.g., 2310) of the stent graft is shown just proximal of the nose cone 5570 and in the closed (secured) position of the apex capture assembly 5568. Actuation of the apex release device 5580 moves the inner lumen 5590 connected to the proximal apex capture portion 5572 (with its bare-stent-capturing tines) proximally to create a space through which the individual proximal apices of the bare stent can escape.

It is noted that the entire device disposed in the interior of the hollow distal grip handle 5530 shown in FIG. 55A is not shown in FIG. 56. This device, slider 5700, is shown, in enlarged detail, in FIG. 57A. From distal to proximal, the outer sheath 5550 is secured by a sheath clip 5702 to a distal nipple of a slider cap 5710. The slider cap 5710 has a check or flush valve (also referred to herein as "flush valve orifice") 5712 fluidically connecting the inner chamber of the slider cap 5710 to the environment outside the flush valve orifice 5712. An intermediate slider assembly (also referred to herein as "slider body") 5720 is secured to the slide cap 5710 with an o-ring 5730 therebetween to keep the respective interior chamber fluidically connected to one another and fluidically sealed from the environment outside the two parts slider cap 5710, and slider body assembly 5720.

A release 5514 (e.g., a thumbscrew) removably secures the slider 5700 inside the hollow distal grip handle 5530 and hollow interior body 5540 when the release is placed inside a blind hole 5722 of the slider body assembly 5720. With the release 5514 removed/actuated, all of the parts illustrated in FIG. 56 can be removed from the slider 5700 except for the outer sheath (also referred to herein "sheath") 5550—this includes the entire distal section with the support member 5740, the apex release device 5580 and the nose cone 5570.

As the above delivery systems, a support member 5740 runs entirely through the slider body assembly 5720 and all the way back to the apex release device 5580. This support member 5740 needs to be sealed to the slider 5700 so that blood flow outside the member is not allowed. To effect this seal, a wiper gasket seal (also referred to herein as "wiper valve") 5750 is provided inside the cavity of the slider body assembly 5720. The seal is enhanced with the use of an x-valve 5760.

Figure 128:
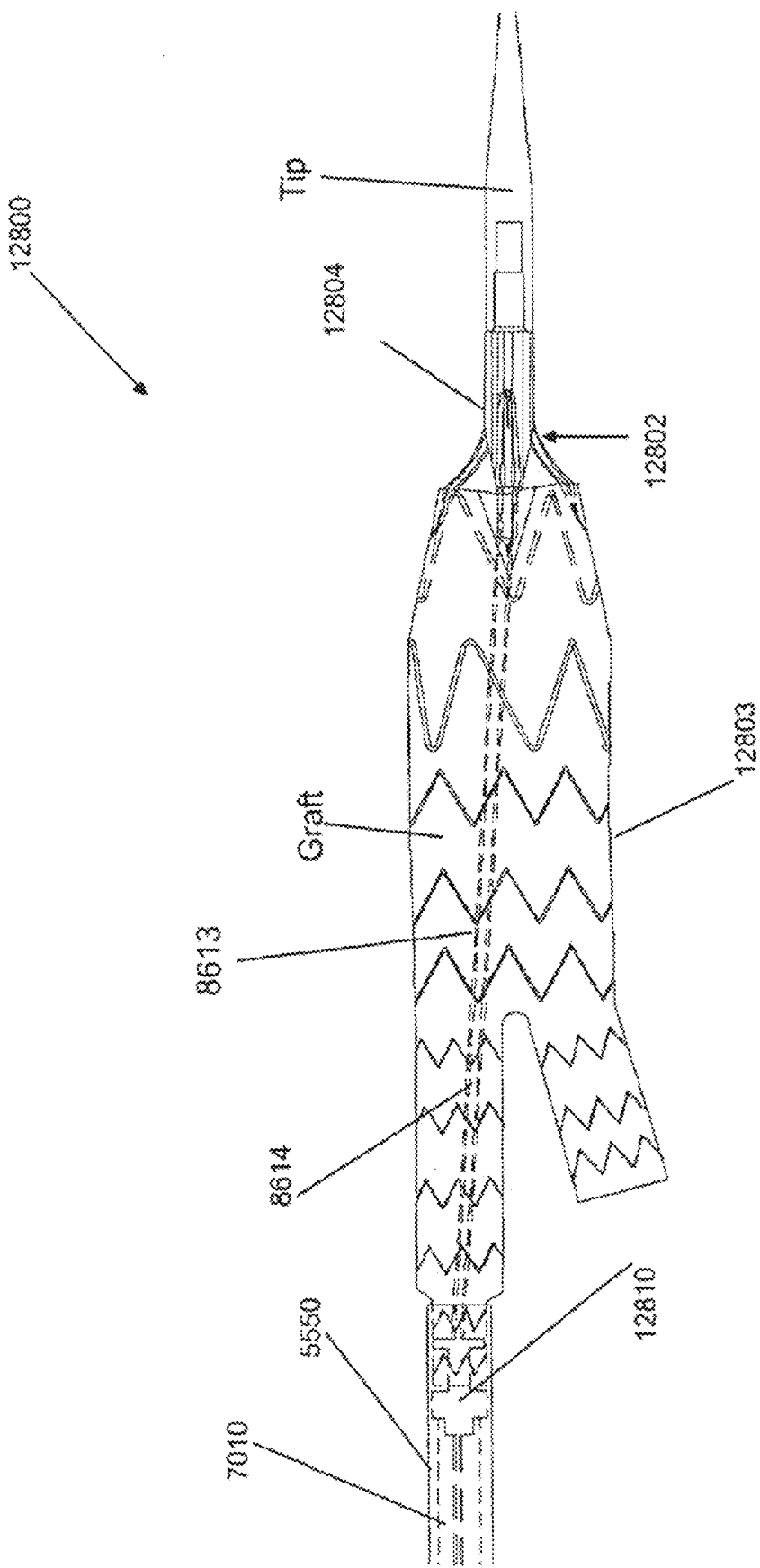

The apex capture device assembly of the invention can be employed in conjunction with the leg clasp of the invention, as shown in FIG. 128. The lumen 8613 and elongate member 8614 extends from apex capture delivery device assembly 12802 through leg clasp 12810. Bifurcated stent graft 12803 extends from apex capture device 12804 to leg clasp 12810, and is secured at each of apex capture device 12804 and at leg clasp 12810 as described above, and for release according to the method of the invention, as also described above.

In an embodiment, the invention is a stent graft delivery device, comprising, an apex capture device assembly, including (1) a proximal apex capture portion, including a nose, wherein the nose defines at least one radial restraint that is substantially parallel to a major axis of the proximal capture portion; and a plurality of tines extending distally from the nose, the tines radially distributed about the major axis radial to a most proximal radial restraint and substantially parallel to the major axis, (2) a distal apex capture portion defining slots distributed radially about the major axis, the slots mateable with the times by relative movement of the proximal and distal apex capture portions along the major axis, (3) a plurality of bosses extending radially from the major axis between the nose and the distal apex capture portion and aligned with the slots along the major axis in non-interfering relation with movement of the tines into mating relation with the slots, (4) an elongate member 8614, otherwise known as an inner control tube, to which the distal apex capture portion is fixed, the elongate member extending through the proximal apex capture portion and the plurality of bosses, (5) a lumen 8613, otherwise referred to as an outer control tube, to which the proximal apex capture portion is fixed, through which the elongate member extends, whereby movement of the lumen causes movement of the proximal apex portion along the major axis between a first position, in which the tines are mated with the slots and overlie the bosses, and a second position, in which the tines are not mated with the slots and do not overlie the bosses, (6) a bare stent that includes struts linked by apices, the struts extending between the tines, a portion of the apices extending between the bosses and the distal apex capture portion when the tines are mated to the slots and (7) at least one suprarenal barb extending from the stent into the radial restraint; and a leg clasp through which the elongate member and lumen extend, the leg clasp including, (1) a barrel, (2) a spool extending from the barrel along a major axis of the barrel, and (3) a rim at an end of the spool, the rim having a diameter greater than that of the spool but less than that of the barrel.

In another embodiment, the invention is an x-valve assembly, comprising an x-valve; and a gasket supporting the x-valve. The gasket includes a peripherial support and at least one arm extending inwardly from the peripherial support. In an embodiment, the gasket includes at least two pairs of arms, along intersecting major axes. In an embodiment, each pair of arms is aligned. At least two of the axes of the x-valve assembly can be normal to each other. The pairs of arms in the x-valve assembly can lie in a plane. The gasket of the x-valve assembly can include a superelastic metal, which can include nitinol.

Figure 57B:
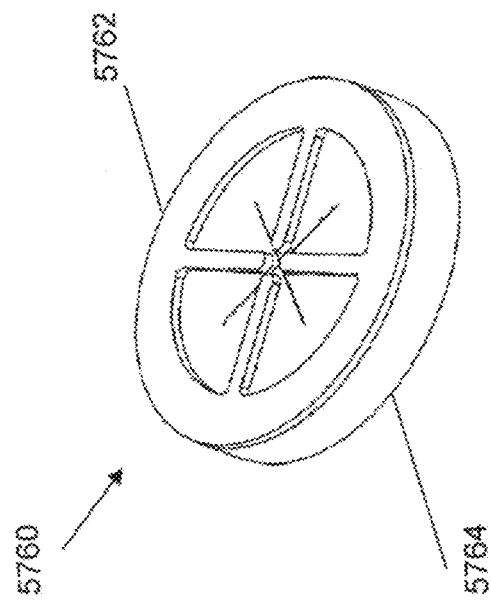
Figure 57E:
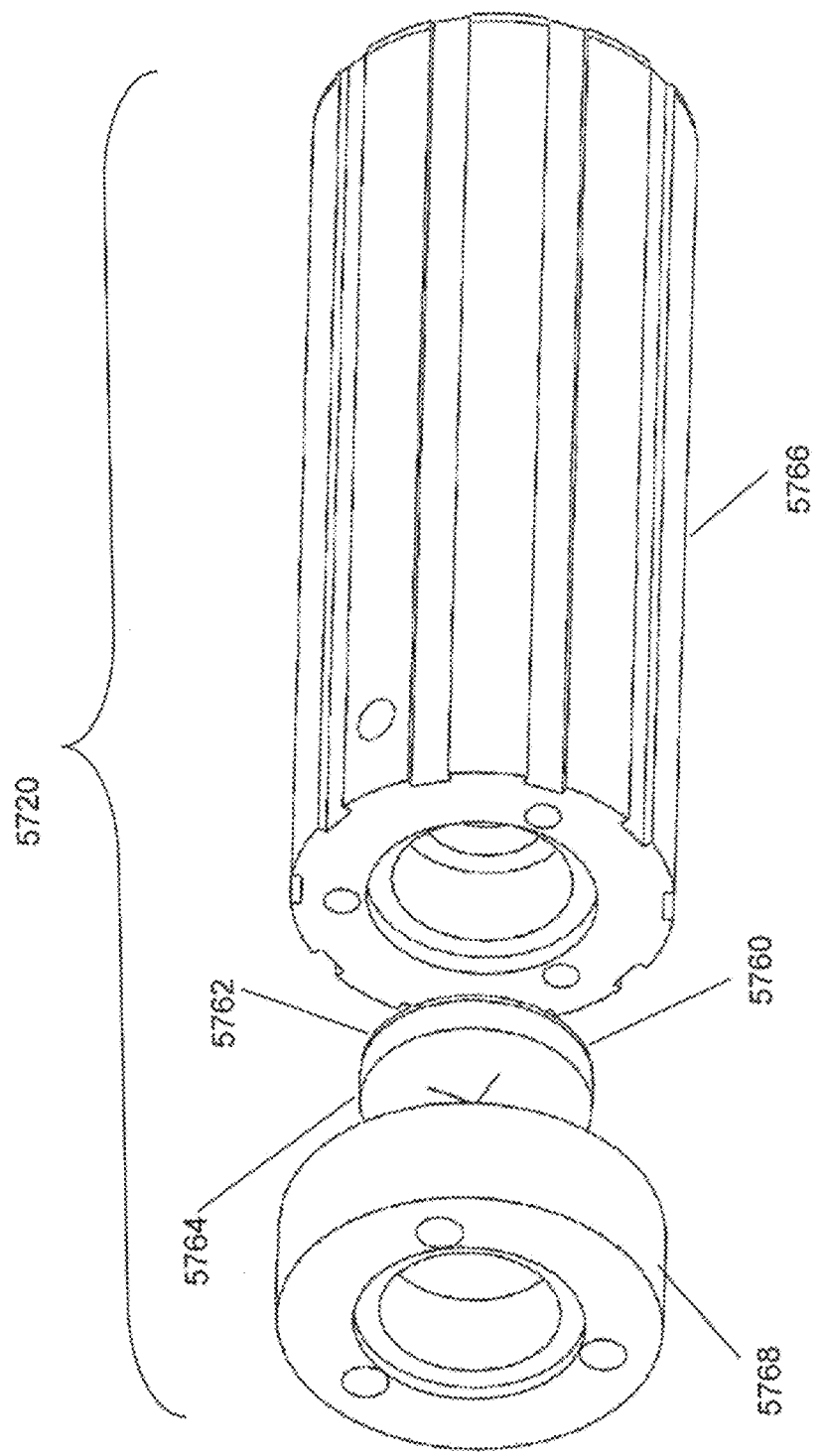
Figure 57F:
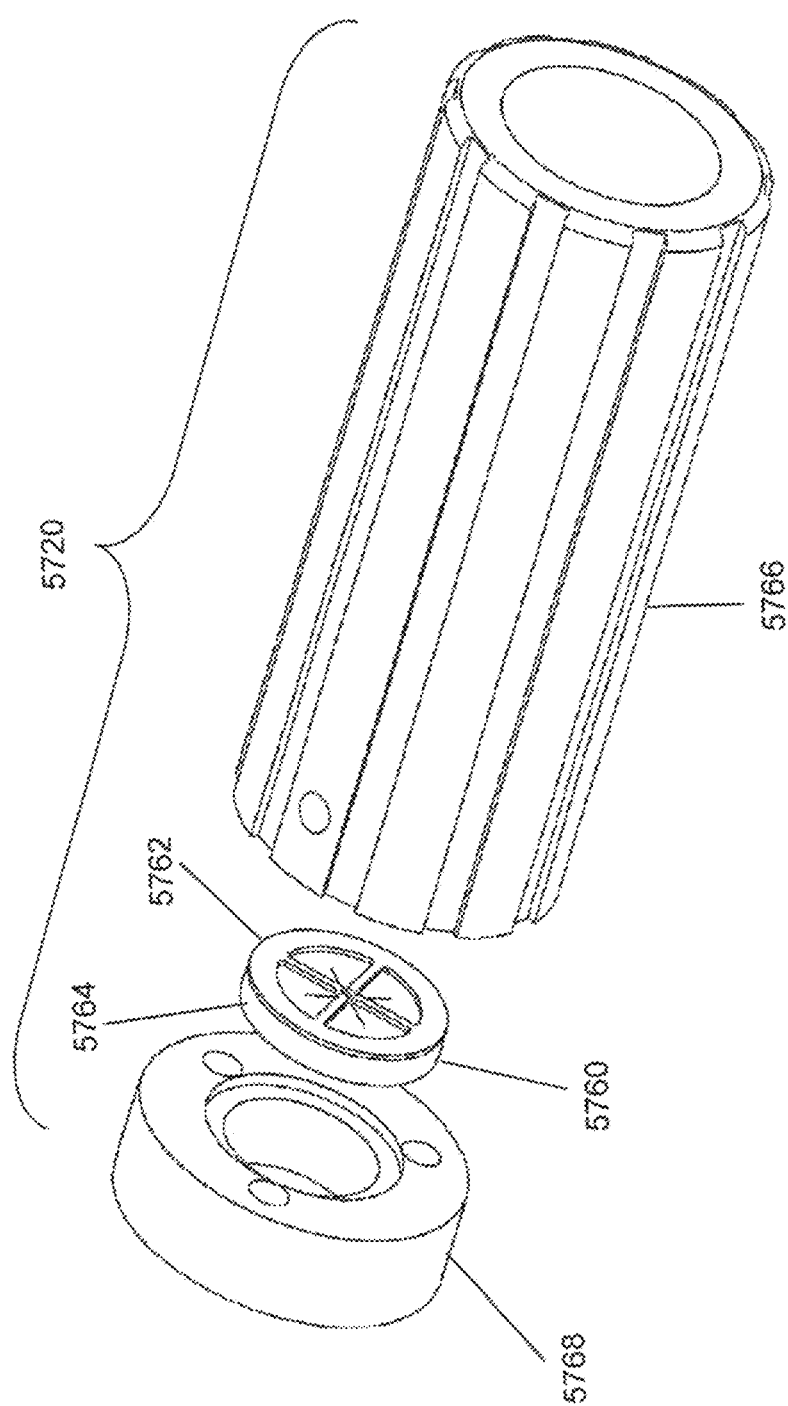

X-valve assembly 5760 can be seen in greater detail in FIG. 57B. As shown therein, x-valve assembly 5760 includes gasket support 5762 and valve 5764. Gasket support 5762 is shown separately in FIG. 57C. Gasket support 5762 typically includes superelastic metal, such as nickel titanium (i.e., nitinol). X-valve 5764 is shown separately in FIG. 57D. Valve 5764 typically is formed of silicone. A partially exploded view of x-valve assembly 5760 slider assembly 5720 is shown in FIG. 57E. Another perspective of a partially exploded view of x-valve assembly 5760 in slider assembly 5720 is shown in FIG. 57F. Slider assembly 5720 components shown in FIGS. 57E and 57F include slider body 5766 and gasket spacer 5768. The slider body and gasket spacer typically formed of polyetheretherketone (PEEK). With this configuration, when the support member 5740 is in the slider 5700 as shown in FIG. 57A, blood flow outside the slider 5700 is substantially prevented when the proximal end of the support member 5740 is sealed). The flush valve orifice 5712, therefore, is the only way for blood flow to occur, but only if the blood surrounds the support member 5740.

As set forth above, the support member 5740 can be removed from within the slider 5700. While the wiper valve seal 5750 and the x-valve 5760 form some or even a substantial measure of sealing capability, the blood-tight seal needs to be ensured. Accordingly, a sealing assembly is provided at the proximal end of the slider 5700, which sealing assembly is comprised, in one exemplary embodiment, of a sheath valve 5770, a sheath valve washer 5780, and a sheath valve knob 5790. As described in the following text, the sheath valve washer 5780 is not necessary but is included in this embodiment. The sheath valve 5770 here is formed as a cylindrical piece of silicone but can take any shape or material so long as, when compressed inside the slide assembly 5720, it creates a blood-tight seal inside the blind hole 5722 of the slide assembly 5720. With the configuration shown in FIG. 57A, the sheath valve knob 5790 is connected into the proximal end of the slide assembly (also referred to herein as "slider body") 5720 with a thread so that, when rotated with respect to the slide assembly 5720, the knob 5790 enters into or removes therefrom. Thus, after removal of the interior assemblage, (as the nose cone is being withdrawn from the slide assembly 5720, with appropriate rotation, the knob 5790 pushes the sheath valve washer 5780 inwards against the sheath valve 5770 to compress the sheath valve 5770 on itself and seal up the hole left after the support member 5740 and all of the interior assemblage is removed. In a particular embodiment of the sheath valve 5770, an annular groove 5772 on the outside diameter of an intermediate portion of the sheath valve improves a self-sealing collapse of the sheath valve 5770. Easier collapse is desired because of the strain that the user experiences when having to rotate the knob 5790 with greater resistance. The groove 5772 significantly reduces the force required and the number of knob turns required.

Figure 58:
FIG. 58 is an embodiment of a distal tip of the delivery system of the invention.
Figure 59:
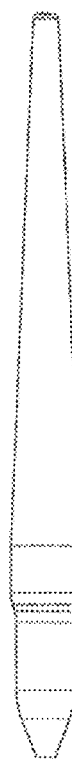
FIG. 59 is an embodiment of a distal tip of the delivery system of the invention.
Figure 60:
FIG. 60 is an embodiment of a distal tip of the delivery system of the invention.
Figure 61:
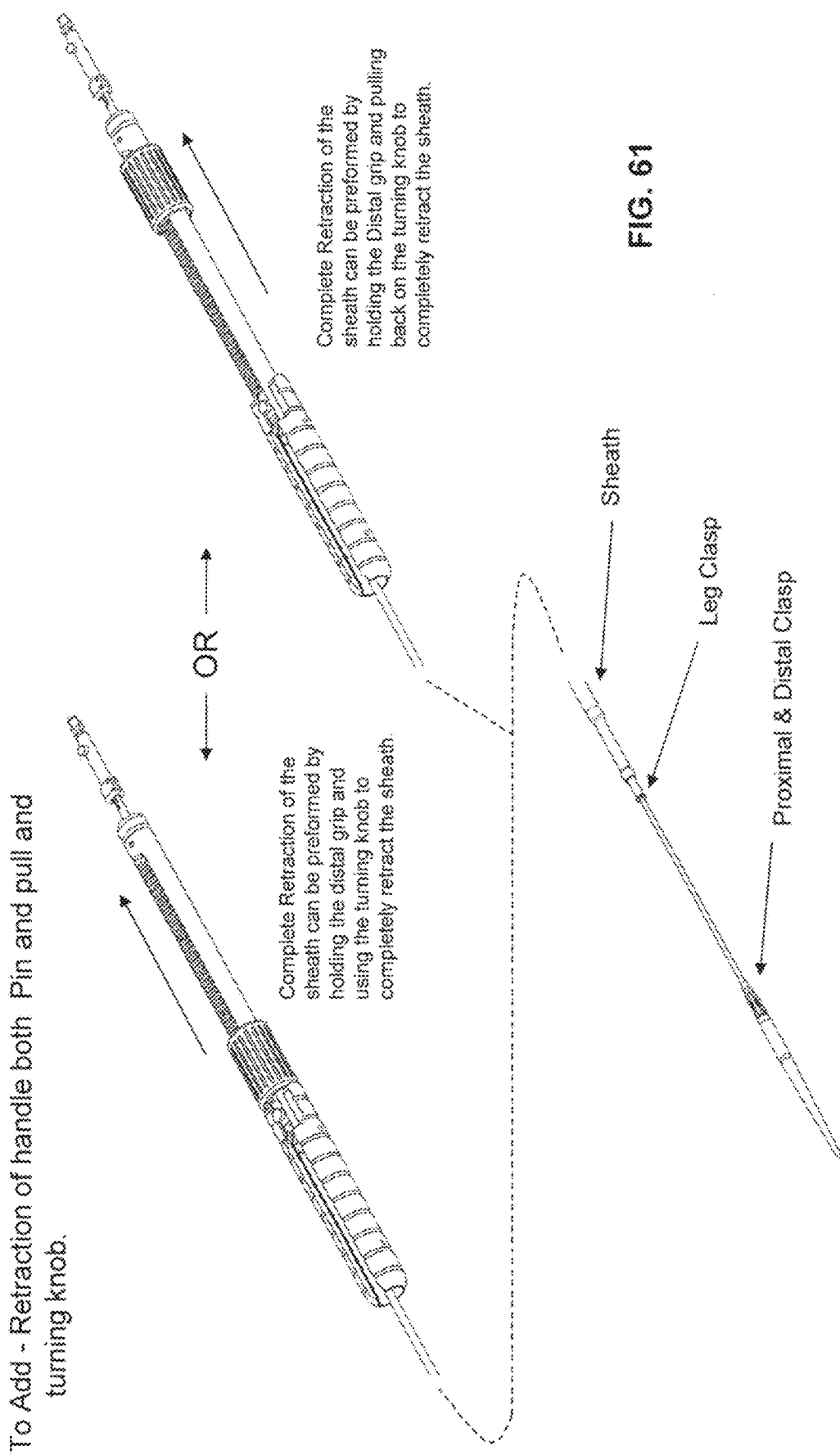
FIG. 61 is an embodiment of a delivery system of the invention.

FIGS. 58 to 60 illustrate exemplary embodiments of the nose cone of the delivery systems of the present invention.

A passive hemostasis valve for the delivery systems 100, 700, 1600, 2400, 3300, 5500 can replace the sheath valve 5770 in the system 5700 of FIG. 57. Hemostasis can be maintained by two components. First, a seal on the guidewire can be made by a "duckbill" type valve. The duckbill can have mechanical assist, for example, such as by two spring-loaded rollers, to ensure the seal. The seal on the sheath of the second device is maintained by a rubber disc having a hole slightly smaller than the sheath it will receive. This component also maintains hemostasis for the main system.

FIGS. 65 to 69 illustrate an exemplary embodiment of a leg-extension delivery system according to the invention (as compared to the main or bifurcated delivery system as shown, for example, in FIGS. 55A to 57. The measurements shown in these figures are not to be taken as the only embodiment and, instead, should be taken as only exemplary for the invention.

The above-described delivery systems 100, 700, 1600, 2400, 3300, 5500 each require the stent graft to be loaded within the outer sheath lumen and each have an interior device that both prevents the stent graft from being inserted too far into the sheath lumen and keeps the stent graft longitudinally fixed when the outer sheath is being retracted over the stent graft. When implanting a bifurcated stent graft, it is desirable to ensure that the last two springs (e.g., stents) of the ipsilateral leg are not prematurely released from the outer sheath during deployment. The invention, shown in FIGS. 70A, 70B and 70C, allows the capture of the stent graft's ipsilateral leg while the contralateral leg is cannulated. Such a configuration ensures stability of the stent graft during the cannulation of the contralateral leg.

An additional embodiment of the invention shown in FIGS. 70A, 70B and 70C, as an example, is a leg clasp 7001, comprising a barrel 7002; a spool 7004 extending from the barrel 7002 along a major axis of the barrel 7002; and a rim 7006 at an end of the spool 7004, the rim 7006 having a diameter greater than that of the spool 7004 but less than that of the barrel 7002, as shown in FIGS. 70A, 70B and 70C.

Figure 125:
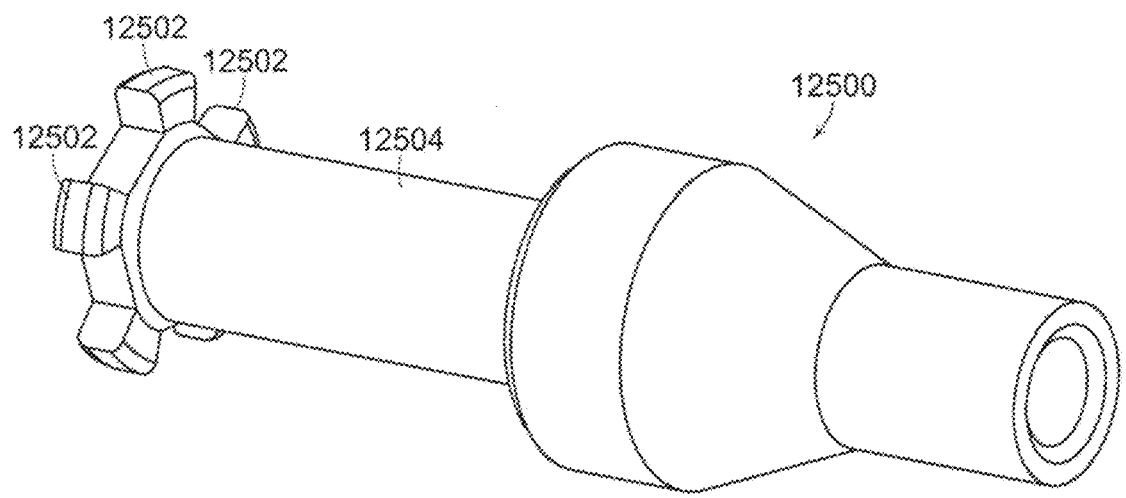
Figure 126:
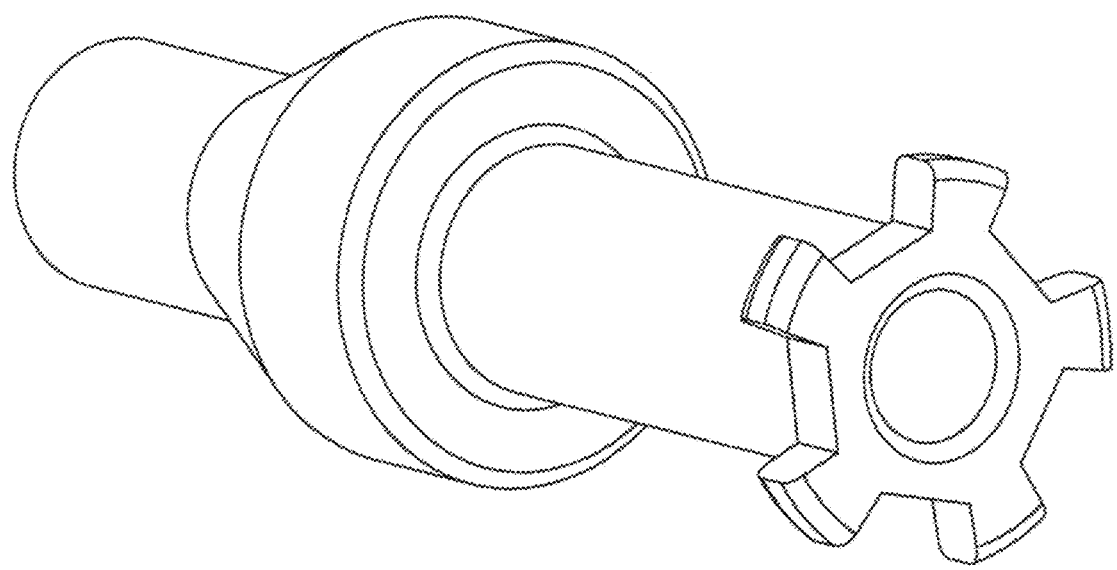
Figures 127C, 127D:
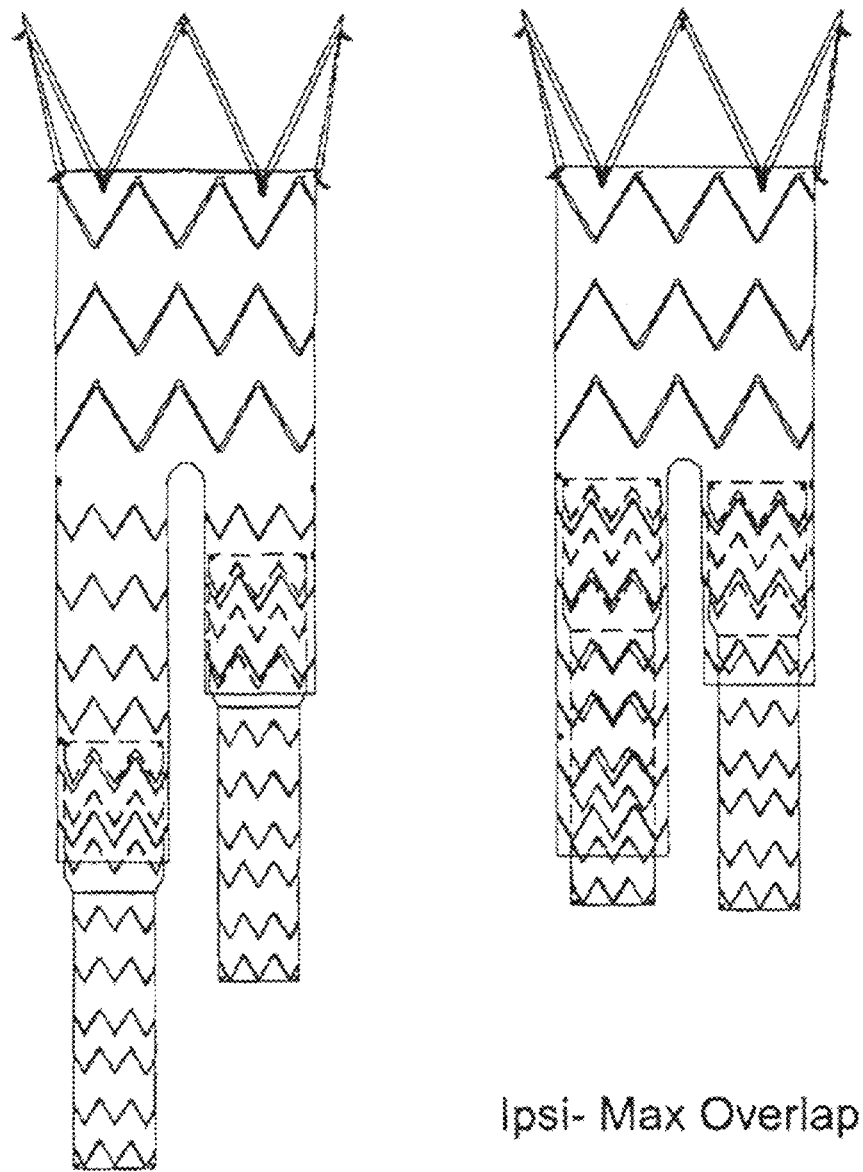

The leg clasp 7001 of the invention can formed, at least in part, of at least one component selected from the group consisting of stainless steel, polyester, polyetheretherketone (PEEK) and acrylonitrile butadiene styrene (ABS). The rim 7006 of the leg clasp 7001 of the invention can include radially extending spokes 12502, as shown in FIGS. 125 and 126.

In still another embodiment, the invention is a stent graft delivery system, comprising a leg clasp 7001 that includes a barrel 7002, a spool 7004 extending from the barrel 7002 along a major axis of the barrel 7002 and a rim 7006 at an end of the spool 7004, the rim 7006 having a diameter greater than that of the spool 7004 but less than that of the barrel 7002; a support tube 7010 fixed to the barrel 7002 and extending from the barrel 7002 in a direction opposite that of the spool 7004; and a sheath 7030 (FIGS. 70A and 70C) having an internal diameter relative to that of the barrel to permit movement between a first position that covers the spool 7004 and rim 7006 and a second position that exposes the spool 7004 and rim 7006. It is to be understood that support tube 7010 is also represented as support tube 5744 in FIG. 57B, and that, in an alternative embodiment, some other component of support member 5740, shown in FIG. 57B, can be fixed to barrel 7002, such as hypo-tube 5742, also shown in FIG. 57A, and that support tube 7010 can be fixed directly to hollow interior body 5540, shown in FIG. 56.

The stent graft delivery system of the invention can further include a stent graft 7020, wherein a stent 7024 of the stent graft extends about the spool 7004 in interfering relation with the rim 7006 when the outer sheath 7030 is in the first position, and a luminal graft 7032 to which the stent is fixed extends between the rim and the sheath, whereby movement of the sheath from the first to the second position releases the stent graft from the leg clasp.

In particular, an indented boss 7000 is placed at the distal end of the push rod (also referred to herein as "support member") 7010, which prevents the stent graft 7020 from being inserted too far into the outer sheath 7030 and keeps the stent graft 7020 longitudinally fixed when the outer sheath 7030 is being retracted over the stent graft 020. The indented boss 7000 has a proximal flange (also referred to herein as a "barrel") 7002, an intermediate span (also referred to herein as a "spool") 7004, and a distal flange (also referred to herein as a "rim") 7006. The outer diameters of the proximal and distal flanges 7002, 7006 are larger than the outer diameter of the intermediate span 7004 to create an annular cavity 7008 therebetween. If the stent graft leg 7022 is placed over the distal flange 7006 sufficiently far to have the distal-most stent 7024 within the annular cavity 7008, the indented boss 7000 creates an interference fit between the leg 7022 and the outer sheath 7030. Once the outer sheath 7030 is completely retracted, the interference fit disappears. It can be said that the fixation of the last stent 7024 is passive due to the fact that, after the outer sheath 7030 is retracted, the fixation is lost. This configuration can be used to better control and grasp the stent graft 7020 by preventing longitudinal movement thereof when the outer sheath 7030 is retracted (to the left of FIG. 70A).

The following sections discuss improvements to stent grafts, in particular, bifurcated AAA stent grafts intended to span the renal arteries. As shown in FIGS. 72A, 72B, 72C through FIG. 83, a stent graft system, such as bifurcated stent graft system 7200, comprising a luminal graft component 7201; a bare stent component 7210 including a plurality of struts 7211 joined by proximal 7212 and distal 7213 apices connecting the struts 7211, the bare stent component 7210 fixed to a proximal end 7214 of the luminal graft component 7201 and extending proximally from the proximal end 7214; an infrarenal stent component 7215 proximate to the bare stent component 7210, wherein the infrarenal stent component 7215 is distal to the bare stent component 7210 and spans a circumferential line defined by apices 7213 of the bare stent component 7210 fixed to the luminal graft component 7201; at least one suprarenal barb 7220 extending distally from at least one suprarenal portion 7217 of the bare stent component 7210; and at least one infrarenal barb 7230 extending distally from at least one infrarenal portion 7218 of the bare stent 7210.

"Suprarenal," as used herein in reference to a barb, means a barb that attaches to the aorta cranial to the ostium of the most superior renal artery.

"Infrarenal," as used herein in reference to a barb, means a barb that attaches to the aorta caudal to the ostium of the most inferior renal artery.

In another embodiment, an infrarenal barb can be a first covered barb. Bare stent is also referred to as "uncovered" or "partially" covered stent.

"Barb" is also referred to herein as "hook."

Figure 73:
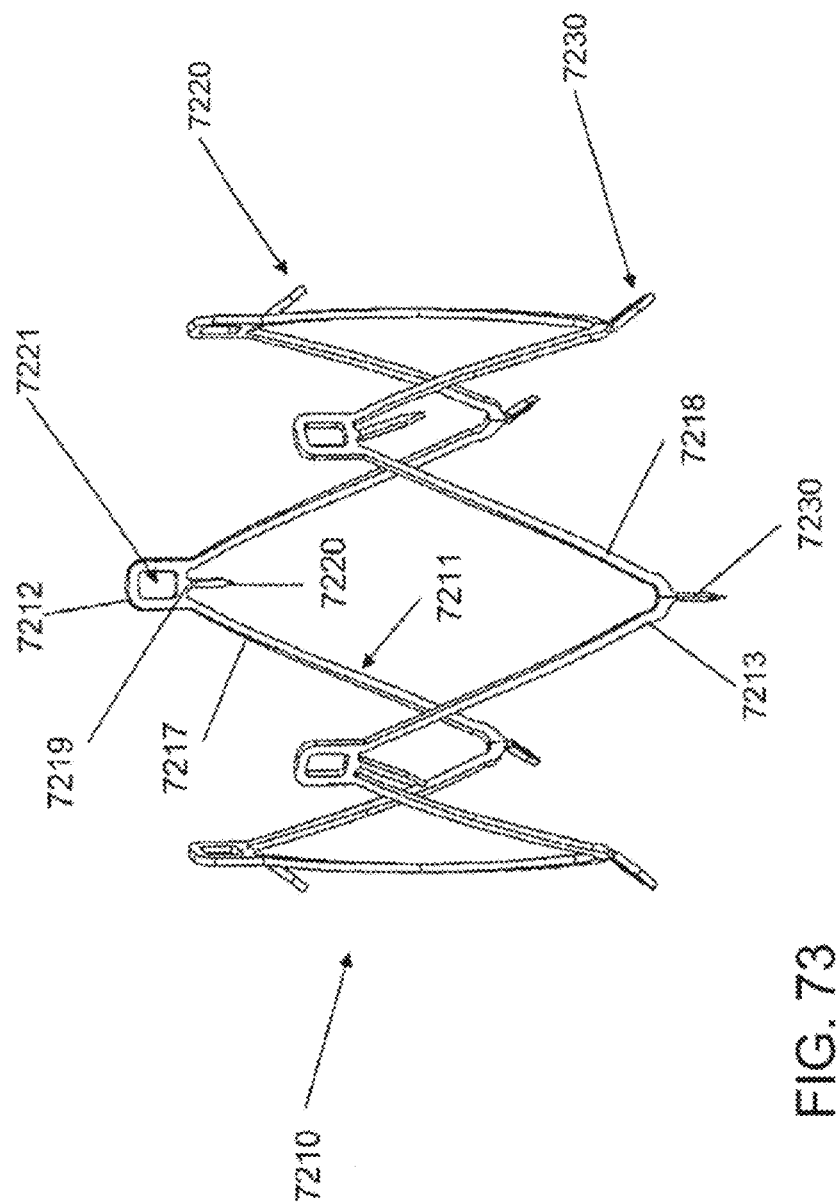
FIG. 73 is an embodiment of a stent of the invention.

As shown in FIG. 73, in the stent graft system of the invention, the suprarenal portion of the bare stent 7210 can include a bridge 7219 between struts 7211 to define an eyelet 7221 that joins two struts 7211, and wherein the suprarenal barb 7220 extends from the bridge 7219.

The infrarenal barb 7230 of the stent graft system of the invention can extend from a distal apex 7213 that joins two struts 7211.

Exemplary distances between the most proximal point of the suprarenal and infrarenal barbs of the stent graft system of the invention is in a range of between about 6 mm and about 40 mm (e.g., 6 mm, 10 mm, 15 mm, 20 mm, 25 mm, 30 mm, 35 mm, 40 mm).

At least one of the stents of the stent graft system of the invention can include a superelastic metal, such as nickel titanium.

In an embodiment, the distal apices of a bare stent of the stent graft system of the invention are fixed within the luminal graft component and wherein the infrarenal barb extends from the bare stent through the lumen. At least one infrarenal stent of the invention can be fixed within the luminal graft component.

Figure 105C:
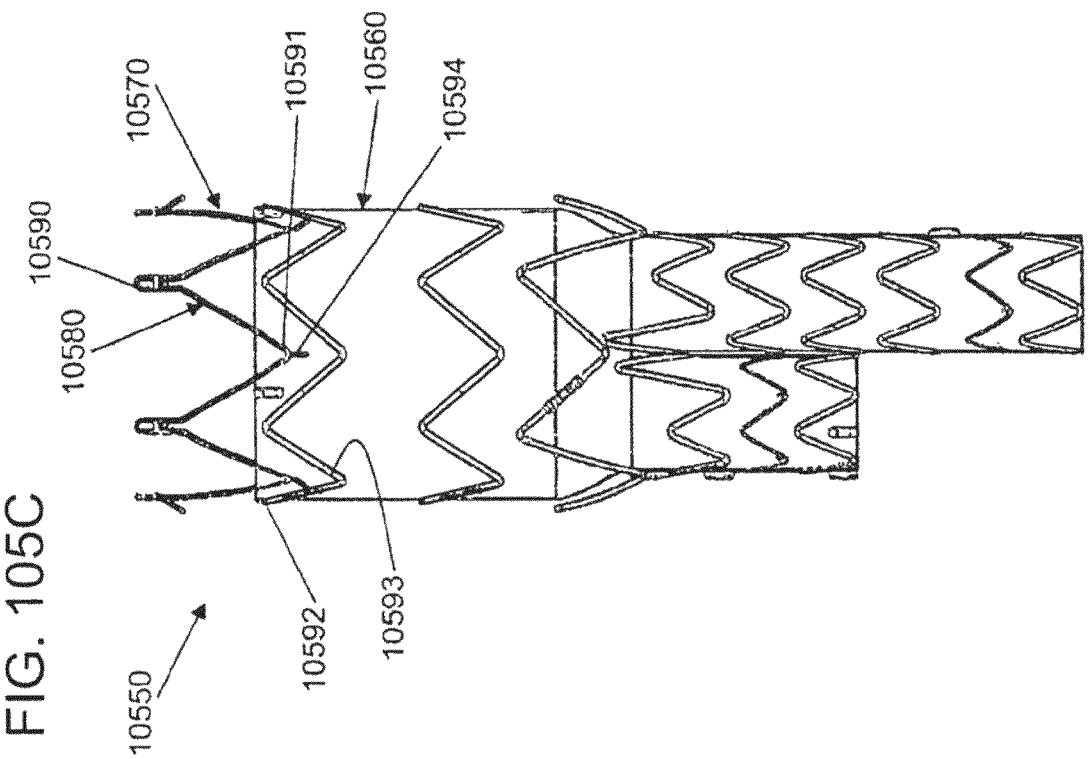
FIGS. 105A, 105B and 105C are embodiments of a stent of the invention.

Another embodiment of the invention, shown in FIG. 105C is a stent graft system 10550, comprising a luminal graft component 10560; a bare stent 10570 of angled struts 10580 joined by proximal 10590 and distal 10591 apices, and extending from a proximal end 10592 of the luminal graft component 10560; a proximal stent 10593 adjacent the bare stent 10570 and within the luminal graft 10560, the proximal stent 10593 including angled struts 10580 joined by proximal apices 10590 and optionally distal apex 10591 nested with the bare stent 10570; and at least one barb 10594 extending distally from a distal apex 10591 and through the luminal graft component 10560.

Figure 71:
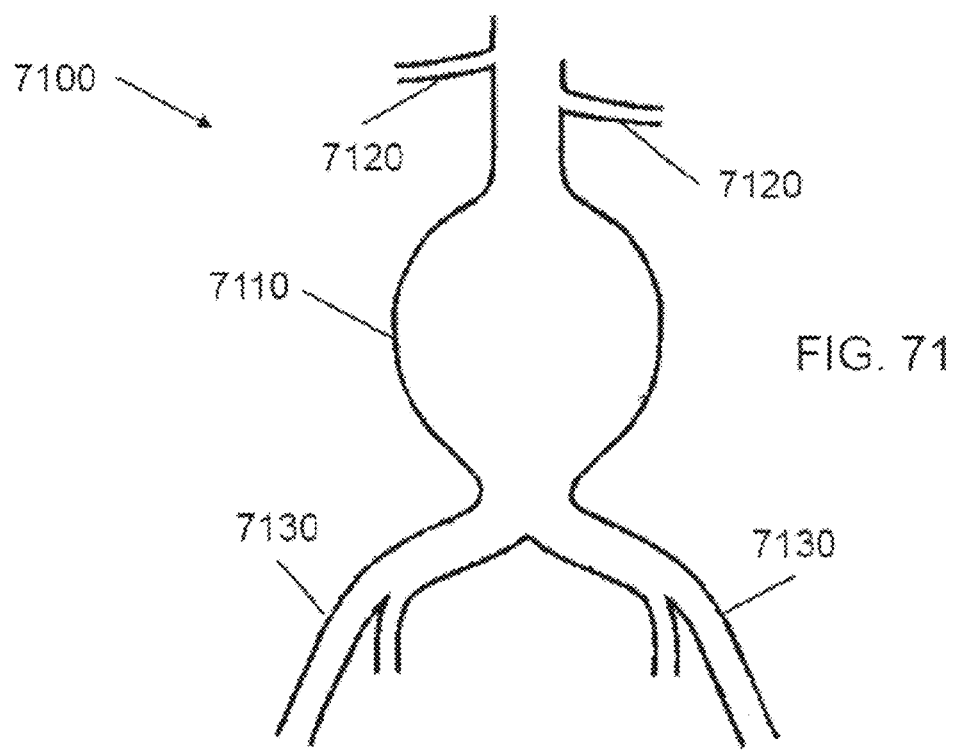
FIG. 71 is a representation of an abdominal aortic aneurysm.

FIG. 71 diagrammatically illustrates an abdominal aorta 7100 with an aneurysm 7110 between the renal arteries 7120 and the iliac arteries 7130—the abdominal aorta 7100 branches, at its downstream end, and becomes the left and right common iliac arteries 7130, carrying blood to the pelvis and legs. FIGS. 72A, 72B and 72C diagrammatically illustrates a stent graft system, such as a bifurcated stent graft system 7200 having a graft portion that extends from just downstream of the renal arteries 7120 towards the iliac arteries 7130, splitting into two smaller lumens, one of which extends into an iliac artery 7130 and the other ending before the other iliac artery 7130. The bare stent 7210 of this bifurcated stent graft 7200 is configured with both suprarenal barbs 7220 and infrarenal 7230 barbs.

Another embodiment, shown in FIG. 72B the invention is a stent graft system 7200, comprising a luminal graft component 7201; a bare stent 7210 extending from a proximal end 7214 of the luminal graft component 7201, such as a bifurcated luminal graft component; at least one proximal barb 7220 extending distally from a proximal end 7217 of the bare stent 7210; and at least one distal barb 7230 extending distally from an infrarenal portion 7218 of the bare stent 7210, the distance, a, between the proximal 7220 and distal 7230 barbs along a major axis of the luminal graft component being in a range of between about 6 mm and about 40 mm (e.g., 6 mm, 10 mm, 15 mm, 20 mm, 25 mm, 30 mm, 35 mm, 40 mm).

In the stent graft system of the invention, at least a portion of the barbs extend from the bare stent at an angle in a range of between about 20 degrees and about 60 degrees (e.g., 20 degrees, 25 degrees, 30 degrees, 35 degrees, 40 degrees, 45 degrees, 50 degrees, 55 degrees, 60 degrees).

A bare stent of the stent graft system of the invention can be formed, at least in part, of a superelastic metal.

As shown in FIGS. 78 and 79, the stent graft systems of the invention can further include at least one radiopaque marker 7800. At least one radiopaque marker attached to the stent graft systems of the invention, either to the stent or the graft material, can aid in the place of the stent graft in a patient by employing stent graft delivery systems of the invention, for example, in methods of treating abdominal aortic aneurysms.

Figure 75:
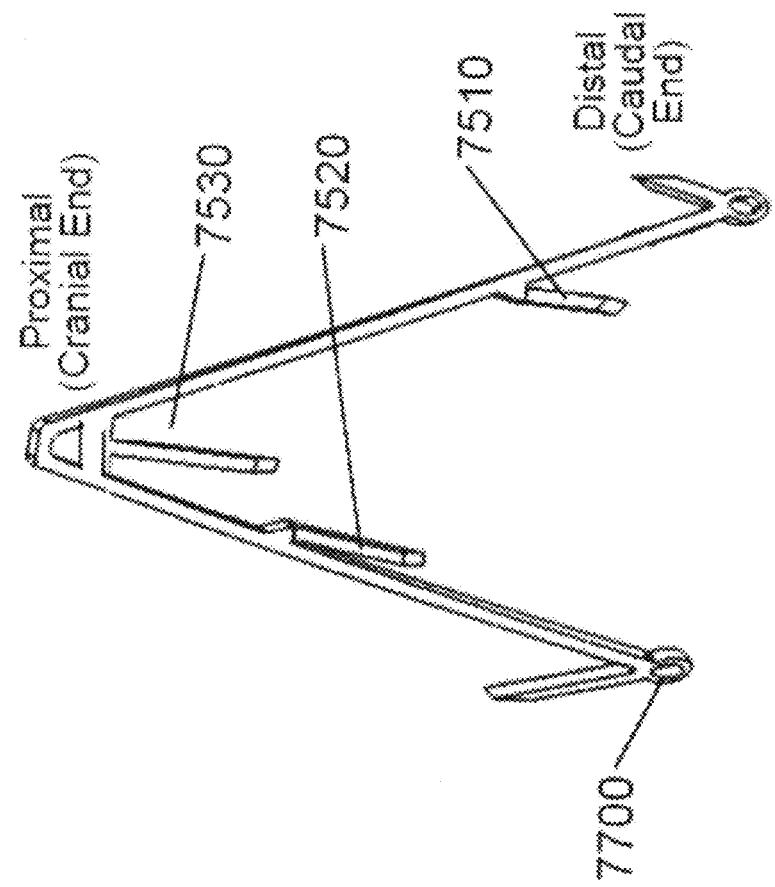
FIG. 75 is an embodiment of a stent of the invention.
Figure 74:
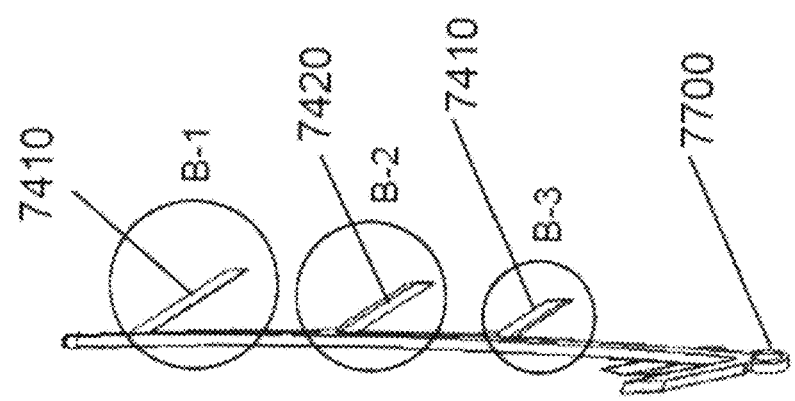
FIG. 74 is an embodiment of a stent of the invention.

FIGS. 73 to 75 illustrate various features of a suprarenal bare stent 7210 with hooks or barbs 7212 according to an exemplary embodiment of the invention an AAA stent-graft system. A 6-apex version is shown, although more or less apices could be used. This bare stent 7220, 7230 has, as shown in FIG. 74, different length hooks 7410, 7420, 7430 that, for example, increase in length based upon the distance from the graft edge (of course, these lengths can decrease in this direction or be a combination of lengths). In an embodiment, the hooks 7410, 7420, 7430 increase in length the further away from the graft edge (i.e., B-1 is longer than B-2 and is longer than B-3) because, in an angled neck, hooks further from the graft line are more likely to be further from the aortic wall. Further, shorter hooks nearer to the renal arteries is safer for patients.

FIG. 75 shows an orientation where hooks 7510, 7520, 7530 increase in length further away from the graft edge and are disposed at staggered positions along various circumferential planes at distances from the graft edge.

FIGS. 73 through 75 and 77 illustrate an eyelet 7700 at each apex at the graft end (distal) of the bare stent. This feature assists in suturing the stent to the graft material. Benefits of the eyelet include suturing in an area of the stent with no stresses or strain during normal post-sewing process steps. Typically, stents are sewn around the intrados of the sinusoid of the stent. This area will be subjected to elastic deformation during post sewing process steps like crimping/loading and final deployment. Such movements can only have detrimental effects on the sutures. Additionally, during normal anatomical movements in the body, the intrados of the stent will have the most movement. An eyelet, as shown in these figures, will not be subject to any movement or plastic deformation that would beyond the general movement of the whole prosthesis. Suturing in the area of a stent that will not be subject to any stresses or strain is advantageous from a manufacturing perspective. During the sewing process, the needles can cause small gauges in the stent, which could become focal points for crack initiation and subsequent fracture. These gauges would be of much greater concern in the intrados than in a static area such as the eyelet 7700. Should the suprarenal stent of the invention be subjected to a fracture after implant, the intrados area of the stent is likely to be a spot where the fracture would occur. If the suture is done in this spot, a fracture could result in the complete disassociation of the suprarenal stent from the graft. By sewing on this added eyelet feature, a fractured stent would still have one of the two struts attached to the graft after that fracture. Thus, once a fracture occurred, it would be far less likely for the second strut in the same area to also break away from the shared intrados. Having the inferior eyelets shown as the suture securement areas of the stent has significant advantages:

Stents of the invention can be of a size from about 20 mm to about 36 mm, and include, for example, 20 mm, 22 mm, 24 mm, 26 mm, 28 mm, 30 mm, 33 mm, and 36 mm.

The stent can be cut from a 3 mm OD tube, for example. The width of the can be equivalent (but not need be equivalent) to the circumference of a 3 mm tube. The tubing wall can be, for example, 0.017". FIGS. 81 to 85 illustrate one exemplary embodiment of a laser-cut supra-renal stent with side hooks according to the invention with exemplary measurements for the stent when being manufactured from such a tube. This exemplary embodiment includes 6 superior and 6 inferior apices, although variants could have more or less. Strut thickness can be targeted to mimic a wire of approximately 0.016" to 0.018" diameter. But can be of varying diameters, for example, the wall thickness can be 0.017".

Barbs can be bent out of plane and sharpened as part of a finishing process. All of the barbs, or only a subset of the barbs, may be included in the stent of the invention.

Figure 69:
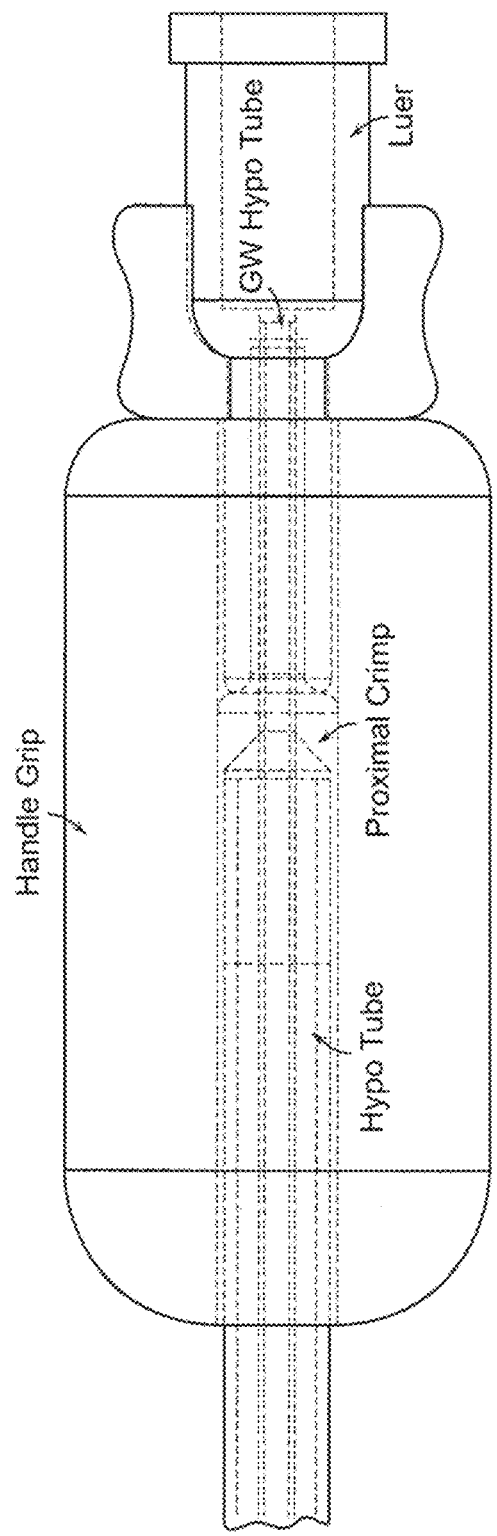
FIG. 69 is an additional embodiment of the delivery system of the invention.

The bare stents described above are to be used with the delivery systems according to the invention, which systems include distal apex capture devices, an example of which is shown in FIG. 69. With the addition of the barbs, however, the spaces that previously existed between each of the stent arms 8010 (i.e., the lengths between the apices) is now taken up by the barbs. This can be seen, in particular, in FIGS. 80 and 84. Accordingly, the apex capture device previously used is modified to take account of the lost of "space" between the arms 8010.

Figure 88A:
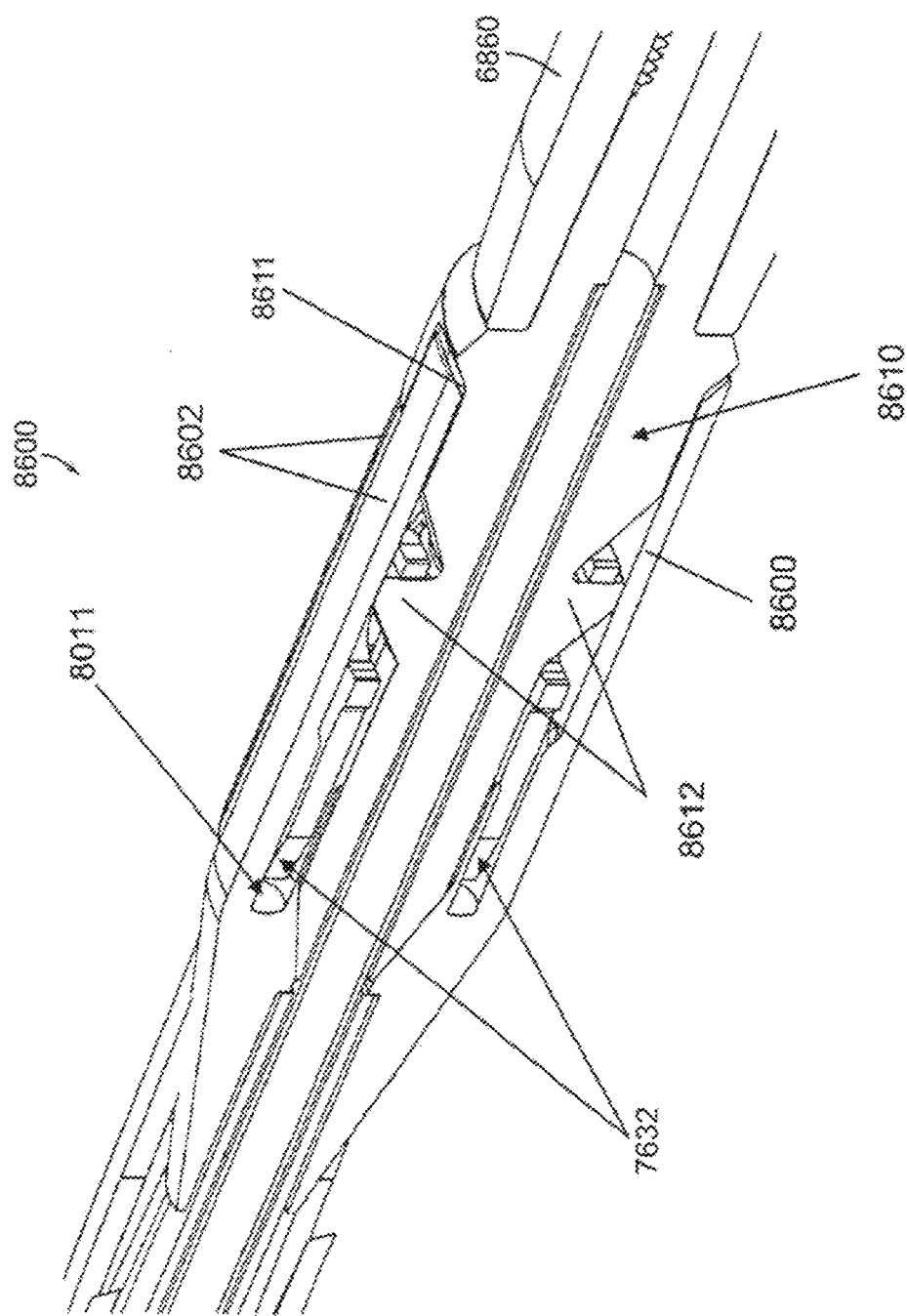
FIGS. 88A and 88B are embodiments of the apex capture device of the invention.
Figure 88B:
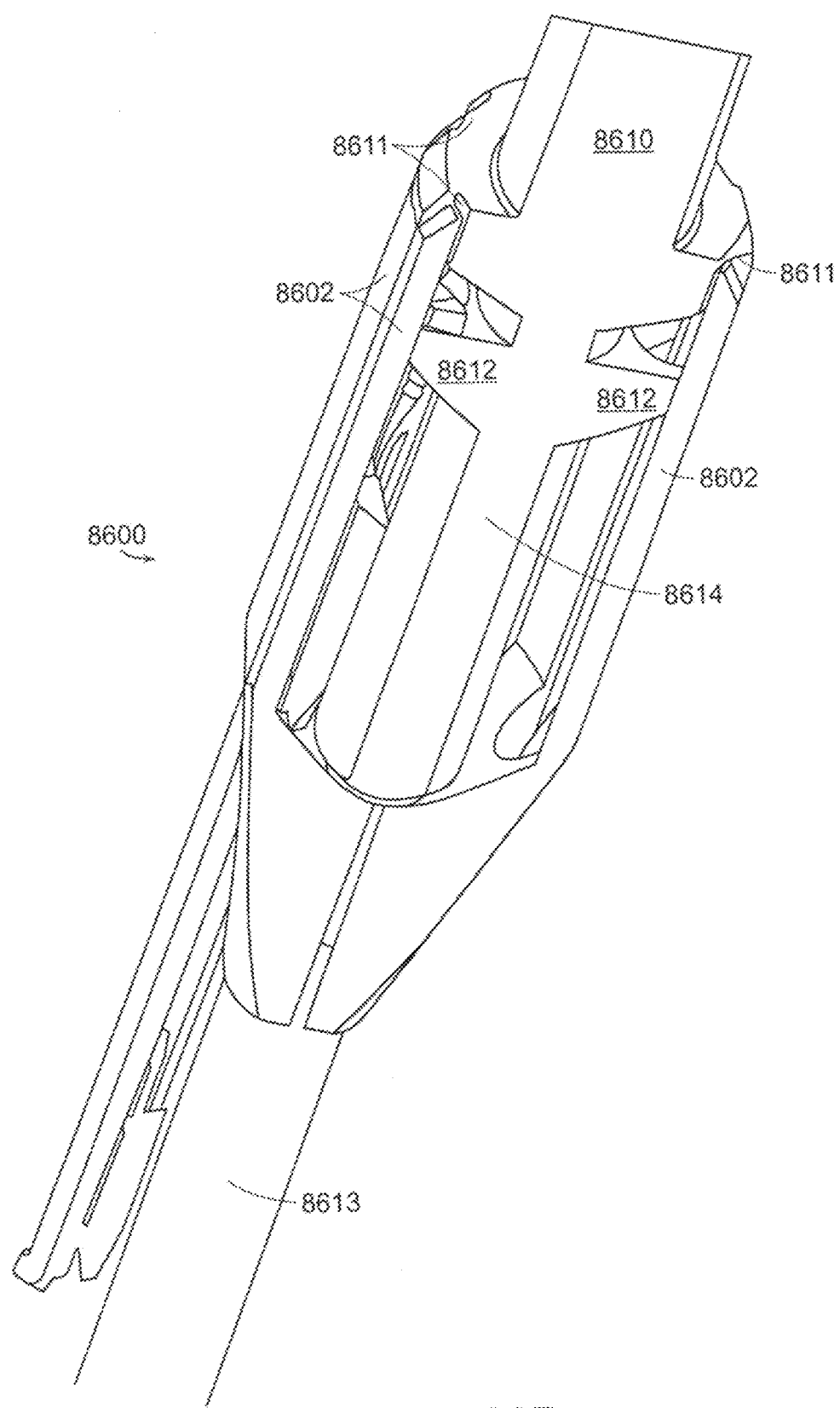

In an embodiment, the invention is an apex capture device 8600, comprising a proximal apex capture portion 8600a that includes a nose 8601, wherein the nose defines at least one radial restraint, such as a pilot holes, represented as 8011, in FIGS. 86C and 88, that is substantially parallel to a major axis of the proximal capture portion 8600a and a plurality of tines 8602 extending distally from the nose 8601, the tines 8602 are radially distributed about the major axis radial to a most proximal radial restraint and are substantially parallel to the major axis; a distal apex capture portion 8610 defining slots 8611 distributed radially about the major axis, the slots 8611 mateable with the tines 8602 by relative movement of the proximal 8600a and distal 8610 apex capture portions along the major axis; a plurality of bosses 8612 extending radially from the major axis between the nose 8601 and the distal apex capture portion 8610 and aligned with the slots 8611 along the major axis in non-interfering relation with movement of the tines 8602 into mating relation with the slots 8611; an elongate member 8614, shown in FIG. 86D, (also known as an inner control tube) to which the distal apex capture portion 8610 is fixed, the elongate member 8614 extending through the plurality of bosses 8612 and the proximal apex capture portion 8600a; and a lumen 8613, also shown in FIG. 86D, (also referred to as an outer control tube) to which the proximal apex capture portion 8600a is fixed, through which the elongate member extends, whereby movement of the lumen 8613 causes movement of the proximal apex capture portion 8600a along the major axis between a first position, in which the tines 8602 are mated with the slots 8611 and overlie the bosses 8612, and a second position, in which the tines 8602 are not mated with the slots and do not overlie the bosses 8612.

"Radial restraint," as used herein, means restricted movement in a direction normal to the major axis of the delivery system or the apex capture device, whereby, for example, a barb of a stent could be released between tines of the apex capture device.

"Non-interfering relation," as used herein, means one object is moveable relative to another object.

The nose 8601 of the apex capture device of the invention can define grooves 8603 between the tines 8602, wherein the grooves 8603 are aligned with spaces between the bosses 8612.

In an embodiment, the plurality of bosses 8612 of the apex capture device of the invention are fixed relative to distal apex capture portion 8610.

The nose, elongate member and each of the tines 8602 of the apex capture device of the invention can define a space.

In another embodiment, the invention is a method of releasing a bare stent of a stent graft, comprising the steps of moving a lumen, to which a proximal apex capture portion of an apex capture device is fixed, the proximal apex capture portion defines a radial restraint, along a major axis between a first position, in which tines of the proximal apex capture portion are mated with slots of a distal apex capture portion and overlie bosses extending radially from a major axis of the apex capture device, and a second position, in which the tines are not mated with the slots and do not overlie the bosses, thereby releasing apices of a bare stent from a space defined by the tines, the bosses and the distal apex capture portion.

In an embodiment, the apex capture device employed in the method of releasing a bare stent of a stent graft can further include an elongate member to which the distal apex capture portion is fixed, the elongate member extending through the proximal apex capture portion and the plurality of bosses.

In another embodiment, the apex capture device employed in the methods of the invention can further include a lumen to which the proximal apex capture portion is fixed, through which the elongate member extends, and by which the proximal apex capture portion is moved.

Figure 76A:
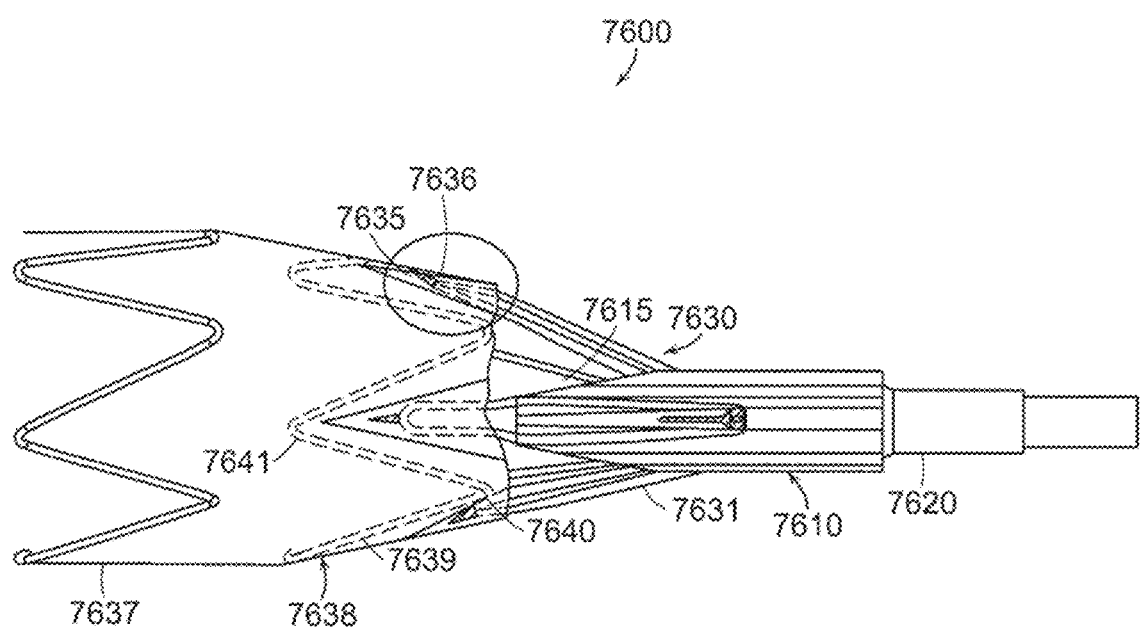
FIGS. 76A and 76B are embodiments of a component of a delivery system of the invention.

In yet another embodiment, the invention is an apex capture device assembly 7600, comprising a proximal apex capture portion 7610 that includes a nose 7615, wherein the nose defines at least one radial restraint, such as a pilot hole, previously described, that is substantially parallel to a major axis of the proximal capture portion and a plurality of tines, previously described extending distally from the nose 7610, as shown, for example, in FIG. 76A, the tines radially distributed about the major axis radial to a most proximal radial restraint and substantially parallel to the major axis; a distal apex capture portion 7620, as shown, for example, in FIG. 76A, defining slots distributed radially about the major axis, the slots mateable with the times by relative movement of the proximal and distal apex capture portions along the major axis; a plurality of bosses extending radially from the major axis between the nose and the distal apex capture portion and aligned with the slots along the major axis in non-interfering relation with movement of the times into mating relation with the slots; a elongate member to which the distal apex capture portion is fixed, the elongate member extending through the proximal apex capture portion 7610 and the plurality of bosses; a lumen to which the proximal apex capture portion 7610 is fixed, through which the elongate member extends, whereby movement of the lumen causes movement of the proximal apex portion along the major axis between a first position, in which the tines are mated with the slots and overlie the bosses, and a second position, in which the tines are not mated with the slots and do not overlie the bosses; a bare stent 7630 that includes struts 7631 linked by apices, the struts extending between the tines 8602 (FIG. 86B), a portion of the apices extending between the bosses and the distal apex capture portion when the tines are mated to the slots; and at least one suprarenal barb 7632 (FIG. 76B) extending from an eyelet of the stent into the radial restraint (not shown).

The stent of the apex capture device assembly of the invention can further include at least one bridge between a pair of the struts to define an eyelet through which a boss extends when a tine is mated to a slot, and wherein the barb extends from the bridge.

Figure 76B:
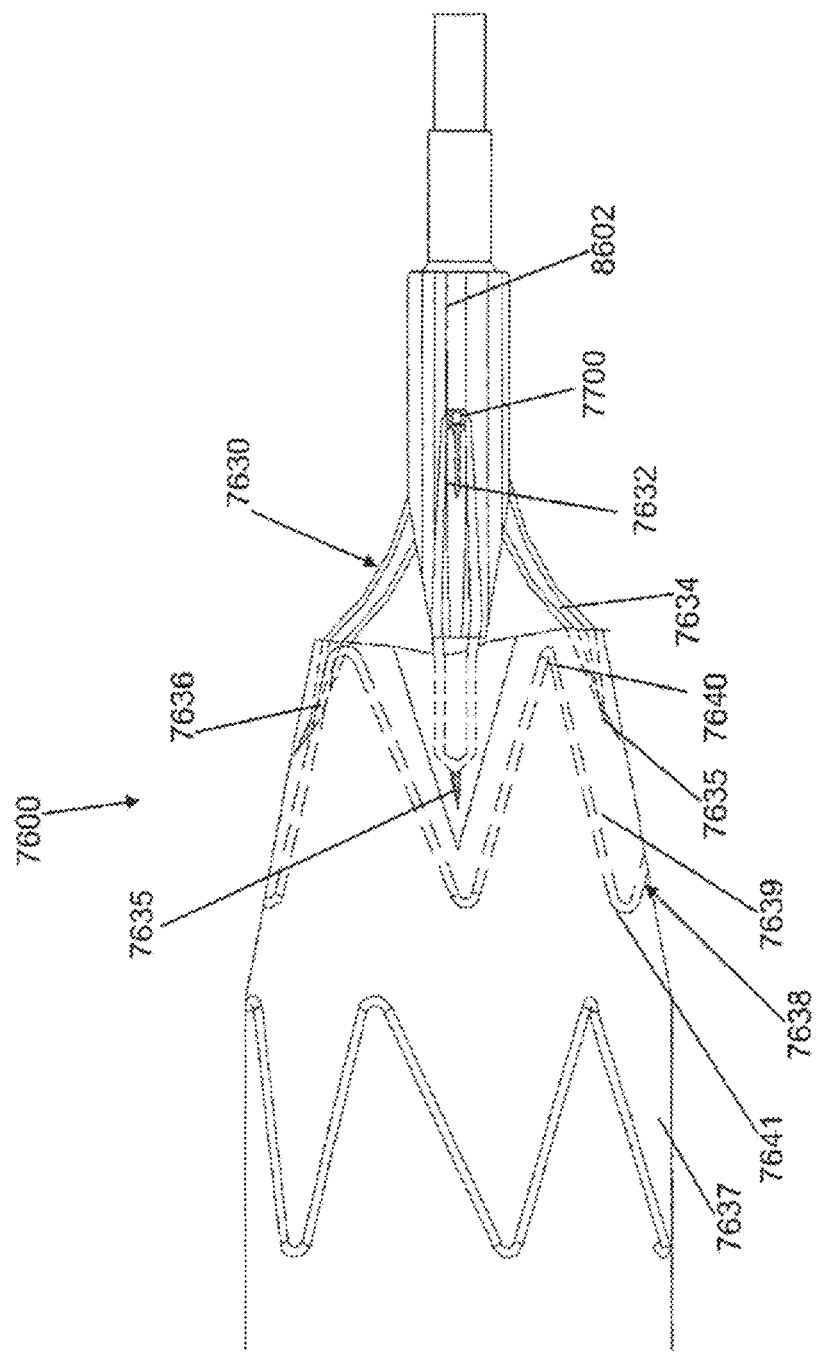
Figure 77:
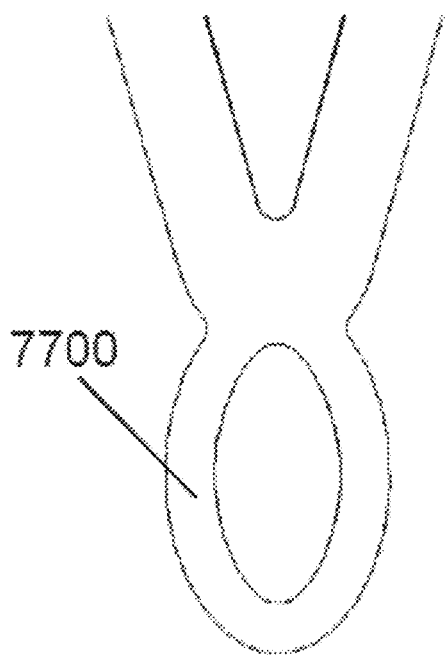
FIG. 77 is an embodiment of an eyelet of a stent of the invention.

In an alternative embodiment, shown in FIG. 76B, the struts 7634 are angled. The struts are angled as a result of clasping the bare stent and restraining the barbs thereby creating a deeper valley for at least one infrarenal barb.

Referring to both FIGS. 76A and 76B, the suprarenal barb of the apex capture device assembly of the invention is angled (not shown) from a major plane of the eyelet sufficient to distend the struts to which the eyelet is attached toward the major axis.

The apex capture device of the invention can further include an infrarenal barb 7635 extending from a distal apex 7636 of the stent 7630.

The apex capture device assembly of the invention can further include a luminal graft component 7637 fixed to a distal portion of the bare stent 7630 and an infrarenal stent 7638 adjacent and distal to the bare stent 7630, the infrarenal stent 7638 including struts 7639 linked by proximal 7640 and distal 7641 apices, the distal apices 7641 being substantially aligned with distal apices 7636 of the bare stent 7630. In an embodiment, the infrarenal stent 7638 of the apex capture device assembly 7600 of the invention is fixed within the luminal graft component 7637. Distention of the bare stent struts 7631, 7634 consequent to retention of the barbs 7632 within the radial restraint, such as a pilot hole 8011 (FIG. 86C), can cause the infrarenal barb 7635 of the bare stent 7630 to be recessed between struts 7639 of the infrarenal stent 7638.

For example, as shown in FIGS. 86A, 86B, 86C, 86D and 86E through 88, the proximal apex capture portion 8600 having the tines 8602 is in the bare stent release position, in which it is separated from the distal apex capture portion 8610 (which is connected to the nose cone 6860 (FIG. 88A)). The upstream apices of the stent 8620 (FIG. 87A), while captured and before springing open upon final deployment, are wrapped around holding bosses 8612 that circumferentially align with a respective one of the tines 8602 and, therefore, extend radially outward to touch the respective tine 8602, or come close enough to prevent any stent apex release when closed over by the tines 8602. To complete the capture cavity for the stent apices, the distal apex capture portion 8610 has recesses 8816 that are shaped to fit snugly the distal-most ends of each one of the tines 8602. Accordingly, the recesses 8611 of distal apex capture portion 8610 are circumferentially offset from the bosses 8612, as represented in FIGS. 86A-86E. Elongate member 8613 extends from proximal capture portion 8600.

Figure 89:
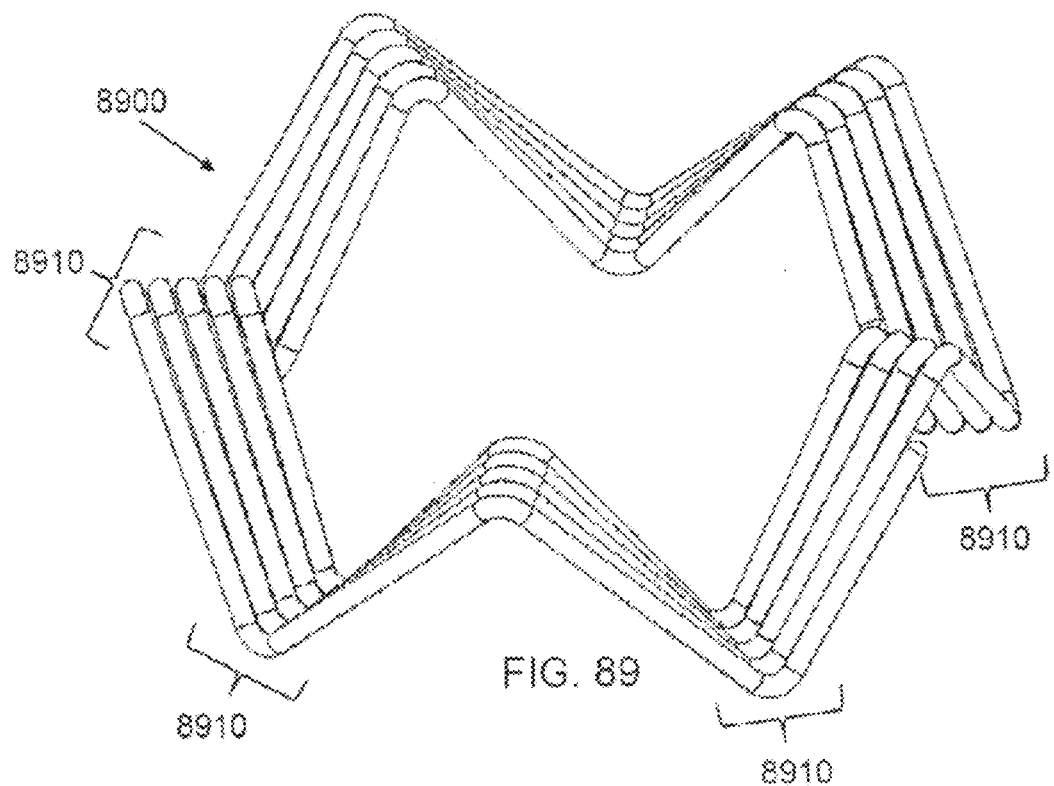
FIG. 89 is an embodiment of multiple stents of the invention.
Figure 90:
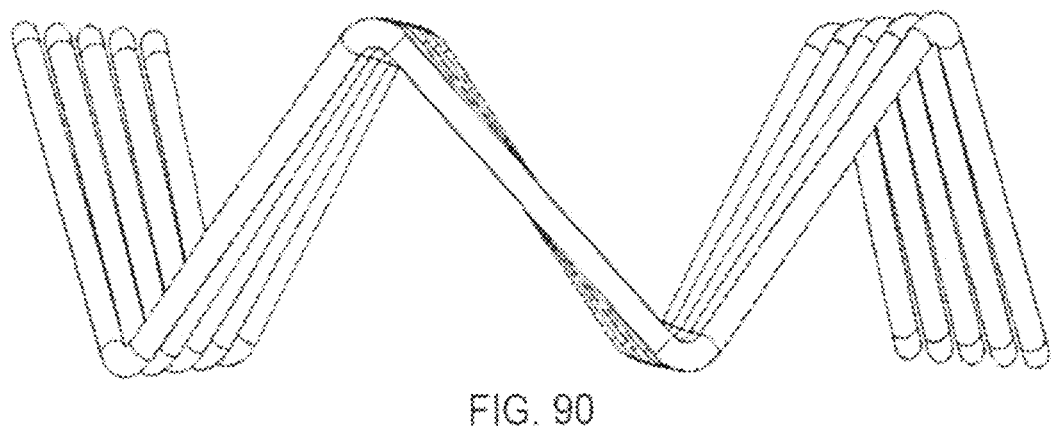
FIG. 90 is an embodiment of multiple stents of the invention.
Figure 91:
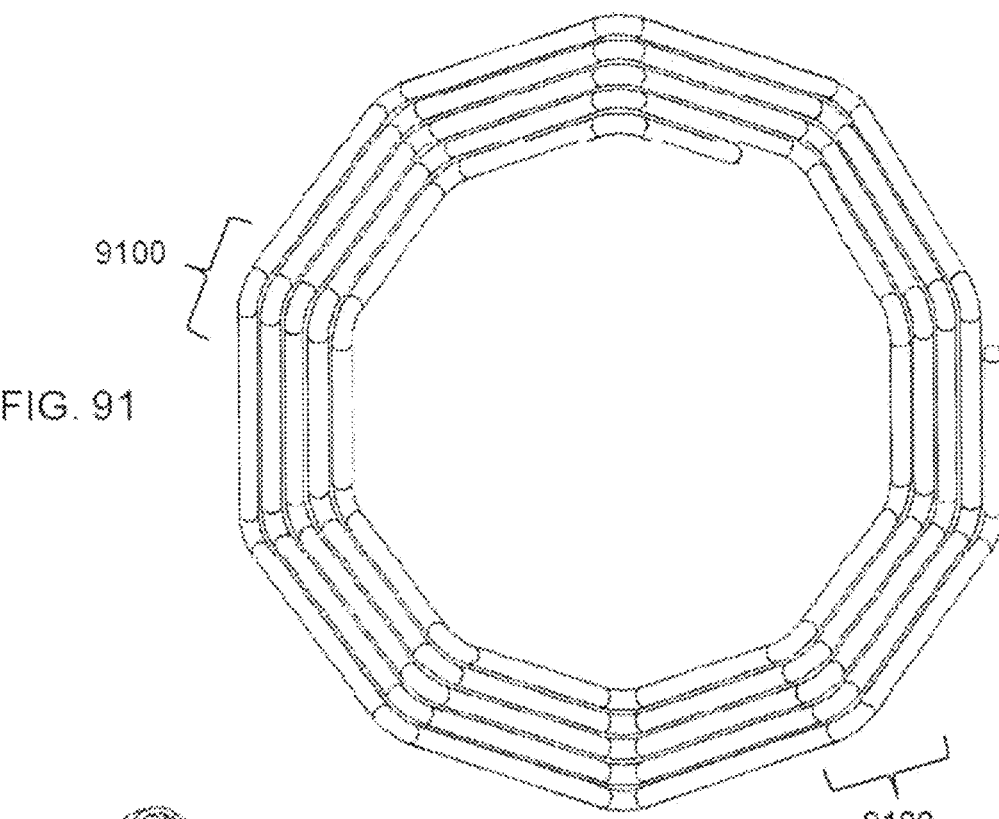
FIG. 91 is an embodiment of multiple stents of the invention.
Figure 92:
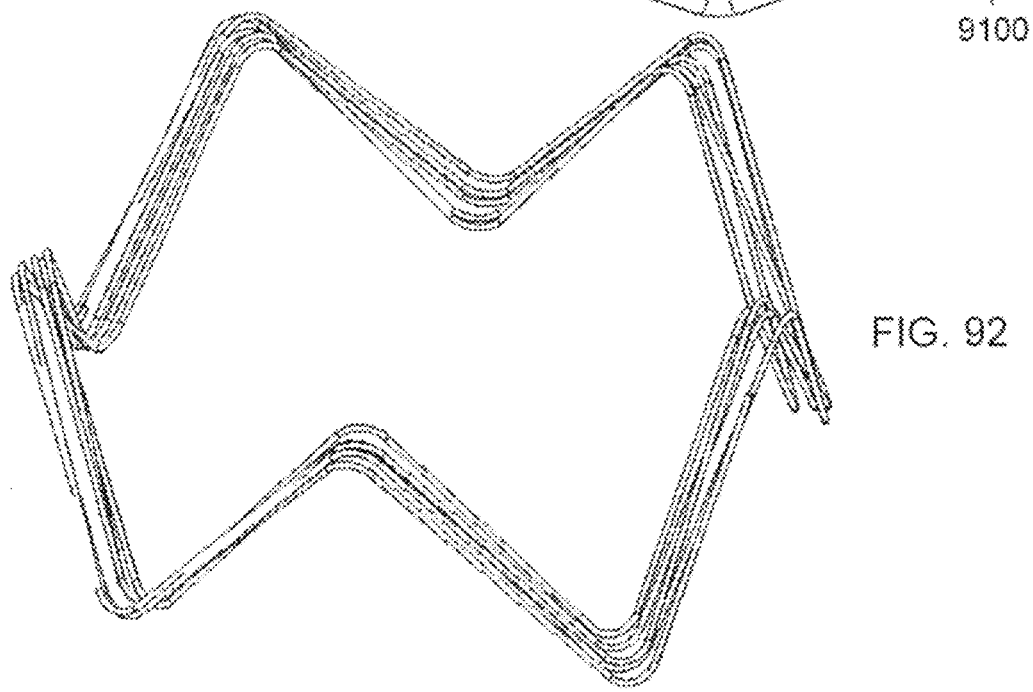
FIG. 92 is an embodiment of multiple stents of the invention.
Figure 93:
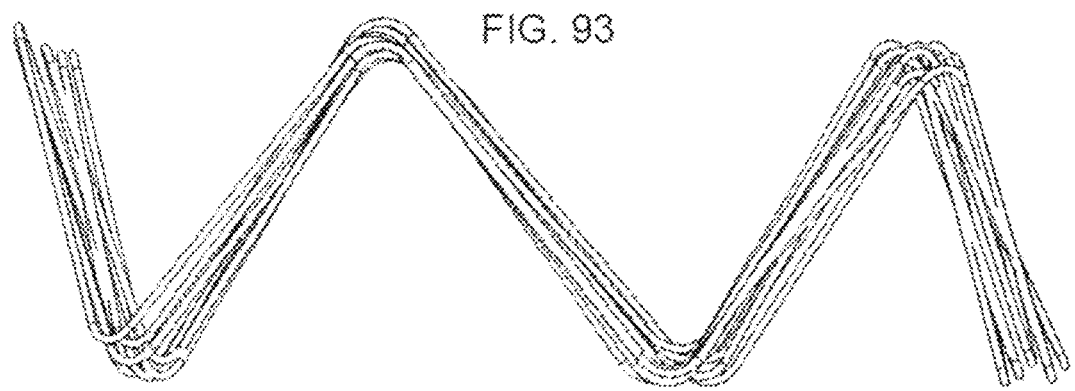
FIG. 93 is an embodiment of multiple stents of the invention.
Figure 94:
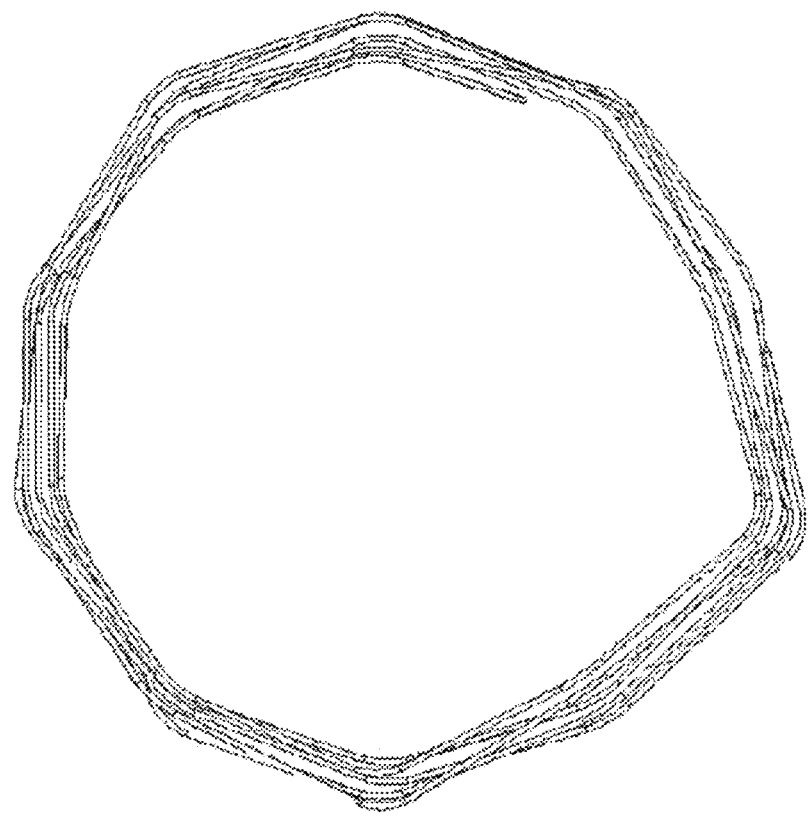
FIG. 94 is an embodiment of multiple stents of the invention.

Prior art Z-stents are made of a single length of wire joined at the two ends. Provided herein, and shown in an exemplary embodiment in FIGS. 89 and 90, is a multiple-stent 8900 made with a plurality of circumferentially adjacent filaments. There are various features that exist with the multiple-stent 8900 that do not arise in prior art stents.

The multiple-stent 8900 is a wire form stent made from wire that is substantially smaller in diameter than used in prior art stents/stent grafts. In spite of this substantial reduction in diameter, the multiple turns around the circumference create a total metal cross-section on each strut of each stent similar to prior art stents. Having multiple turns in the multiple-stent 8900 creates multiple apices 8910 at each bend of the composite stent 8900. These apices can be used to improve implantation on an interior wall of a vessel to be treated. Additionally, each of these apices 8910 can be used to catch onto the graft material of a second modular component, for example, on the graft material of a second part of a bifurcated stent graft that is to be deployed in the iliac artery opposite the long downstream leg of the bifurcated stent graft. One particular use is that these apices 8910 can be used to catch onto opposing apices of a stent from the second modular component. The multiple-stent 8900 can be used in any overlap region. Variations of the multiple-stent 8900 can include wire diameter, overall number of apices as well as the number of turns (filaments) used.

The multiple-stent 8900 can be made from a single wire circumferentially repeated as shown in FIGS. 89 through 94. The embodiment of FIG. 89 stacks the apices 8910 and the embodiment of FIG. 91 encircles the apices 9100. Alternatively, the multiple-stent can be a plurality of independent Z-stents intertwined with one another.

Figure 95:
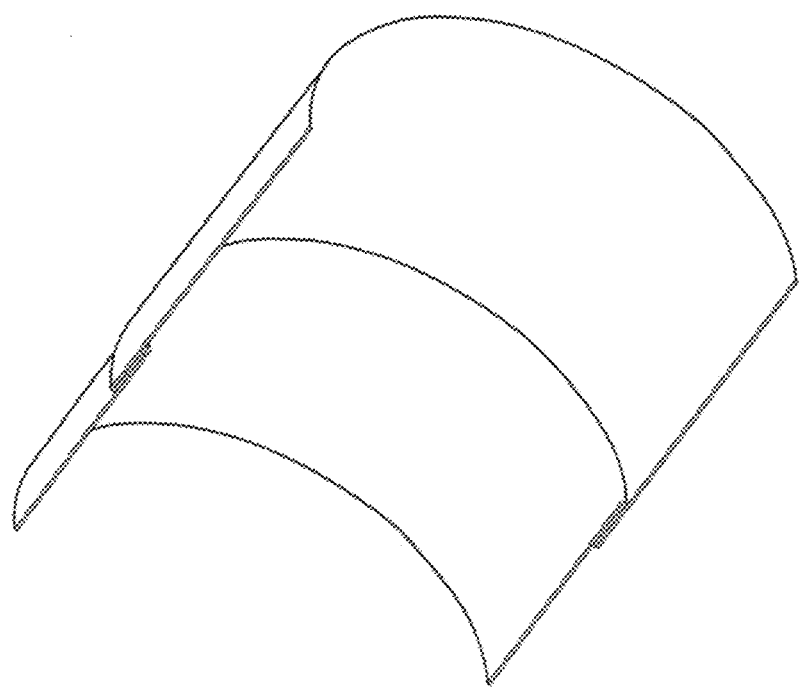
FIG. 95 is a representation of a modular component of a stent-graft system of the invention.
Figure 96:
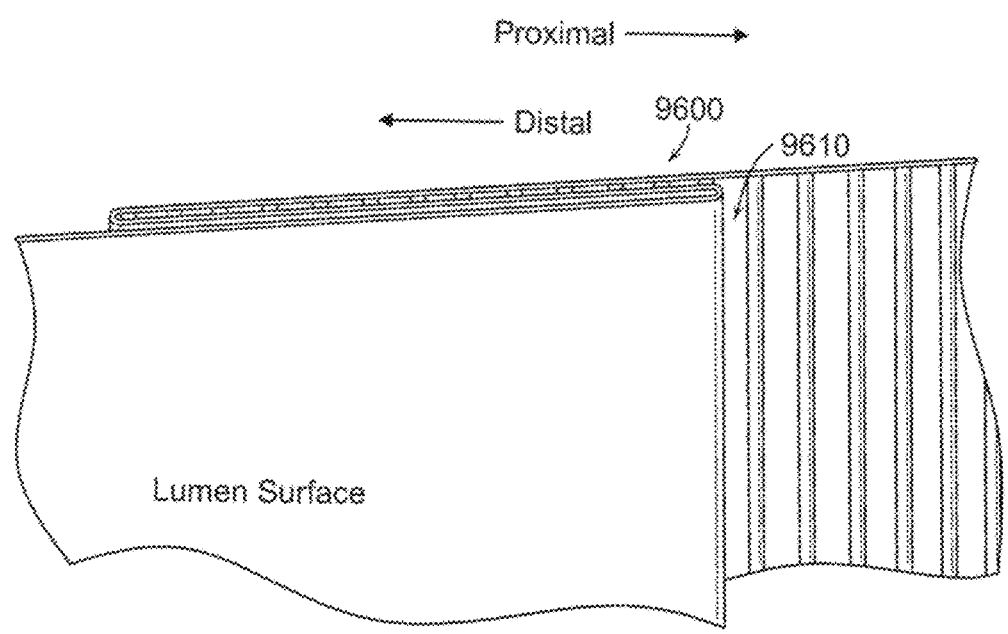
FIG. 96 is a representation of a modular component of a stent-graft system of the invention.
Figure 97:
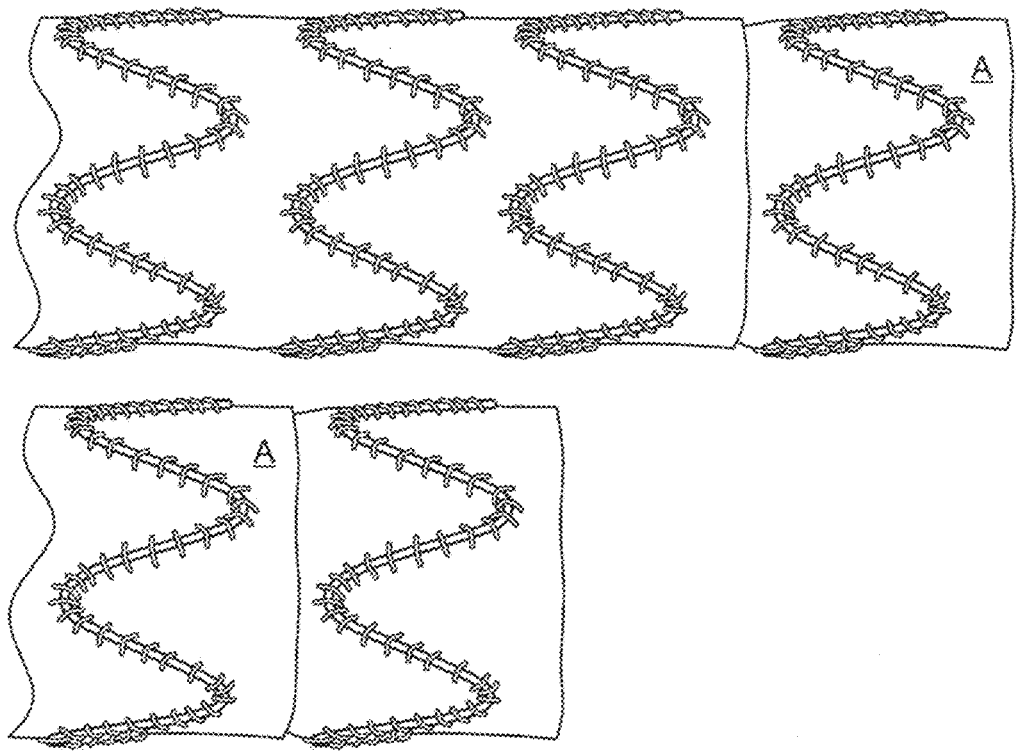
FIG. 97 is an embodiment of a stented graft of the invention.

To use the multiple-stent to connect two modular components of a stent-graft system, the graft and stent are assembled in a non-intuitive manner to achieve a high modular tensile strength. The graft is assembled such that its longitudinal length is shortened by folding the lumen in on itself in a longitudinal direction. This is done so that the total effective lumen is substantially unchanged, with respect to internal diameter. The ability to fold the lumen in on itself is done by sewing consecutive leg stents further from one another than would normally be done. FIG. 95 shows a cutaway graft with the surfaces on the bottom representing the portion of the lumen that is folded into the upper lumen. Overall, the graft is still a single lumen. FIG. 96 is a close-up of the in-folded area of the graft. Significantly, this fold 9600 creates a pocket 9610 facing the proximal end of the graft, when in the lumen of the graft. FIG. 97 is a photograph of an example of the configuration of FIGS. 95 and 96 applied to both iliac ends of a bifurcated stent graft. This particular example shows the fold between the last stent on the right and the stent immediately adjacent the last stent to the left in the figure. If desired, this configuration is set on both legs of the bifurcate as shown in FIG. 97.

These folds 9600 are placed in the areas of the stent graft that will receive modular components. Accordingly, the folds 9600 are made near the distal ends of stent graft components. These folds 9600 can be done at multiple points along the length, and can also be done at the very end, or at both locations. To keep the folds 9600 in place, longitudinal stitches are sewn through all the layers of the graft. These stitches are shown with reference "A" in FIG. 97. If the fold is at the end of a segment, like the stitch shown on the longer leg (top of FIG. 97), there will be two layers of graft material. If, in comparison, the stitch A is between two stents (bottom of FIG. 97), then three layers of graft material will be present. Folding of the graft components is done to create pockets on the lumen of the grafts. These pockets are used to receive the second component of the modular securement mechanism, the stent.

Figure 98:
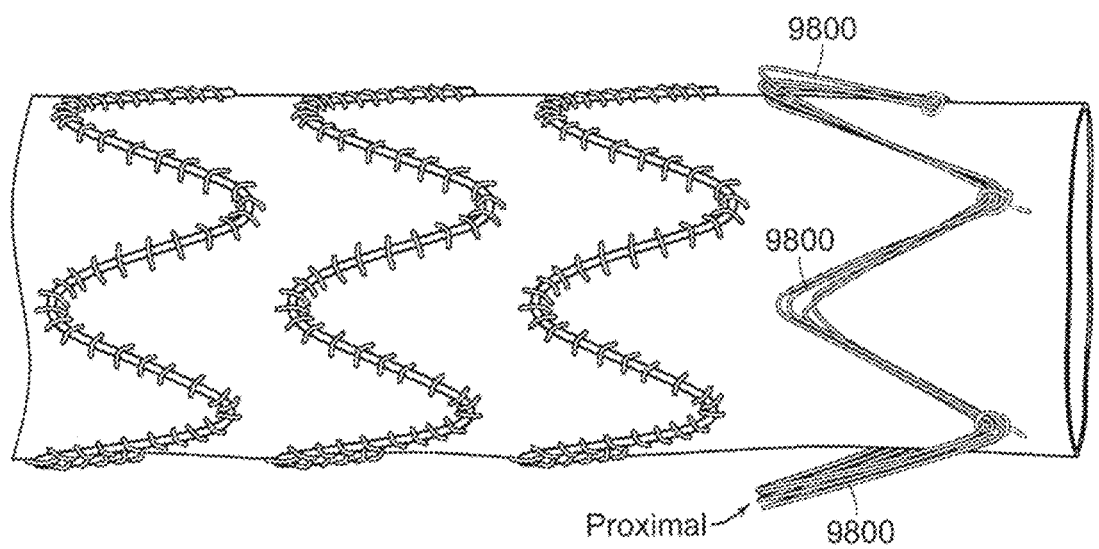
FIG. 98 is an embodiment of a stented graft of the invention.
Figure 99:
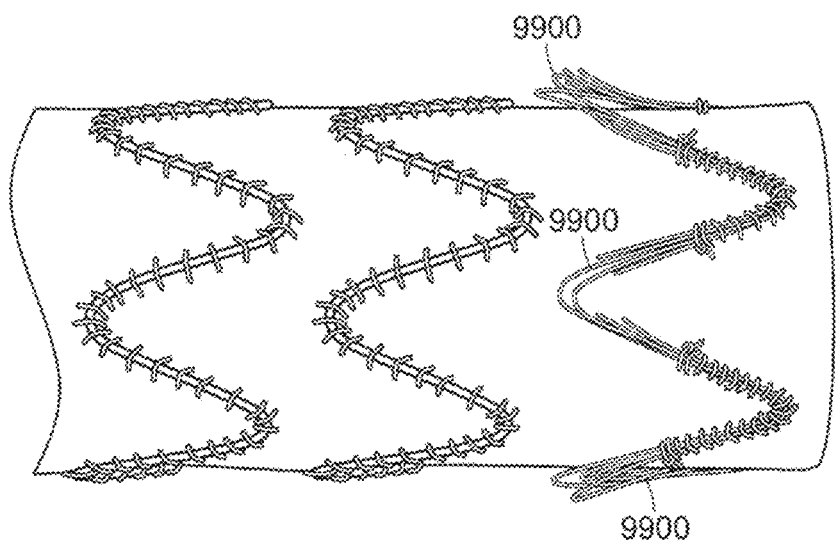
FIG. 99 is an embodiment of a stented graft of the invention.
Figure 100:
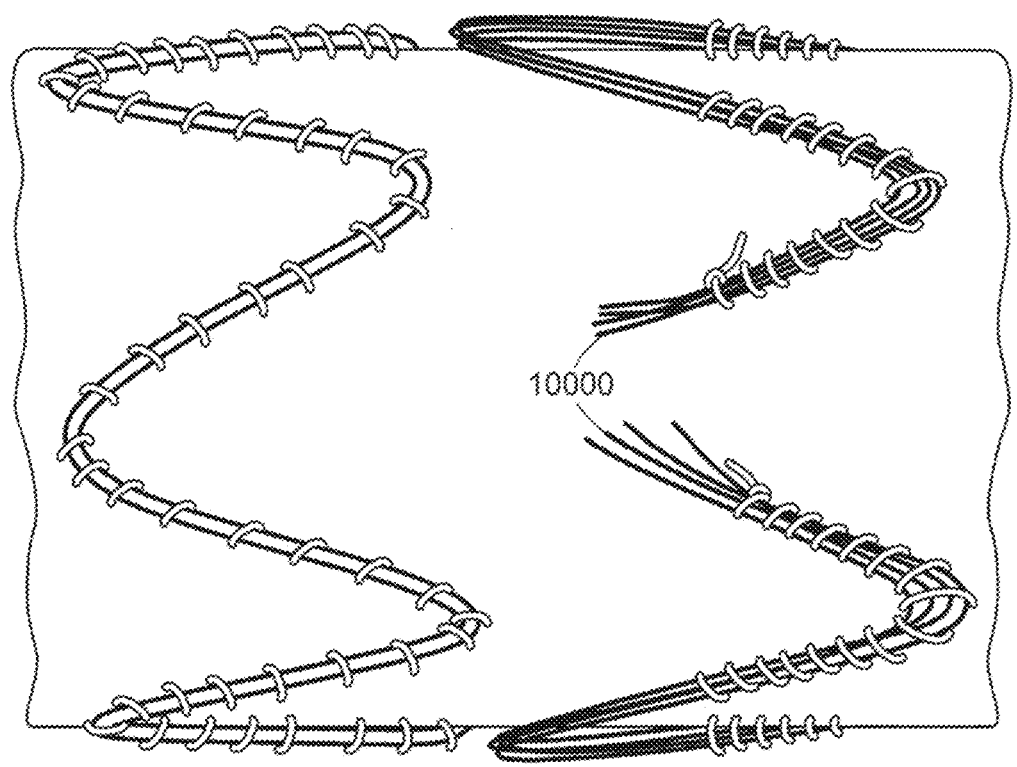
FIG. 100 is an embodiment of a stented graft of the invention.

The multiple-stent that is attached to a graft is found at or near the proximal end of the inserting component. The multiple-stent is attached in a manner that leaves the distally facing apices 9800 unsewn, as shown in FIG. 98. Also shown here is the multiple-stent configuration. By leaving the distally facing apices unsewn, they can fit into the pockets 9610 created by folding the graft of the first component. In addition to using the unsewn apices of stents to fit into the pockets 9610, a non-stent component can be added to the second component. Another alternative may include protruding features on the distal end of the stents. Some exemplary configurations of these features are shown in FIGS. 99 and 100. By having multiple filaments as depicted, it is more likely that at least some of the filaments' apices will engage with pockets 9610 in the connecting component. The total number of filaments is not critical, and a monofilament stent could also be sewn in the same manner.

The configuration shown in FIG. 99 differs from the configuration shown in FIG. 98 by having the sewing performed on a larger percentage of the proximal struts (adjacent the proximal apices). The extra sewing increases the security of the secure attachment to the stent graft of the engaging stent. Further, the distal apices 9900 are flared outward from the wall of the stent graft. The flaring of the distal apices 9900 is performed to increase the probability that some or all of the apices catch into the pockets of the opposing component. Additionally, some, but not all, of the filaments of the multi-filament stent are cut. The cutting of the filaments also creates additional independent catch points for the second component into the opposing first component. The concept behind cutting some (but not all) of the filaments is to maintain some radial force in that segment. The configuration shown in FIG. 100 shows a cutting of all of the distal apices 10000. This configuration creates a maximum number of catch points for the pockets 9610 (or other location). A trade off to this, as mentioned above, is that there is no radial strength in that area of the stent. The configuration of FIG. 100 only has a single apex cut. If desired, all or more than one apex could be cut in this matter.

Figure 101:
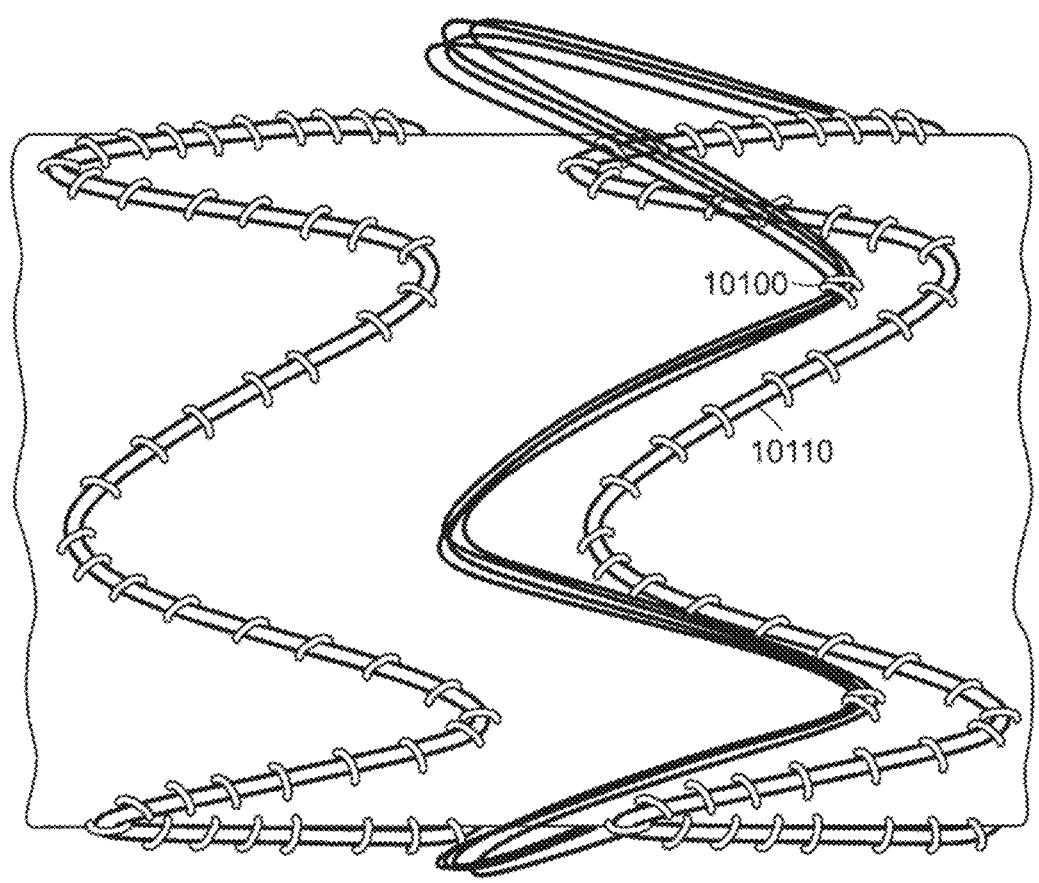
FIG. 101 is an embodiment of a stented graft of the invention.

The configuration shown in FIG. 101 modifies the configuration of FIGS. 98 to 100 by providing a partially sewn stent 10100 sewn right next to a fully sewn stent 10110. Two benefits to this modification immediately arise. First, radial strength is increased. This helps keep both stents against the lumen of the first component. Second, the configuration helps prevent possible in-folding of the second component that could block the lumen of the entire device. This type of in-folding would be the result of a poorly supported segment of the second component being placed under a significant axial load. If the distal apices or other protruding members have caught the pockets of the first component, then the top (proximal) apices could fold into the lumen. Another way to prevent this potential issue of in-folding due to an axial load could be to provide a fully supported stent proximal to the stent intended to engage with the first component.

Figure 102:
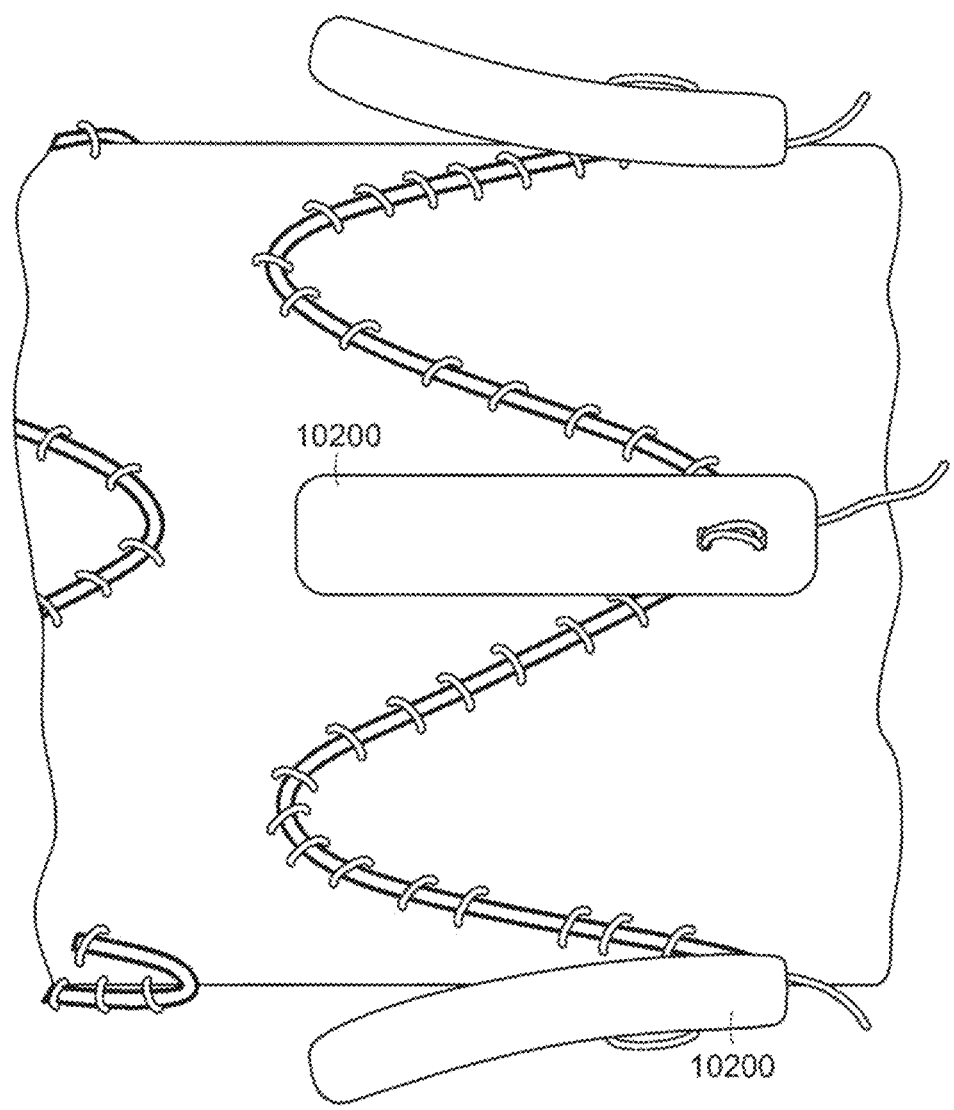
FIG. 102 is an embodiment of a stented graft of the invention.

The configuration shown in FIG. 102 illustrates non-stent components 10200 used to engage the pockets 9610 (FIG. 96) of the first component. Here, a bio-compatible plastic or polymer is the shape of a closed ladder with interior steps, any of the steps can be connected to the stent graft. As shown in FIG. 102, the upstream-most step is connected to the cranial (upstream) stent at each of the upstream apices. Of course, less than the number of such apices of the component 10200 can be connected to non-stent component 10200. A desirable shape has the distal end (downstream) curved outward to capture the pocket 9610 or vessel wall. One benefit of using a non-stent component 10200 is a non-metal reduces wear between adjacent components. These non-stent components 10200 can be put at some or all of the apices of some or all of the stents, or between stents.

Figure 103:
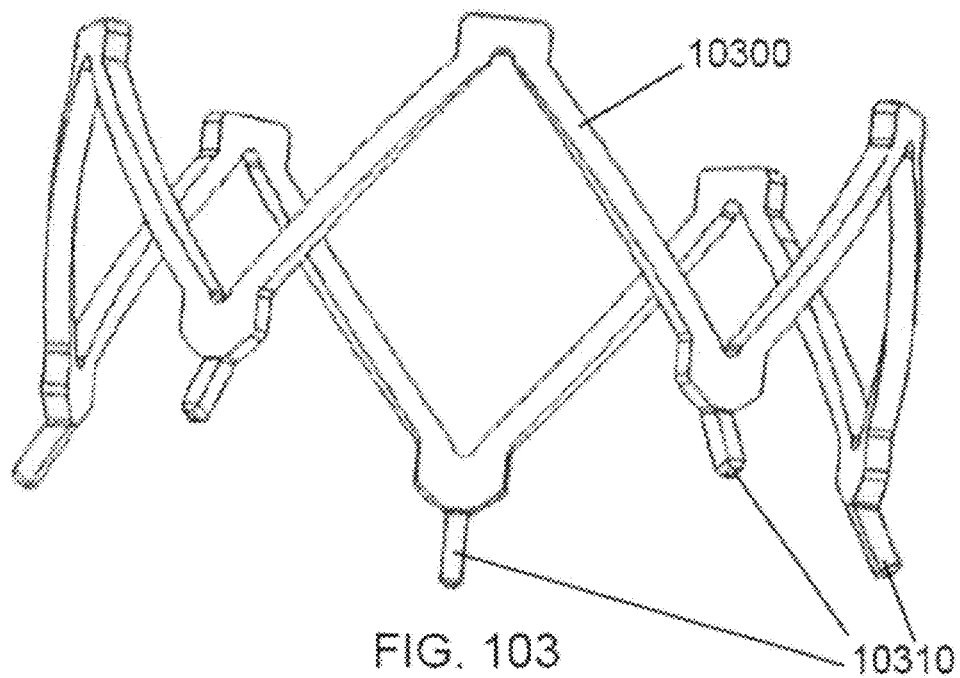
FIG. 103 is an embodiment of a stent of the invention.
Figure 104:
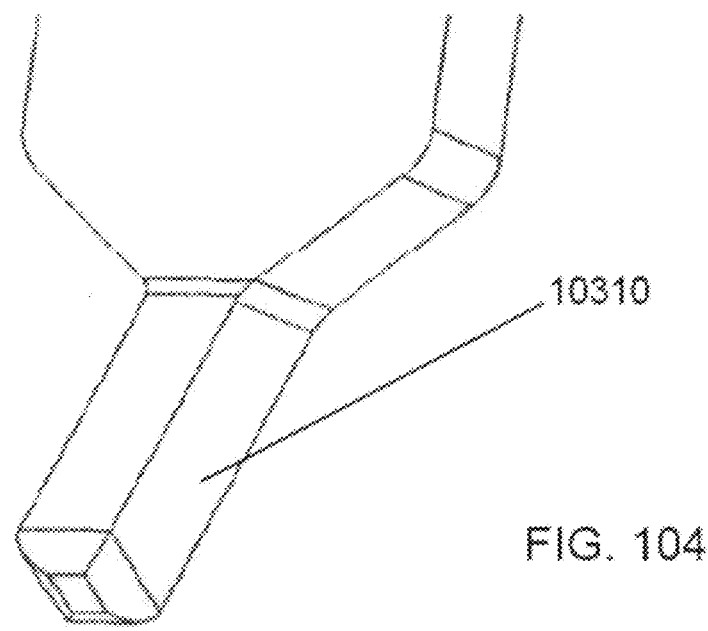
FIG. 104 is an embodiment of a stent of the invention.

Another exemplary embodiment of devices that can be used to connect into the pocket 9610 (FIG. 96) or the vessel wall is shown in the variations of FIGS. 103 through 104. The stent 10300 with its downstream capture pegs 10310 can be used in the modular stent securement mechanisms described herein. In this embodiment, the distally forcing pegs 10310 of the stent are flared out and are not sharpened. With this variation, the distally facing pegs 10310 are not intended to penetrate through the fabric of the first component in which the pegs 10310 are to be connected. In such a configuration, the distally facing pegs can end up in a pocket 9610 (FIG. 96) created in the first component.

In still another embodiment, and referring to FIGS. 78A and 78B, the invention is a stent graft system 7809 comprising a first stent graft 7820 that includes a first luminal graft component 7840 a plurality of outside stents extending along and fixed to an outside surface of the first luminal graft component 7840 and an inside stent 7860 between two outside stents 7861, 7871, one of which is at a distal end 7880 of the first luminal graft component 7840 the inside stent 7860 fixed to an inside surface of the first luminal graft component 7840 and having a plurality of barbs 7863 pointed generally proximally within the first luminal graft component 7840; and a second stent graft 7873 that includes a second luminal graft component 7874 and a plurality of outside stents 7875 extending along and fixed to an outside surface of the second luminal graft component 7873, whereby insertion of the second stent graft 7873 into the distal end 7880 of the first luminal graft component 7840 to overlap at least two stents of each of the first 7820 and second stent grafts 7873 will cause interfering relation between at least a portion of the barbs 7863 with a stent of the second luminal graft component 7874 of the second stent graft 7873. Examples of maximum and minimum overlap of the first and second stent grafts are shown in FIGS. 79A and 79C.

The first luminal graft component 7840 of the stent graft system 7809 can be bifurcated and the inside stent 7860 located in one of two legs of the first luminal graft component 7840.

The stent graft system of the invention can further include a plurality of outside stents 7891 extending along and fixed to an outside surface of a second leg 7890 of the bifurcated first luminal graft, and a second inside stent 7892 between two outside stents, one of which is at a distal end 7893 of the second leg 7890, the second inside stent 7892 fixed to an inside surface of the second leg 7890 and having a plurality of barbs 7894 pointed generally proximally within the second leg 7890.

Figures 79A, 79B, 79C:
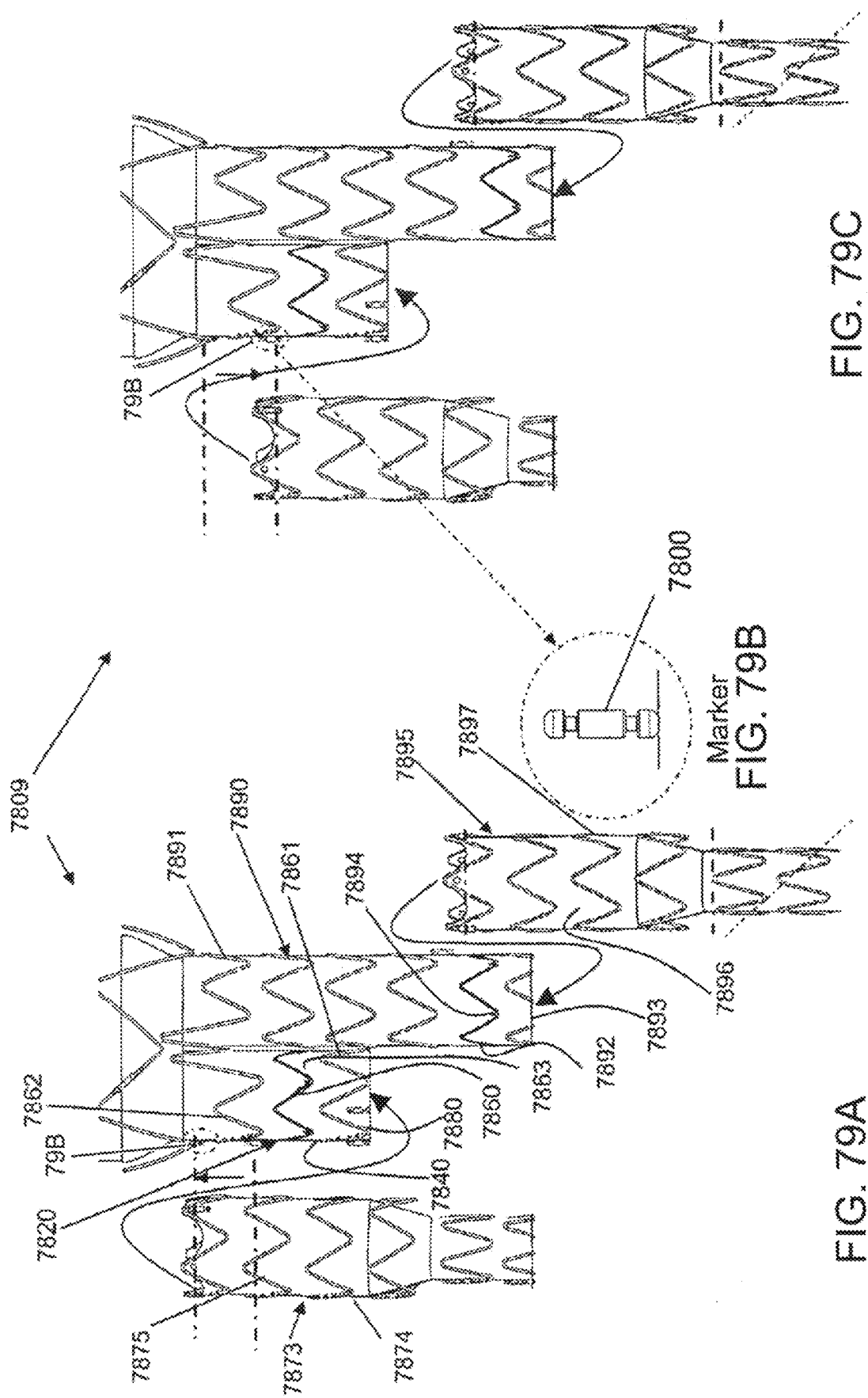
FIGS. 79A, 79B and 79C are embodiments of a telescoping stent grafts system of the invention.
Figure 80:
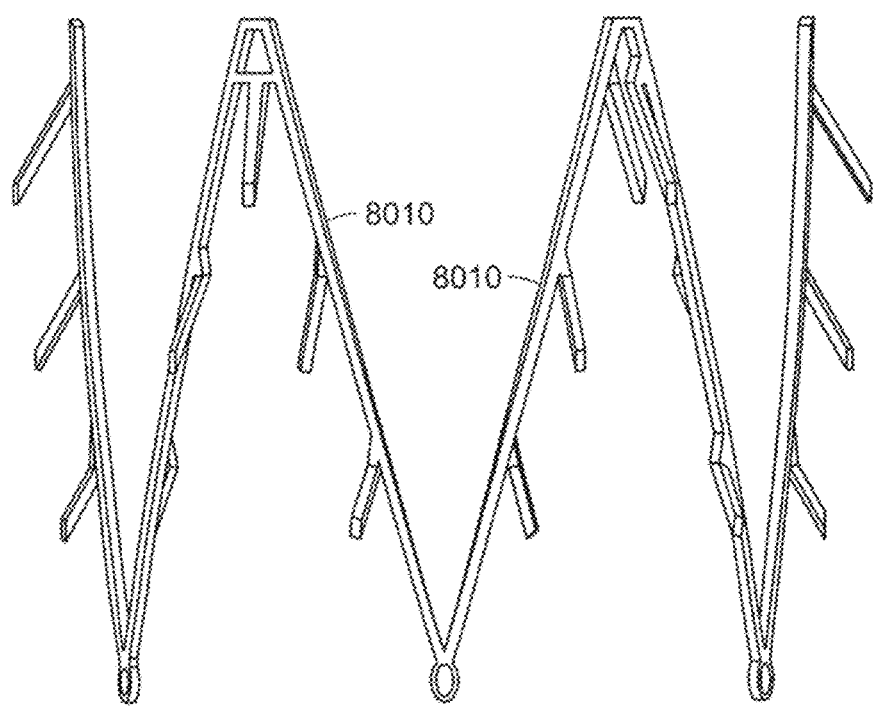
FIG. 80 is an embodiment of a stent of the invention.
Figure 83:
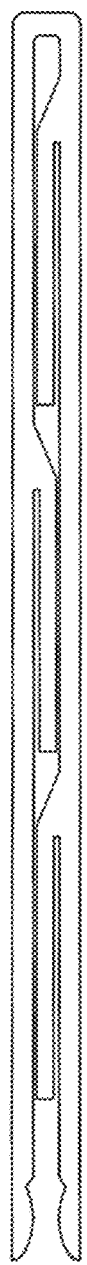
FIG. 83 is a representation of an unexpanded stent of the invention.
Figure 84:
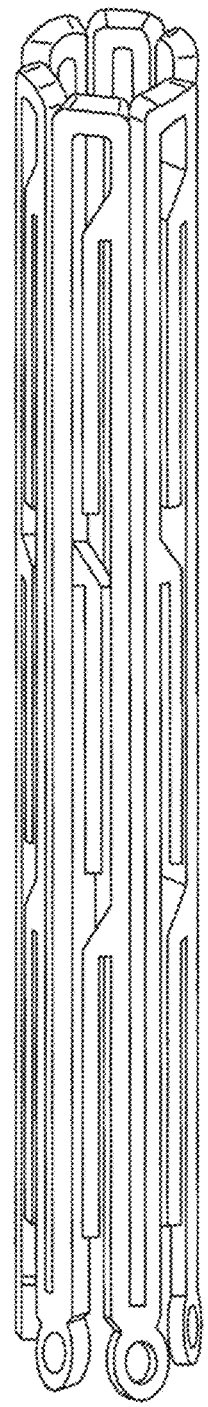
FIG. 84 is a representation of an unexpanded stent of the invention.

A third stent graft 7895, shown in FIG. 79A includes a third luminal graft component 7896 and a plurality of outside stents 7897 extending along and fixed to an outside surface of the third luminal graft component 7896, whereby insertion of the third stent graft 7895 into the distal end 7893 of the second leg 7890 to overlap at least two stents of each of the second leg 7890 and stent graft 7895 will cause interfering relation between at least a portion of the barbs 7894 with a stent or the third luminal graft component 7896 of the third stent graft 7895.

Stents of the stent graft system of the invention can be formed, at least in part, of a superelastic metal, such as nitinol.

Figure 105A:
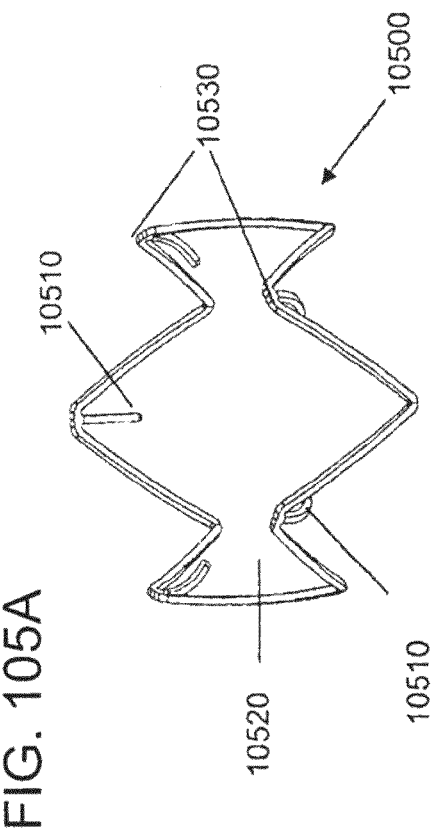
Figure 106:
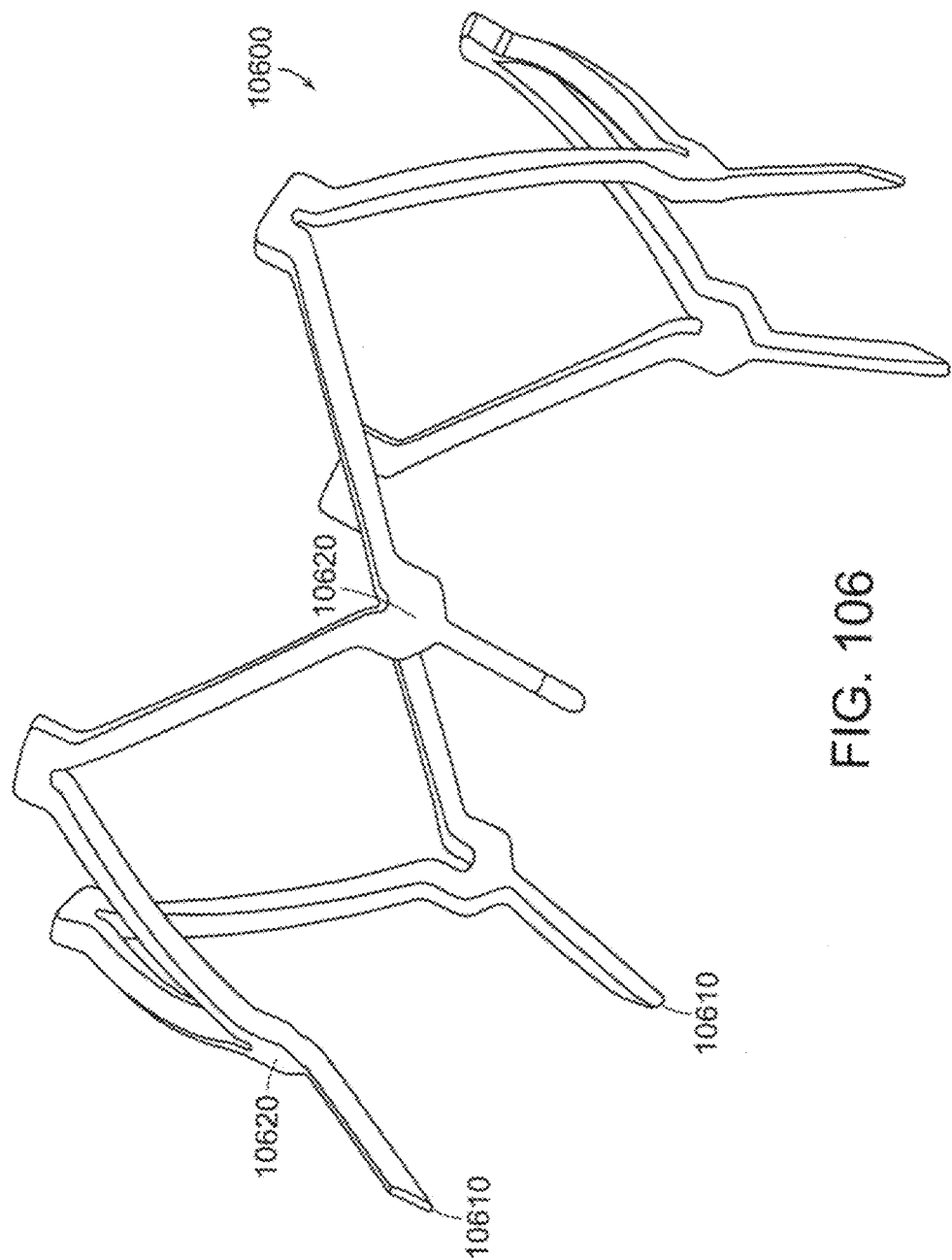
FIG. 106 is an embodiment of a stent of the invention.

The variation shown in FIG. 105A is a stent 10500 with pegs 10510 projecting downstream, not from the downstream apices 10520, but from the upstream apices 10530. In the variation shown in FIG. 106, the stent 10600 has sharpened legs 10610 projecting from the downstream apices 10620. Caudally facing barbs can be disposed on any number or all apices of a leg stent. Sharpened barbs can penetrate the graft material of the prosthesis into which the graft is placed. In many cases, this configuration would be a bifurcate, but could also be a previously placed leg extension.

A further embodiment of the invention is a telescoping stent graft system, which is essentially identical to the stent graft system shown in FIGS. 79A and 79C, but lacks at least one set of barbs 7863 and 7894. In this alternative embodiment, the bifurcated first stent graft includes a bifurcated first luminal graft component, a plurality of outside stents extending along and fixed to an outside surface of one of two legs of the bifurcated first luminal graft component. Optionally an inside stent extends between two outside stents, one of which is at a distal end of the first luminal graft component, the inside stent fixed to an inside surface of the first luminal graft component. A second stent graft that includes a second luminal graft component and a plurality of outside stents extending along and fixed to an outside surface of the first luminal graft component, whereby the second stent graft can be inserted into the distal end of a first of two leg components of the bifurcated first luminal graft component to overlap at least two stents of each of the first and second stent grafts; a plurality of stents (e.g., outside stents and/or inside stents) extending along and fixed to an a surface (e.g., outside surface and/or inside surface) of a second leg of the bifurcated first luminal stent graft. Optionally, a second inside stent is located between two outside stents, one of which is at a distal end of the second leg, the second inside stent fixed to an inside surface of the second leg. Also, optionally, a third stent graft is included having a third luminal graft component and a plurality of outside stents extending along and fixed to an outside surface of the third luminal graft component, whereby insertion of the third stent graft can be inserted into the distal end of the second leg of the bifurcated first luminal graft component to overlap at least two stents of each of the first and second stent grafts. Regardless, the first leg is shorter than the second leg, and the first leg includes at least one more stent than is required for overlap of at least two stents of each of the second stent graft.

In an embodiment, one leg of the bifurcated stent graft of the invention can shorter in length (i.e., first or short leg) in the other leg (i.e., second or long leg) of the bifurcated stent graft, as shown in FIGS. 78A, 78B, 79A and 79C. When the bifurcated stent graft of the invention is placed in the abdominal aorta, the long leg of the bifurcated stent graft can be in the common iliac, as represented, for example, in FIG. 72A, or in the aorta.

As shown in FIGS. 78A and 78B, the bifurcated first stent graft of the telescoping stent graft system of the invention can include at least one radiopaque marker 7800. In a particular embodiment, the shorter leg of the bifurcated first stent graft includes three lateral radiopaque markers 7801, 7802, 7803, one of which is at the distal opening of the short leg, another of which is at the proximal end of the apex of an inside stent (i.e., second stent from the leg opening) and the third of which is at the point of bifurcated on the first stent graft. The radiopaque marker 7802 located at the apex of the inside stent can delineate the minimum (min) positioning of the third stent graft and the radiopaque marker 7803 can delineate the maximum (max) positioning of the third stent graft, as shown in reference to, for example, FIGS. 78A, 78B, 127A, 127B, 127C and 127D. Two additional radiopaque markers 7804, 7805 are distributed about the distal opening of the short leg. Radiopaque marker 7806 is located at a proximal end of an inside stent in the long leg of the bifurcated first stent graft.

The delivery systems, components of delivery systems, stents, grafts and stent graft systems of the invention can be employed in methods of treating aortic aneurysms, such as abdominal aortic aneurysms.

In another embodiment, the invention is a method for treating an abdominal aortic aneurysm, comprising steps of directing a sheath and distal tip of a delivery system to an abdominal aortic aneurysm of a patient through an artery, such as a femoral artery that can subsequently pass through a common iliac artery, of the patient, the sheath containing a bifurcated stent graft; rotating a lead screw nut of the delivery system that is threadably linked to the sheath to thereby retract the sheath at least partially from the bifurcated stent graft; and sliding the lead screw nut along a handle body of the delivery device while the lead screw nut is threadably linked to the sheath to thereby further retract the sheath, whereby the bifurcated stent graft is at least partially deployed in the abdominal aortic aneurysm, thereby treating the abdominal aortic aneurysm.

The method of treating an abdominal aortic aneurysm can further including the step of opening a clasp at a distal end of the delivery device to release a bare stent at a proximal end of the bifurcated stent graft. A portion of a first leg of the bifurcated stent graft can be retained within the sheath when the clasp is opened to release the bare stent. The first leg of the bifurcated stent can be retained by fixing a stent at a distal end of the first leg between the sheath and a leg clasp. The first leg of the bifurcated is the longer of two legs of the bifurcated stent.

In another embodiment, the clasp employed in the method to treat an abdominal aortic aneurysm can distend struts of the proximal stent toward a major axis of the delivery system when the sheath has been retracted sufficient to expose the bare stent.

The method to treat an abdominal aortic aneurysm can further include the step of cannulating a second leg of the bifurcated stent with an extension stent graft while the first leg is being held at least partially within the sheath. During cannulation, the leg that is being held is longer than the leg that is being cannulated and, optionally, the cannulated leg is in telescoping relation with the extension stent graft. The cannulated leg can overlap the extension stent graft by at least two stents of each of the cannulated leg and the extension stent graft. The cannulated leg can include at least one more stent than is required to overlap the extension leg by two stents of each of the cannulated leg and the extension stent graft. A stent second from the distal end of the cannulated leg can be within the graft of the bifurcated stent graft. The stent second from the distal end of the bifurcated graft can include barbs that extend inwardly and proximally from the stent.

In another embodiment, the method of treating an abdominal aortic aneurysm can further include the steps of releasing the bifurcated stent graft from the leg clasp, and then detaching a slider and the sheath from the remainder of the delivery device and withdrawing the remainder of the device from the patient while leaving the slider and sheath substantially in place and, optionally, further including the step of deliverying a second extension through sheath and to the first leg and cannulating the first leg with the second extension. The cannulated second leg can overlap the extension stent graft by at least two stents of each of the cannulated first leg and the second extension. The cannulated first leg can include at least one more stent than is required to overlap the extension leg by two stents of each of the cannulated first leg and the second extension. A stent second from the distal end of the cannulated first leg can be within the graft of the bifurcated stent graft. The stent second from the distal end of the bifurcated graft includes barbs that can extend inwardly and proximally from the stent.

The methods of the invention have an advantage of repositioning of a graft (e.g., bifurcated graft, second stent graft, third stent graft) if, for example, a clinician determines initial positioning of the graft is less than optimal. The graft can be repositioned at its proximal and distal end and proximally and distally in an aorta or branch of an aorta, such as a common iliac artery.

Figure 105B:
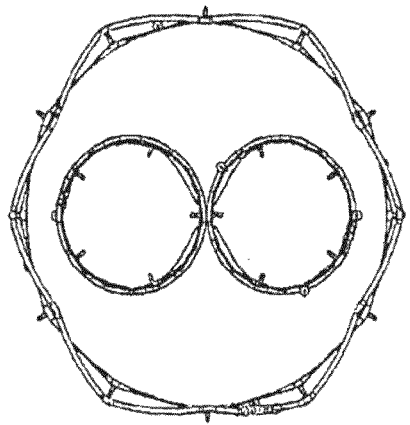

FIGS. 105A, 105B and 105C represent embodiments of a stent and use of stent in a telescoping stent graft system of the invention.

Figure 108:
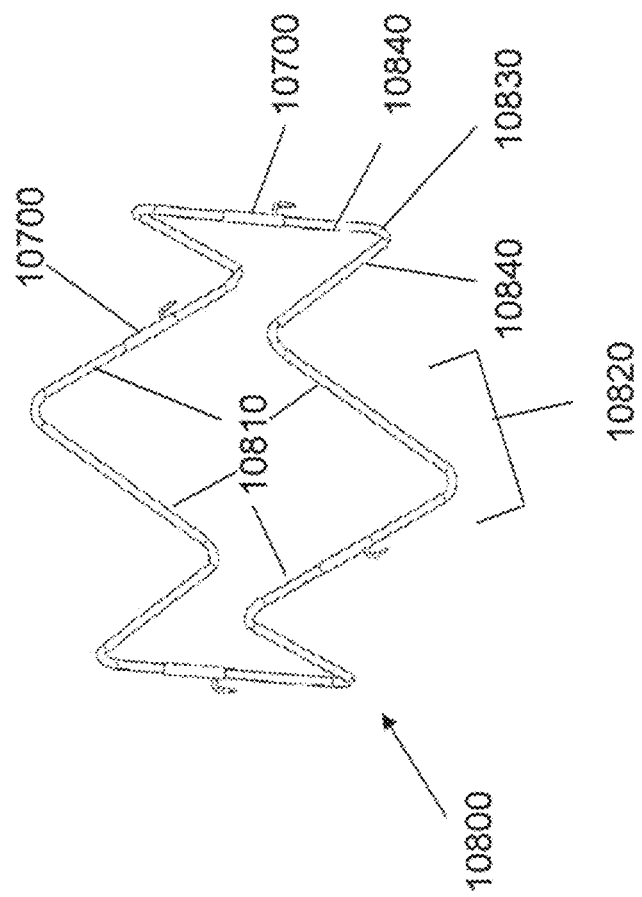
FIG. 108 is an embodiment of a stent of the invention.
Figure 107:
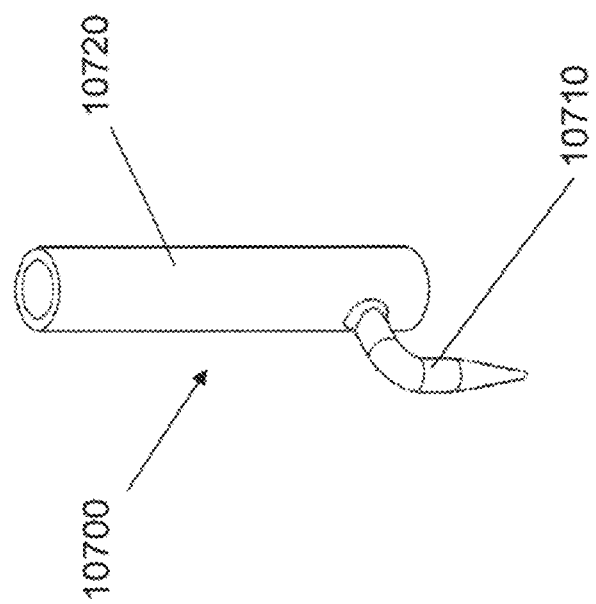
FIG. 107 is an embodiment of a barb of the invention.
Figure 109:
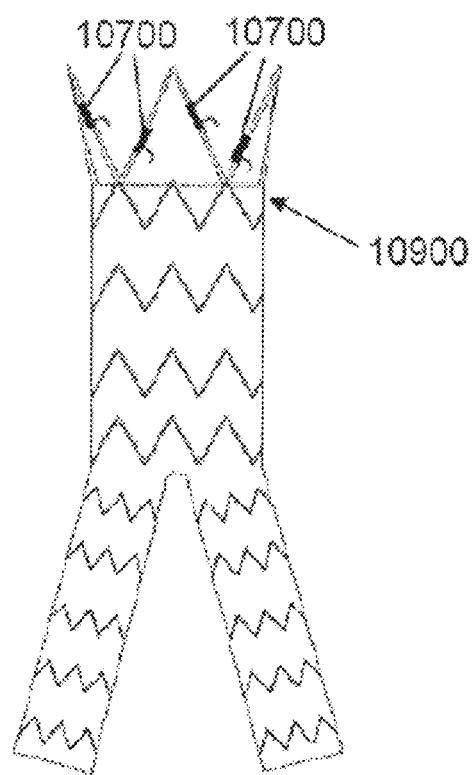
FIG. 109 is an embodiment of a stent graft of the invention.

FIGS. 107 to 109 illustrate various configurations for incorporating hooks or barbs to Z-stents, in particular, bare stents, without using the material of the stent itself. FIG. 107 illustrates an exemplary embodiment of a crimp hook 10700 according to the invention. A hook 10710 is attached to or integral with a crimp sleeve 10720 that is to become part of a bare stent 10800 (bare spring) on an endoluminal stent graft prosthesis. Many Z-stents are already connected at the two ends by a crimp sleeve to complete the circumference. The configuration adds active fixation of the stent graft assembly, once deployed, into the surrounding tissue of the vessel to prevent migration of the prosthesis post-deployment. To create the crimp hook 10700, for example, the hook 10710 (which can be a pointed or sharpened wire if desired) can be welded onto the body of the crimp sleeve 10720. The crimp hook 10700 is, then, attached to the ends of the bare stent 10800 by crimping (or welding) it to the strut 10810. If multiple crimp hooks 10700 are desired, the crimp hooks 10700 can be connected to individual stent portions 10820 defined by one apex 10830 and two halves of struts 10840, for example.

Alternative to the exemplary tubular structure shown in FIG. 107, the crimp sleeve 10720 can be a clamshell that is placed over two adjacent halves of a strut 10840 (or just a single, unbroken strut 10840) and crimped thereon. After the bare stent 10800 is equipped with the crimp hooks 10700, it can be affixed to the end of the stent graft 10900 as shown in FIG. 109. The crimp hooks 10700 in FIG. 109 are shown as rotated around the respective struts 10840 of the bare stent 10900 so that they can be seen in the figure of this drawing. In use, however, the hooks 10710 will, for best apposition with the vessel wall, be pointed substantially radially outward from the longitudinal central axis of the stent graft.

Figure 111:
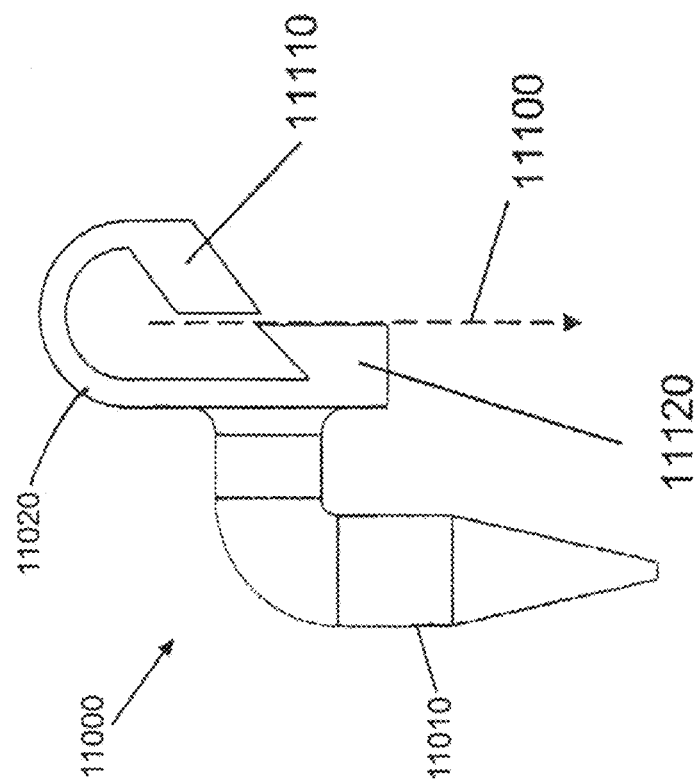
FIG. 111 is an embodiment of a barb of the invention.
Figure 110:
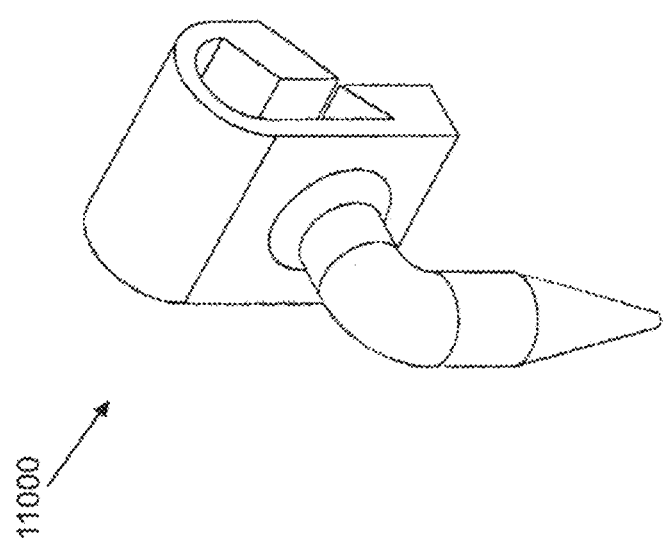
FIG. 110 is an embodiment of a barb of the invention.
Figure 113:
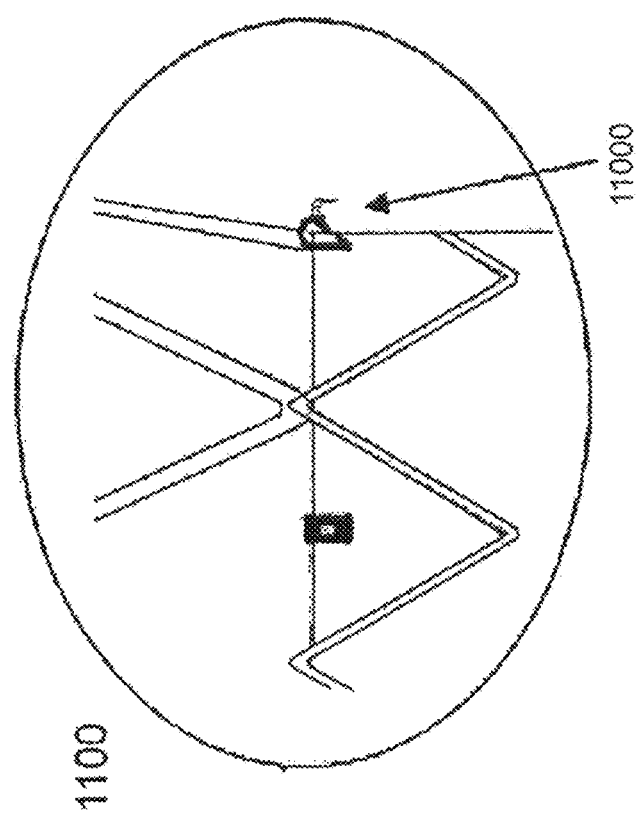
FIG. 113 is an embodiment of a stent graft of the invention.
Figure 112:
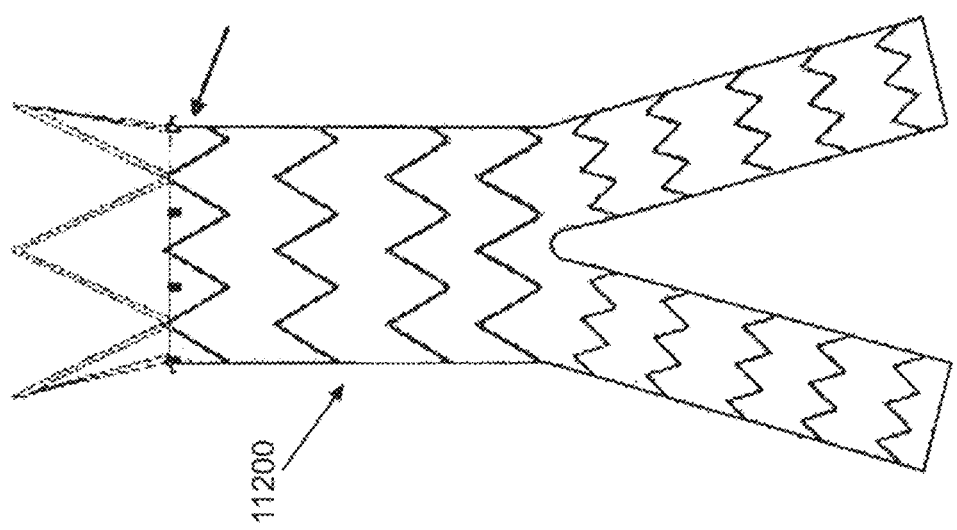
FIG. 112 is an embodiment of a stent graft of the invention.

In contrast to the bare stent crimp hooks above, FIGS. 110 and 111 illustrate a crimp hook 11000 that is attached/affixed to the edge of the main body of the graft 11200, as shown in FIGS. 112 and 113. With the configuration shown, the crimp hook 11000 slides over the edge of the graft material (illustrated with a dashed line 11100) and is compressed so that the two edges 11110, 11120 of the crimp pinch the graft material 11100 therebetween to create a mechanical lock onto the graft material 11010. This configuration adds active fixation of the stent graft assembly, once deployed, into the surrounding tissue of the vessel to prevent migration of the prosthesis post-deployment. Like above, the hook 11010 can be welded to the crimp body 11020, for example, or can be integral therewith.

It is noted that providing barbs or hooks on the bare stent of the stent graft (tube or bifurcated) increases the possibility of disadvantageous puncture or scraping, whether to the outer sheath or to the interior of the vessel wall. In particular, with regard to the stent embodiments of FIGS. 73 to 76, 79 to 85, and 103 to 106, for example, it would be desirable to entirely prevent the possibility of inadvertent damage to either the outer sheath or the vessel wall. To prevent such damage from occurring, the delivery system according to the invention employing bare stents having such barbs is provided with a material umbrella 11400.

Figure 114:
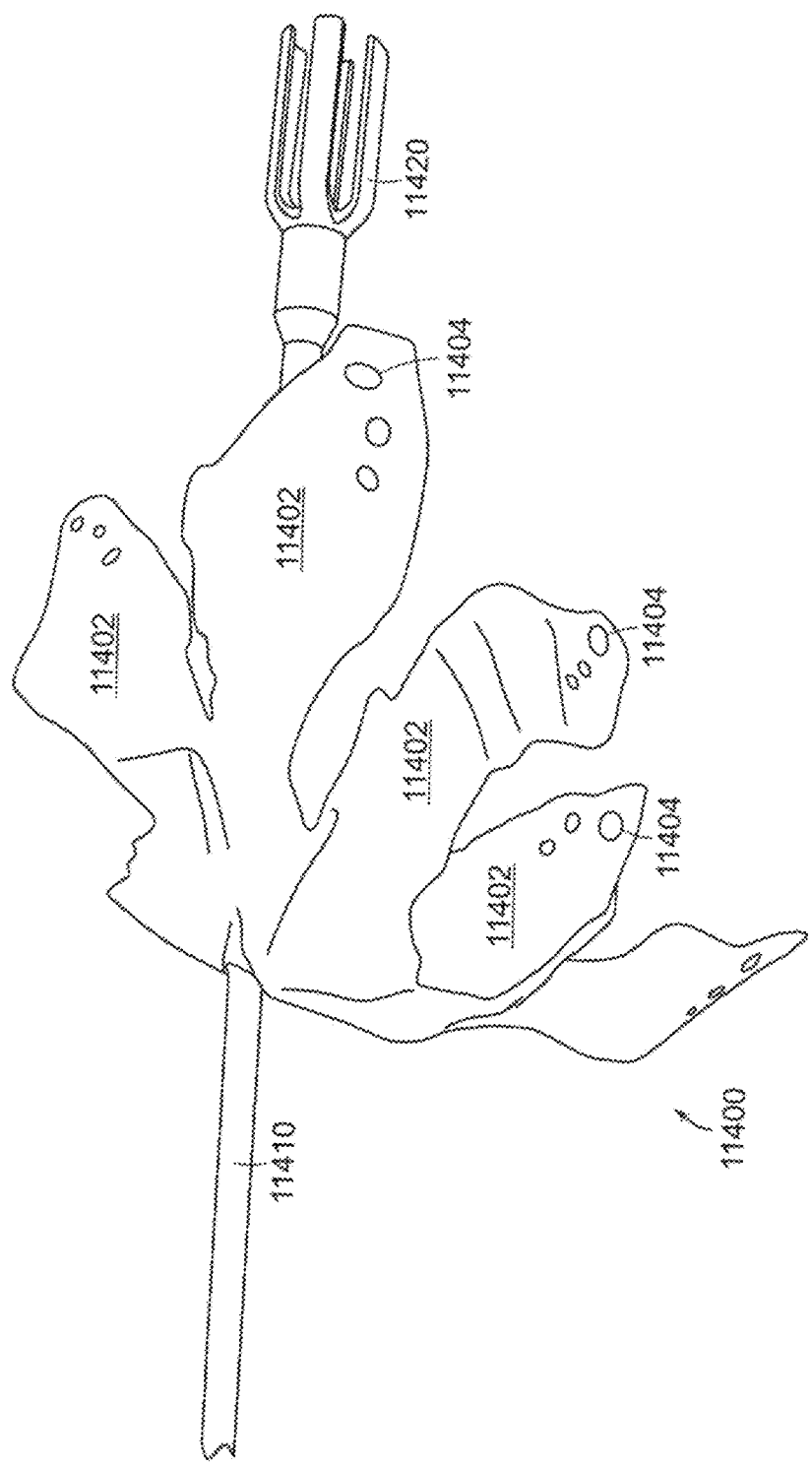
FIG. 114 is a further embodiment of a component of the delivery system of the invention.
Figure 115:
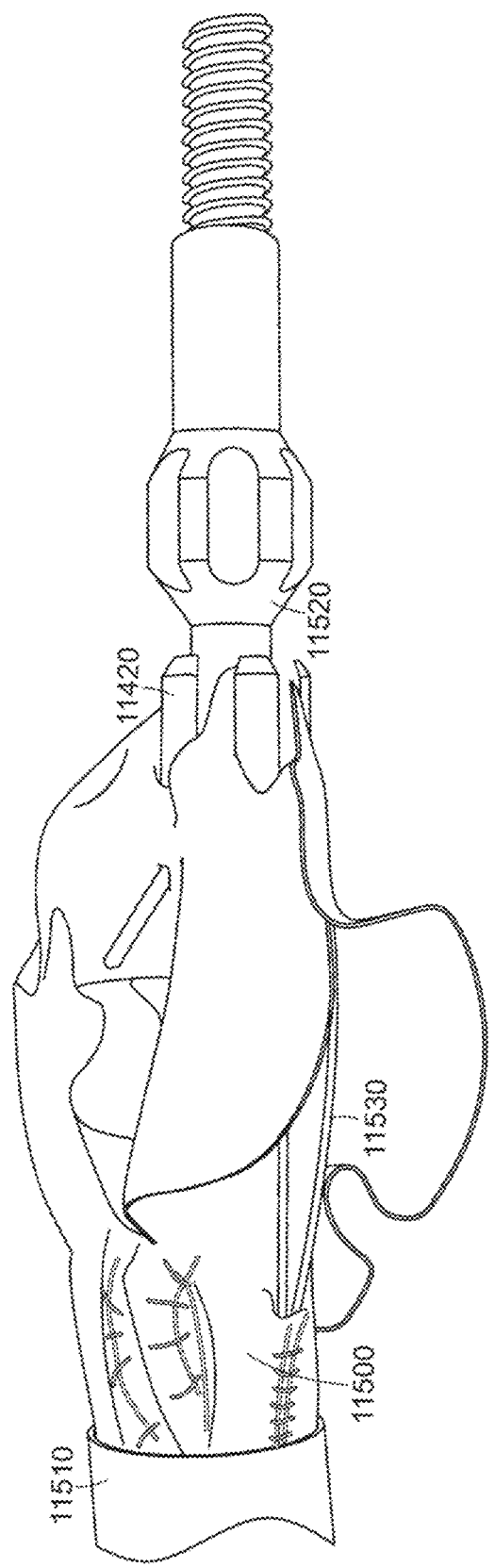
FIG. 115 is a further embodiment of a component of the delivery system of the invention.
Figure 116:
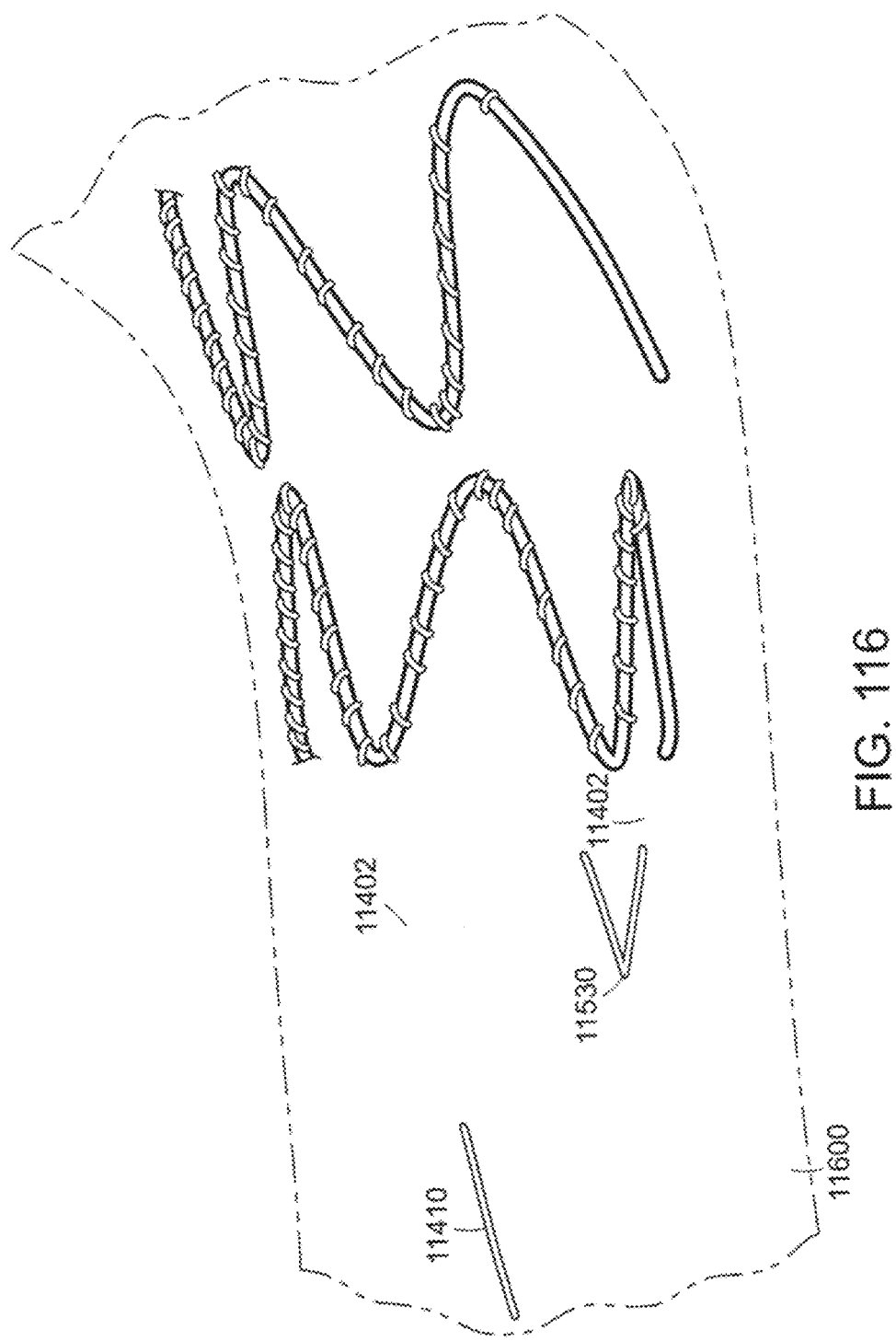
FIG. 116 is a representation of a stent graft system of the invention as viewed following placement in a mock-silicon aorta.
Figure 121:
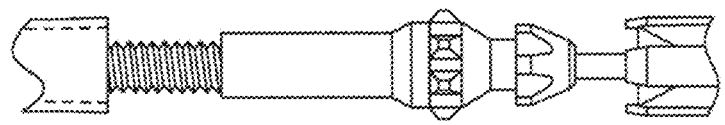
Figure 122:
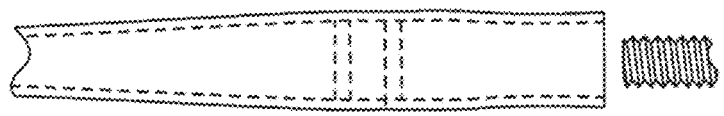
Figure 123:
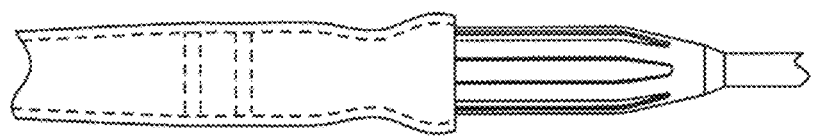
Figure 124:
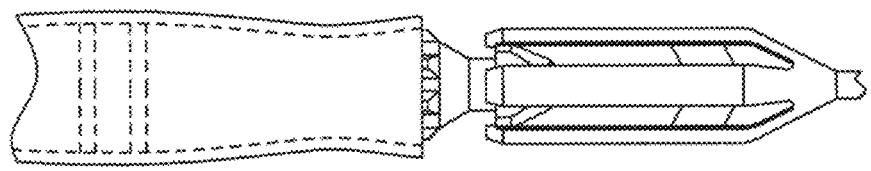

In one exemplary embodiment illustrated in FIG. 114, the umbrella 11400 is attached (slideably or fixedly) to the lumen 11410 controlling the proximal apex capture portion 11420. When the stent graft 11500 is collapsed and loaded within the outer sheath 11510, and is captured within the proximal apex capture device 11420, 11520 (as shown in FIG. 115), the bare stent 11530 spans the distance between the leading edge of the graft and the apex capture device 11420, 11520. The umbrella 11400 can be disposed outside the stent graft (and inside the outer sheath 11510) but, in the exemplary embodiment shown in FIGS. 114 and 115, the umbrella 11400 is held by the lumen 11410 interior to both the umbrella 11400 and the outer sheath 11510. Arms 11402 of the umbrella 11400 extend therefrom between respective apices of the bare stent 11530. The arms 11402 are relatively narrow at the intermediate portion where each is passing through the apices and expand to be relatively wide at their distal ends. In such a configuration, the distal ends of each arm 11402 can spread out over the adjacent bare stent apices and, if wide enough, overlap with adjacent other arms 11402 to canopy out around the entire circumference of the exposed bare stent 11530 as shown in FIG. 115. At least one passage 11404 is formed at the distal portion of the arm 11402 so that a respective tine of the proximal apex capture portion 11420 can extend therethrough. In this configuration, the wide distal portions of the arms 11402 are controlled and stay against the bare stent, protecting the outer sheath 11510 and interior vessel wall up until the time when the apex capture device 11420, 11520 is actuated (a position that is shown in FIG. 115 but the bare stent 11530 and the arms 11402 have not yet been released from the tines of the proximal apex capture portion 11420). FIG. 116 is photograph depicting how the umbrella 11400 protects the interior of the vessel wall 11600 before the delivery system has retracted the inner lumen 11410. As the inner lumen 11410 is retracted, the umbrella 11400 will slide out from between the bare stent 11530 and the vessel wall 11600.

In an exemplary embodiment where infra-renal barbs of the stent graft are not desired, they can be moved higher on the bare stent so that they can be covered by the fabric strips of the umbrella 11400.

FIGS. 117 to 124 illustrate a concept according to the invention that uses a proximal clasp to expand the taper tip and create/improve a seal between the nose cone/tip and the outer sheath, the interface eliminating pronouncement of the outer sheath edge by taking up the space between the tip and the outer sheath. The delivery systems described herein (e.g., AAA delivery systems), the concept of removing the inner components of the delivery system (tip/support member) while leaving the outer sheath behind requires the tip to be smaller than the ID of the outer sheath. Due to the smaller shape of the tip, the problem of "fish mouthing" can occur at the tip-sheath interface. "Fish mouthing" occurs when the edge of the sheath becomes pronounced when the tip sheath interface is navigating the vessel, which could potentially score the vessel wall, see FIGS. 117 and 118. To solve the problem the space between the tip and the sheath needs to be eliminated but still allow for removal of the tip. See FIGS. 119 to 120. To accomplish this removal of material underneath the distal claps and allowing the proximal clasp to be moved more forward so that the taper tip can be expanded over the clasp taking lip the space between the sheath and tip.

FIGS. 125 and 126 illustrate an exemplary embodiment of a passive proximal retainer 12500 for the AAA bifurcated stent graft according to the invention, which retainer 12500 is referred to herein as a spoked hub. A proximal retainer is required for the ipsilateral leg of the AAA bifurcated stent graft. The proximal fixation holds the stent graft in the deployment sheath during cannulation of the contralateral leg with the guidewire and the leg stent. The passive proximal retainer device 12500 is a hub fitted to the support member at the proximal end of the stent graft. The passive proximal retainer device 12500 has spokes 12502 radiating out from a central hub 12504. The number of spokes is equivalent to the number of struts on the proximal end of the stent. The spokes are engaged and trapped by the individual struts of the stent during the loading process. The stent graft is loaded into the deployment sheath through the use of a funnel. When the proximal end of the stent is just about in the deployment sheath, the support member is loaded next to the graft and the spokes of the hub are engaged in the graft struts. The graft and support member are, then, pulled into the sheath. During deployment of the stent, the graft will not be released from the sheath until the sheath is fully retracted over the spoked hub. The outer diameter (OD) of the spokes are about 0.008 inches less than the inner diameter (ID) of the sheath, therefore, the stent struts are trapped by the spoked hub until the sheath is retracted.

In one embodiment of the invention, hemostasis valve 12900, shown in FIGS. 129A-D, includes longitudinal valve housing 12902 defining slot 12904 that extends transversely to major longitudinal axis 12906 of valve housing 12902. Longitudinal valve housing 12902 defines interior surface 12908 and has proximal end 12910 and distal end 12912. Gasket 12914 defines interior conduit 12916 and has distal end 12918, wherein distal end 12918 is fixed relative to longitudinal valve housing 12902, and proximal end 12920 that is moveable relative to longitudinal valve housing 12902. Gasket 12914 also includes collapsible intermediate portion 12922 between distal end 12918 and proximal end 12920. In one embodiment, intermediate portion 12922 has a narrow internal diameter relative to the remainder of interior conduit 12916 when gasket 12914 is fully open. On another embodiment, interior conduit 12916 of gasket 12914 has an essentially constant diameter from distal end 12918 to proximal end 12920 of gasket 12914. Internal diameter of intermediate portion 12922 is further reduced by rotating at least one end relative to the other end of gasket 12914 about major longitudinal axis 12906 that extends through gasket 12914. Examples of suitable materials of gasket 12914 include those that are known in the art, such as at least one material selected from the group consisting of silicon, urethane, rubber and latex. In one preferred embodiment, gasket 12914 includes silicon. In one specific embodiment, gasket 12914 includes a coating of silicon. Grip assembly 12924 is located at proximal end 12910 of longitudinal valve housing 12902. Grip assembly 12924 includes grip portion 12926 at first end 12910 of longitudinal valve housing 12902. Spindle portion 12928 of grip assembly 12924 is fixed to grip portion 12926 by screw 12930 and extends from grip portion 12926 into interior surface 12908 of longitudinal valve housing 12902. As can be seen in FIG. 130, spindle portion 12928 is fixed to proximal end 12920 (FIG. 129A) of gasket 12914 by proximal oetiker clamp 12932. Returning to FIGS. 129A-D, ratchet 12934 extends about spindle portion 12928 and is fixed to spindle portion 12920 by pin 12936, which also extends through slot 12904 of longitudinal valve housing 12902. Ratchet 12934 defines teeth 12938 at an end of ratchet 12934 extending about spindle portion 12928.

As can be seen in FIGS. 131A-C, longitudinal valve housing 12902 includes lip 12940 at proximal end 12910 that defines distally-facing surface 12942 at interior surface 12908. Spring, such as wave spring 12944 extends about spindle portion 12928 and is located between grip portion 12926 at distally-facing surface 12942 and from ratchet 12934. In another embodiment, the spring is a compression spring. Alternatively, other suitable springs, such as are known in the art, may be employed as alternatives to wave spring. Wave spring 12944 biases ratchet 12934 in a distal direction 12946 and relative to major longitudinal axis 12906 (FIGS. 129A, 129B).

Ratchet 12934 extends about spindle portion 12928 and is held in place between wave spring 12944 and interference element 12948, which, also extends about spindle portion 12928. Interference element 12948 is fixed to the longitudinal valve housing 12902 by screws 12950. Distal end 12918 of gasket 12914 is fixed to main boss 12952 by distal oetiker clamp 12954. Main boss 12952 (FIGS. 129A, 129B) is fixed at the distal end 12912 of longitudinal valve housing 12902 by screw 12956.

In one embodiment, interference element 12948 includes at least one pin (not shown) that interfaces with teeth 12938 of ratchet. In another embodiment, interference element 12948 defines teeth 12958 that interface with teeth 12938 of ratchet 12934. Interference element 12948 engages potentially a plurality of different positions relative to ratchet 12934, each position thereby corresponding to a distinct position of gasket 12914 between a fully opened position and a fully closed position. The position of gasket 12914, between a fully-open and a fully-closed position, is indicated by the position of pin 12936 within slot 12904, as shown in FIGS. 131A-C. Gasket 12914 is conformable about at least one catheter (not shown) extending through gasket 12914.

Rotation of grip portion 12926 causes rotation of spindle portion 12928 and, consequently, rotation of proximal end 12920 of gasket 12914 relative to distal end 12918 of gasket 12914, thereby closing gasket 12914 when grip portion 12926 is rotated in one direction shown in FIG. 131B, and opening gasket 12914 when grip portion 12926 is rotated in an opposite direction, shown in FIG. 131C. Interference between teeth 12958 of interference element 12948 with teeth 12938 of ratchet 12934 causes grip assembly 12924 and, consequently, gasket 12914, to remain in position at potentially distinct positions of gasket 12914 in a fully closed position, a fully open position, and positions between fully open and fully closed. Interference element 12948 and ratchet 12934 remain in respective relative positions when ratchet 12934 is not forced into a different rotational position relative to interference element 12948 by operation of the surgeon. Wave spring 12944, forces teeth 12938 of ratchet 12934 against teeth 12938 of interference element 12948.

Referring to FIGS. 129A-129D, x-valves 12960, 12962 are stacked at distal end 12913 within recessed portion 12964 of main boss 12952 and held in place by spring pins 12966 and gasket spacer 12968. x-valves 12960, 12962 each include at least one sealing component 12970, wherein sealing component 12970 defines at least one slot 12972. Support layer 12998 of x-valve 12960 is at least partially embedded within sealing component 12970. As shown, sealing component 12970 of x-valve 12960 includes a plurality of slots 12972,12978. Slots 12972,12978 intersect with each other. In one embodiment, slots 12972,12978 intersect at different angles. As shown, in FIG. 132A, slots 12972,12978 intersect at the same angle. In another embodiment, shown in FIG. 132B, x-valve 12961 includes a plurality of sealing layers 12980,12982. In one embodiment, each sealing layer includes at least one slot. As shown in FIG. 132B, slots 12984,12986 of sealing layers 12980, 12982 are substantially aligned. In another embodiment, (not shown) slots 12980,12982 of sealing layers 12980, 12982 can be offset from each other. Respective intersecting slots of each sealing layer can be offset from each other by one-half of the angle of intersection of the slots of each sealing component. Sealing components 12980,12982 of each x-valve are partitioned by support 12998. In a preferred embodiment, shown in FIG. 132B, each sealing component 12980,12982 has a pair of slots 12984,12986 that intersect at right angles. Referring back to FIG. 129C, slots 12972, 12990 of respective x-valves 12960,12962, are offset from each other by one-half of the angle of intersection of their respective slots. In alternative embodiments, not shown, slots 12974,12978 of respective x-valves 12960,12962 are aligned.

Typically, the sealing layers are formed of a suitable material, such as is known in the art. Examples of suitable sealing materials include at least one member selected from the group consisting of silicon, urethane, rubber and latex.

As can be seen, support layer 12998 of x-valve 12960 includes peripheral ring 12992 and plurality of arms 12994 extending from peripheral ring 12992 to points proximate to the intersection of slots 12972. Support of each x-valve is formed of a suitable material, such as is known in the art. Examples of suitable materials of support layer 12998 include nitinol and titanium. In a preferred embodiment, support layer includes nitinol.

Wiper 12996 is held between gasket spacer 12968 and O-ring spacer 12999 at distal end 12912 of hemostasis valve. Spring pins 13002 extend through O-ring spacer 12999, gasket spacer 12968 and main boss 12952, and server as assembly aids. Screws 13000 extend through O-ring spacer 12999 and main boss 12952 and thread into longitudinal valve housing 12902 to thereby hold O-ring spacer 12999, main boss 12952, and all intermediate components in place.

The teachings of all patents, published applications and references cited herein are incorporated by reference in their entirety. The teaching of U.S. Pat. Nos. 7,763,063; 8,292,943; 8,308,790; 8,007,605; 8,070,790; 8,062,349 and U.S. patent application Ser. Nos. 11/699,700; 11/700,609; 11/449,337; 11/701,867; 11/449,337; 11/701,876; 11/828,653; 11/828,675; 12/137,592 and 12/723,431 are also incorporated by reference herein in their entirety. While this invention has been particularly shown and described with references to example embodiments thereof, it will be understood by those skilled in the art that various changes in form and details may be made therein without departing from the scope of the invention encompassed by the appended claims.

What is claimed is:

1. A stent graft delivery system, comprising:
   a) a handle that includes
      i) a distal grip, and
      ii) a handle body extending from one end of the distal grip, the handle defining a conduit and a track along a portion of the length of the distal grip and the handle body,
   b) an internal lead screw assembly within the track, the internal lead screw and assembly being movable along a major axis of the conduit and including a threaded portion that extends through the track;
   c) a lead screw nut that extends about the handle body and threadably engaged with the threaded portion of the internal lead screw assembly, whereby rotation of the lead screw nut while abutting the distal grip causes movement of the internal lead screw assembly relative to the handle;
   d) a support member fixed to the handle body,
   e) a sheath extending about a portion of the support member and fixed to the internal lead screw assembly, whereby relative movement of the handle body and the lead screw assembly causes relative movement of the support member and the sheath, wherein the support member includes a hypo-tube and a support tube within the hypo-tube, wherein the hypo-tube is fixed to the handle body, and wherein the internal lead screw assembly defines an opening essentially coaxial with the handle, wherein the support member extends through the internal lead screw assembly; and
   f) a hemostasis valve about the support member and between the sheath and the internal lead screw assembly, the hemostasis valve including an x-valve having
      i) a valve housing,
      ii) at least one sealing component within the valve housing, the sealing component defining a plurality of slots that intersect with each other, and
      iii) a support layer that includes nitinol and partitions the sealing component, the support layer including a peripheral ring and a plurality of arms extending from the peripheral ring to points proximate to intersection of the plurality of slots, the plurality of arms embedded within the sealing component, whereby the x-valve forms a seal about a guidewire extending through the x-valve while the x-valve moves relative to the guidewire regardless of the direction in which the x-valve is moved relative to the guidewire.

2. The stent graft delivery system of claim 1, wherein the plurality of slots intersect at different angles.

3. The stent graft delivery system of claim 1, wherein the plurality of slots all intersect at the same angle.

4. The stent graft delivery system of claim 1, wherein the at least one sealing component includes a plurality of sealing layers, wherein the slots of the sealing layers are substantially aligned.

5. The stent graft delivery system of claim 1, wherein the at least one sealing component includes a plurality of sealing layers, wherein the plurality of slots of the sealing layers are offset from each other.

6. The stent graft delivery system of claim 1, wherein the at least one sealing component includes at least two sealing components abutting each other, each of which define at least one slot, and wherein the at least two sealing components are partitioned by the support layer.

7. The stent graft delivery system of claim 6, wherein the intersecting slots of the respective sealing components are offset from each other.

8. The stent graft delivery system of claim 7, wherein the respective intersecting slots are offset from each other by one half of the angle of intersection of the slots of each sealing component.

9. The stent graft delivery system of claim 8, wherein each sealing component has a pair of slots that intersect at right angles.

10. The stent graft delivery system of claim 1, wherein the at least one sealing component includes at least one material selected from the group consisting of silicone, urethane, rubber and latex.

* * * * *